(12) United States Patent
Liu et al.

(10) Patent No.: US 10,336,997 B2
(45) Date of Patent: *Jul. 2, 2019

(54) CONTINUOUS DIRECTED EVOLUTION

(71) Applicant: President and Fellows of Harvard College, Cambridge, MA (US)

(72) Inventors: David R. Liu, Lexington, MA (US); Kevin Michael Esvelt, Cambridge, MA (US); Jacob Charles Carlson, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 259 days.

This patent is subject to a terminal disclaimer.

(21) Appl. No.: 15/188,627

(22) Filed: Jun. 21, 2016

(65) Prior Publication Data

US 2017/0009224 A1 Jan. 12, 2017

Related U.S. Application Data

(63) Continuation of application No. 13/996,208, filed as application No. PCT/US2011/066747 on Dec. 22, 2011, now Pat. No. 9,394,537.

(Continued)

(51) Int. Cl.
*C40B 60/08* (2006.01)
*C12N 15/10* (2006.01)
(Continued)

(52) U.S. Cl.
CPC ........ *C12N 15/1058* (2013.01); *C07K 14/005* (2013.01); *C12N 7/00* (2013.01);
(Continued)

(58) Field of Classification Search
None
See application file for complete search history.

(56) References Cited

U.S. PATENT DOCUMENTS 5,057,432 A 10/1991 Wangersky et al.
5,223,409 A 6/1993 Ladner et al.
(Continued)

FOREIGN PATENT DOCUMENTS

JP H0937764 A 2/1997
WO WO 90/02809 A1 3/1990
(Continued)

OTHER PUBLICATIONS

Extended European Search Report for EP EP 09812363, dated Mar. 30, 2012.
(Continued)

*Primary Examiner* — Christian C Boesen
(74) *Attorney, Agent, or Firm* — Wolf, Greenfield & Sacks, P.C.

(57) ABSTRACT

The invention provides systems, methods, reagents, apparatuses, vectors, and host cells for the continuous evolution of nucleic acids. For example, a lagoon is provided in which a population of viral vectors comprising a gene of interest replicates in a stream of host cells, wherein the viral vectors lack a gene encoding a protein required for the generation of infectious viral particles, and wherein that gene is expressed in the host cells under the control of a conditional promoter, the activity of which depends on a function of the gene of interest to be evolved. Some aspects of this invention provide evolved products obtained from continuous evolution procedures described herein. Kits containing materials for continuous evolution are also provided.

20 Claims, 19 Drawing Sheets
Specification includes a Sequence Listing.

Related U.S. Application Data

(60) Provisional application No. 61/426,139, filed on Dec. 22, 2010.

(51) Int. Cl.
*C12N 15/85* (2006.01)
*C12N 15/86* (2006.01)
*C07K 14/005* (2006.01)
*C12N 7/00* (2006.01)
*C12N 15/70* (2006.01)
*C40B 50/06* (2006.01)

(52) U.S. Cl.
CPC ............ *C12N 15/70* (2013.01); *C12N 15/85* (2013.01); *C12N 15/86* (2013.01); *C12N 2795/14121* (2013.01); *C12N 2795/14152* (2013.01); *C40B 50/06* (2013.01); *C40B 60/08* (2013.01)

(56) References Cited

U.S. PATENT DOCUMENTS

| | | |
|---|---|---|
| 5,658,727 A | 8/1997 | Barbas et al. |
| 5,712,089 A | 1/1998 | Borrebaeck et al. |
| 5,821,047 A | 10/1998 | Garrard et al. |
| 5,965,124 A | 10/1999 | Feinberg et al. |
| 6,156,509 A | 12/2000 | Schellenberger |
| 6,429,298 B1 | 8/2002 | Ellington et al. |
| 6,969,731 B1 | 11/2005 | Tang et al. |
| 9,023,594 B2 | 5/2015 | Liu et al. |
| 9,267,127 B2 | 2/2016 | Liu et al. |
| 9,394,537 B2 | 7/2016 | Liu et al. |
| 9,771,574 B2 | 9/2017 | Liu et al. |
| 2002/0132327 A1 | 9/2002 | Hay et al. |
| 2003/0119764 A1 | 6/2003 | Loeb et al. |
| 2003/0203480 A1 | 10/2003 | Kovesdi et al. |
| 2005/0019753 A1 | 1/2005 | Kukolj et al. |
| 2008/0220502 A1 | 9/2008 | Schellenberger et al. |
| 2009/0215110 A1 | 8/2009 | Gibson et al. |
| 2009/0227463 A1 | 9/2009 | Reif et al. |
| 2009/0300777 A1 | 12/2009 | Nakayama |
| 2011/0177495 A1 | 7/2011 | Liu et al. |
| 2012/0231498 A1 | 9/2012 | Shaw et al. |
| 2013/0059931 A1 | 3/2013 | Petersen-Mahrt et al. |
| 2013/0117869 A1 | 5/2013 | Duchateau et al. |
| 2013/0345065 A1 | 12/2013 | Liu et al. |
| 2014/0057317 A1 | 2/2014 | Liu et al. |
| 2014/0201858 A1 | 7/2014 | Ostertag et al. |
| 2015/0056177 A1 | 2/2015 | Liu et al. |
| 2015/0275202 A1 | 10/2015 | Liu et al. |
| 2016/0348096 A1 | 12/2016 | Liu et al. |
| 2017/0029473 A1 | 2/2017 | Liu et al. |
| 2017/0044520 A1 | 2/2017 | Liu et al. |
| 2017/0233708 A1 | 8/2017 | Liu et al. |
| 2018/0087046 A1 | 3/2018 | Liu et al. |

FOREIGN PATENT DOCUMENTS

| | | |
|---|---|---|
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 96/04403 A1 | 2/1996 |
| WO | WO 98/32845 A1 | 7/1998 |
| WO | WO 00/71694 A1 | 11/2000 |
| WO | WO 01/05950 A2 | 1/2001 |
| WO | WO 01/61049 A1 | 8/2001 |
| WO | WO 2005/081632 A2 | 9/2005 |
| WO | WO 2007/066923 A1 | 6/2007 |
| WO | WO 2008/005529 A2 | 1/2008 |
| WO | WO 2009/082488 A2 | 7/2009 |
| WO | WO 2009/108180 A2 | 9/2009 |
| WO | WO 2010/028347 A2 | 3/2010 |
| WO | WO 2011/147590 A2 | 12/2011 |
| WO | WO 2011/066747 A1 | 6/2012 |
| WO | WO 2012/088381 A2 | 6/2012 |
| WO | WO 2014/039585 A2 | 3/2014 |
| WO | WO 2014/157820 A1 | 10/2014 |
| WO | WO 2014/158593 A1 | 10/2014 |

OTHER PUBLICATIONS

International Search Report and Written Opinion for PCT/US2009/056194, dated Jun. 21, 2010.
International Preliminary Report on Patentability for PCT/US2009/056194, dated Mar. 17, 2011.
Invitation to Pay Additional Fees for PCT/US2011/066747, dated Aug. 30, 2012.
International Search Report and Written Opinion for PCT/US2011/066747, dated Oct. 30, 2012.
International Preliminary Report on Patentability for PCT/US2011/066747, dated Jul. 4, 2013.
International Search Report and Written Opinion for PCT/US2015/012022, dated Sep. 25, 2015.
International Preliminary Report on Patentability for PCT/US2015/012022, dated Aug. 4, 2016.
Invitation to Pay Additional Fees for PCT/US/2016/043559, dated Jan. 12, 2017.
International Search Report and Written Opinion for PCT/US/2016/043559, dated Mar. 10, 2017.
International Search Report and Written Opinion for PCT/US2015/057012, dated Jun. 10, 2016.
International Search Report and Written Opinion for PCT/US2016/027795, dated Aug. 11, 2016.
Invitation to Pay Additional Fees for PCT/US2016/044546, dated Oct. 12, 2016.
International Search Report and Written Opinion for PCT/US2016/044546, dated Dec. 28, 2016.
International Search Report and Written Opinion for PCT/US2016/043513, dated Nov. 30, 2016.
Ahluwalia et al., Hypermutability and error catastrophe due to defects in ribonucleotide reductase. Proc Natl Acad Sci U S A. Nov. 12, 2013;110(46):18596-601. doi: 10.1073/pnas.1310849110. Epub Oct. 28, 2013.
Akopian et al., Chimeric recombinases with designed DNA sequence recognition. Proc Natl Acad Sci U S A. Jul. 22, 2003;100(15):8688-91. Epub Jul. 1, 2003.
Armstrong et al., Chapter 3. Vectors for Phage Display. In: Phage Display of Peptides and Proteins. Kay et al., eds. Academic Press. San Diego, CA. 1996:35-53.
Badran et al., Development of potent in vivo mutagenesis plasmids with broad mutational spectra. Nat Commun. Oct. 7, 2015;6:8425. doi: 10.1038/ncomms9425.
Baker et al., Chemical complementation: a reaction-independent genetic assay for enzyme catalysis. Proc Natl Acad Sci U S A. Dec. 24, 2002;99(26):16537-42. Epub Dec. 13, 2002.
Barbas et al., Assembly of combinatorial antibody libraries on phage surfaces: the gene III site. Proc Natl Acad Sci U S A. Sep. 15, 1991;88(18):7978-82.
Bennet et al., Unlocking of the filamentous bacteriophage virion during infection is mediated by the C domain of pIII. J Mol Biol. Feb. 17, 2006;356(2):266-73. Epub Dec. 9, 2005.
Birling et al., Site-specific recombinases for manipulation of the mouse genome. Methods Mol Biol. 2009;561:245-63. doi: 10.1007/978-1-60327-019-9_16.
Bloom et al., Evolving strategies for enzyme engineering. Curr Opin Struct Biol. Aug. 2005;15(4):447-52.
Boch et al., Breaking the code of DNA binding specificity of Tal-type III effectors. Science. Dec. 11, 2009;326(5959):1509-12. doi: 10.1126/science.1178811.
Boersma et al., Selection strategies for improved biocatalysts. FEBS J. May 2007;274(9):2181-95.

(56) References Cited

OTHER PUBLICATIONS

Bolusani et al., Evolution of variants of yeast site-specific recombinase Flp that utilize native genomic sequences as recombination target sites. Nucleic Acids Res. 2006;34(18):5259-69. Epub Sep. 26, 2006.
Braun et al., Immunogenic duplex nucleic acids are nuclease resistant. J Immunol. Sep. 15, 1988;141(6):2084-9.
Breaker et al., Emergence of a replicating species from an in vitro RNA evolution reaction. Proc Natl Acad Sci U S A. Jun. 21, 1994;91(13):6093-7.
Brieba et al., Role of T7 RNA polymerase His784 in start site selection and initial transcription. Biochemistry. Apr. 23, 2002;41(16):5144-9.
Buchholz et al., Alteration of Cre recombinase site specificity by substrate-linked protein evolution. Nat Biotechnol. Nov. 2001;19(11):1047-52.
Caldwell et al., Randomization of Genes by PCR Mutagenesis. PCR Methods Applic. 1992;2:28-33.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014.
Chasteen et al., Eliminating helper phage from phage display. Nucleic Acids Res. 2006;34(21):e145. Epub Nov. 6, 2006.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Cheetham et al., Structural basis for initiation of transcription from an RNA polymerase-promoter complex. Nature. May 6, 1999;399(6731):80-3.
Chen et al., Information theory based T7-like promoter models: classification of bacteriophages and differential evolution of promoters and their polymerases. Nucleic Acids Res. Oct. 31, 2005;33(19):6172-87. Print 2005.
Clackson et al., Making antibody fragments using phage display libraries. Nature. Aug. 15, 1991;352(6336):624-8.
Click et al., Filamentous phage infection: required interactions with the TolA protein. J Bacteriol. Oct. 1997;179(20):6464-71.
Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.
Corey et al., Trypsin display on the surface of bacteriophage. Gene. Jun. 15, 1993;128(1):129-34.
Crameri et al., Display of biologically active proteins on the surface of filamentous phages: a cDNA cloning system for selection of functional gene products linked to the genetic information responsible for their production. Gene. Dec. 27, 1993;137(1):69-75.
Cwirla et al., Peptides on phage: a vast library of peptides for identifying ligands. Proc Natl Acad Sci U S A. Aug. 1990;87(16):6378-82.
Das et al., Viral evolution as a tool to improve the tetracycline-regulated gene expression system. J Biol Chem. Apr. 30, 2004;279(18):18776-82. Epub Feb. 2, 2004.
Datsenko et al., One-step inactivation of chromosomal genes in *Escherichia coli* K-12 using PCR products. Proc Natl Acad Sci U S A. Jun. 6, 2000;97(12):6640-5.
Davis et al., Viral mutagenesis as a means for generating novel proteins. J Virol. Feb. 2010;84(3):1625-30. Epub Nov. 11, 2009.
De Haard et al., A large non-immunized human Fab fragment phage library that permits rapid isolation and kinetic analysis of high affinity antibodies. J Biol Chem. Jun. 25, 1999;274(26):18218-30.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Drake, A constant rate of spontaneous mutation in DNA-based microbes. Proc Natl Acad Sci U S A. Aug. 15, 1991;88(16):7160-4.

Durniak et al., The structure of a transcribing T7 RNA polymerase in transition from initiation to elongation. Science. Oct. 24, 2008;322(5901):553-7.
Esvelt et al., A system for the continuous directed evolution of biomolecules. Nature. Apr. 28, 2011;472(7344):499-503. Epub Apr. 10, 2011.
Fijalkowska et al., Mutants in the Exo I motif of *Escherichia coli* dnaQ: defective proofreading and inviability due to error catastrophe. Proc Natl Acad Sci U S A. Apr. 2, 1996;93(7):2856-61.
Fowlkes et al., Multipurpose vectors for peptide expression on the M13 viral surface. Biotechniques. Sep. 1992;13(3):422-8.
Friedberg et al., Error-prone DNA polymerases: novel structures and the benefits of infidelity. Cell. Oct. 5, 2001;107(1):9-12.
Fuchs et al., Targeting Recombinant Antibodies to the Surface of *Escherichia coli*: Fusion to a Peptidoglycan Associated Lipoprotein. Bio/Technology. 1991;9:1370-72.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Garrard et al., Fab assembly and enrichment in a monovalent phage display system. Biotechnology (N Y). Dec. 1991;9(12):1373-7.
Gibson et al., Enzymatic assembly of DNA molecules up to several hundred kilobases. Nat Methods. May 2009;6(5):343-5. Epub Apr. 12, 2009.
Gordley et al., Evolution of programmable zinc finger-recombinases with activity in human cells. J Mol Biol. Mar. 30, 2007;367(3):802-13. Epub Jan. 12, 2007.
Gram et al., In vitro selection and affinity maturation of antibodies from a naive combinatorial immunoglobulin library. Proc Natl Acad Sci U S A. Apr. 15, 1992;89(8):3576-80.
Griffiths et al., Human anti-self antibodies with high specificity from phage display libraries. EMBO J. Feb. 1993;12(2):725-34.
Hart et al., Directed Evolution to Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.
Hawkins et al., Selection of phage antibodies by binding affinity. Mimicking affinity maturation. J Mol Biol. Aug. 5, 1992;226(3):889-96.
Hay et al., Bacteriophage cloning and *Escherichia coli* expression of a human IgM Fab. Hum Antibodies Hybridomas. Apr. 1992;3(2):81-5.
Hoogenboom et al., Antibody phage display technology and its applications. Immunotechnology. Jun. 1998;4(1):1-20.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hoogenboom et al., Natural and designer binding sites made by phage display technology. Immunol Today. Aug. 2000;21(8):371-8.
Houshmand et al., Use of Bateriophage T7 Displayed Peptides for Determination of Monoclonal Anitbody Specificity and Biosensor Analysis of the Binding Reaction. Anal Biochem. 1999;268:363-70.
Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015.
Huse et al., Generation of a large combinatorial library of the immunoglobulin repertoire in phage lambda. Science. Dec. 8, 1989;246(4935):1275-81.
Husimi et al., Cellstat-a continuous culture system of a bacteriophage for the study of the mutation rate and the selection process of the DNA level. Rev Sci Instrum. Apr. 1982;53(4):517-22.
Husimi, Selection and evolution of bacteriophages in cellstat. Adv Biophys. 1989;25:1-43.
Ichetovkin et al., Substrate recognition by the leucyl/phenylalanyl-tRNA-protein transferase Conservation within the enzyme family and localization to the trypsin-resistant domain. J Biol Chem. Dec. 26, 1997;272(52):33009-14.
Ikeda et al., In vivo and in vitro activities of point mutants of the bacteriophage T7 RNA polymerase promoter. Biochemistry. Sep. 22, 1992;31(37):9073-80.
Ikeda et al., Selection and characterization of a mutant T7 RNA polymerase that recognizes an expanded range of T7 promoter-like sequences. Biochemistry. Sep. 7, 1993;32(35):9115-24.

(56) References Cited

OTHER PUBLICATIONS

Imburgio et al., Studies of promoter recognition and start site selection by T7 RNA polymerase using a comprehensive collection of promoter variants. Biochemistry. Aug. 29, 2000;39(34):10419-30.
Irion et al., Identification and targeting of the ROSA26 locus in human embryonic stem cells. Nat Biotechnol. Dec. 2007;25(12):1477-82. Epub Nov. 25, 2007.
Johns et al., The promise and peril of continuous in vitro evolution. J Mol Evol. Aug. 2005;61(2):253-63. Epub Jun. 27, 2005.
Joho et al., Identification of a region of the bacteriophage T3 and T7 RNA polymerases that determines promoter specificity. J Mol Biol. Sep. 5, 1990;215(1):31-9.
Joung et al., A bacterial two-hybrid selection system for studying protein-DNA and protein-protein interactions. Proc Natl Acad Sci U S A. Jun. 20, 2000;97(13):7382-7.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Khlebnikov et al., Modulation of gene expression from the arabinose-inducible araBAD promoter. J Ind Microbiol Biotechnol. Jul. 2002;29(1):34-7.
Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.
Kozak et al., Structural features in eukaryotic mRNAs that modulate the initiation of translation. J Biol Chem. Oct. 25, 1991;266(30):19867-70.
Kuzmine et al., Binding of the priming nucleotide in the initiation of transcription by T7 RNA polymerase. J Biol Chem. Jan. 31, 2003;278(5):2819-23. Epub Nov. 9, 2002.
Latimer et al., Specificity of monoclonal antibodies produced against phosphorothioate and ribo modified DNAs. Mol Immunol. Oct. 1995;32(14-15):1057-64.
Lincoln et al., Self-sustained replication of an RNA enzyme. Science. Feb. 27, 2009;323(5918):1229-32. Epub Jan. 8, 2009.
Lindemann et al., Evolution of bacteriophage in continuous culture: a model system to test antiviral gene therapies for the emergence of phage escape mutants. J Virol. Jun. 2002;76(11):5784-92.
Lutz et al., Creating multiple-crossover DNA libraries independent of sequence identity. Proc Natl Acad Sci U S A. Sep. 25, 2001;98(20):11248-53. Epub Sep. 18, 2001.
Makeyev et al., Evolutionary potential of an RNA virus. J Virol. Feb. 2004;78(4):2114-20.
Malmborg et al., Selective phage infection mediated by epitope expression on F pilus. J Mol Biol. Oct. 31, 1997;273(3):544-51.
Martin et al., Kinetic analysis of T7 RNA polymerase-promoter interactions with small synthetic promoters. Biochemistry. May 19, 1987;26(10):2690-6.
McCafferty et al., Phage antibodies: filamentous phage displaying antibody variable domains. Nature. Dec. 6, 1990;348(6301):552-4.
McConnell et al., Constrained peptide libraries as a tool for finding mimotopes. Gene. Dec. 30, 1994;151(1-2):115-8.
Milligan et al., Oligoribonucleotide synthesis using T7 RNA polymerase and synthetic DNA templates. Nucleic Acids Res. Nov. 11, 1987;15(21):8783-98.
Mills et al., Qn extracellular Darwinian experiment with a self-duplicating nucleic acid molecule. Proc Natl Acad Sci U S A. Jul. 1967;58(1):217-24.
Nelson et al., Filamentous phage DNA cloning vectors: a noninfective mutant with a nonpolar deletion in gene III. Virology. Jan. 30, 1981;108(2):338-50.
Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.
O'Maille et al., Structure-based combinatorial protein engineering (SCOPE). J Mol Biol. Aug. 23, 2002;321(4):677-91.

Opperman et al., a model for a umuDC-dependent prokaryotic DNA damage checkpoint. Proc Natl Acad Sci U S A. Aug. 3, 1999;96(16):9218-23.
Ostendorf et al., Characterization of a dam mutant of Serratia marcescens and nucleotide sequence of the dam region. J Bacteriol. Jul. 1999;181(13):3880-5.
Ostermeier e al., A combinatorial approach to hybrid enzymes independent of DNA homology. Nat Biotechnol. Dec. 1999;17(12):1205-9.
Peyrottes et al., Oligodeoxynucleoside phosphoramidates (P-NH2): synthesis and thermal stability of duplexes with DNA and RNA targets. Nucleic Acids Res. May 15, 1996;24(10):1841-8.
Rakonjac et al., Roles of pIII in filamentous phage assembly. J Mol Biol. Sep. 11, 1998;282(1):25-41.
Raskin et al., Substitution of a single bacteriophage T3 residue in bacteriophage T7 RNA polymerase at position 748 results in a switch in promoter specificity. J Mol Biol. Nov. 20, 1992;228(2):506-15.
Raskin et al., T7 RNA polymerase mutants with altered promoter specificities. Proc Natl Acad Sci U S A. Apr. 15, 1993;90(8):3147-51.
Rebar et al., Phage display methods for selecting zinc finger proteins with novel DNA-binding specificities. Methods Enzymol. 1996;267:129-49.
Reidhaar-Olson et al., Random mutagenesis of protein sequences using oligonucleotide cassettes. Methods Enzymol. 1991;208:564-86.
Reuven et al., Lesion bypass by the *Escherichia coli* DNA polymerase V requires assembly of a RecA nucleoprotein filament. J Biol Chem. Feb. 23, 2001;276(8):5511-7. Epub Nov. 17, 2000.
Riechmann et al., The C-terminal domain of TolA is the coreceptor for filamentous phage infection of *E. coli*. Cell. Jul. 25, 1997;90(2):351-60.
Ringquist et al., Translation initiation in *Escherichia coli*: sequences within the ribosome-binding site. Mol Microbiol. May 1992;6(9):1219-29.
Rosenberg et al., T7 Select® Phage Display System: A Powerful new protein display system based on bacteriophage T7. Innovations. 1996;6:1-6.
Santini et al., Efficient display of an HCV cDNA expression library as C-terminal fusion to the capsid protein D of bacteriophage lambda. J Mol Biol. Sep. 11, 1998;282(1):125-35.
Santoro et al., Directed evolution of the site specificity of Cre recombinase. Proc Natl Acad Sci U S A. Apr. 2, 2002;99(7):4185-90. Epub Mar. 19, 2002.
Schultz et al., Oligo-2'-fluoro-2'-deoxynucleotide N3'-->P5' phosphoramidates: synthesis and properties. Nucleic Acids Res. Aug. 1, 1996;24(15):2966-73.
Scott et al., Searching for peptide ligands with an epitope library. Science. Jul. 27, 1990;249(4967):386-90.
Sices et al., A genetic screen for the isolation and characterization of site-specific proteases. Proc Natl Acad Sci U S A. Mar. 17, 1998;95(6):2828-33.
Sices et al., Rapid genetic selection of inhibitor-resistant protease mutants: clinically relevant and novel mutants of the HIV protease. Aids Res Hum Retroviruses. Sep. 1, 2001;17(13):1249-55.
Sieber et al., Libraries of hybrid proteins from distantly related sequences. Nat Biotechnol. May 2001;19(5):456-60.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Smith, Filamentous fusion phage: novel expression vectors that display cloned antigens on the virion surface. Science. Jun. 14, 1985;228(4705):1315-7.
Stemmer, Rapid evolution of a protein in vitro by DNA shuffling. Nature. Aug. 4, 1994;370(6488):389-91.
Sutter et al., Non-replicating vaccinia vector efficiently expresses bacteriophage T7 RNA polymerase. FEBS Lett. Aug. 28, 1995;371(1):9-12.
Torres et al., Non-integrative lentivirus drives high-frequency cre-mediated cassette exchange in human cells. PLoS One. 2011;6(5):e19794. doi: 10.1371/journal.pone.0019794. Epub May 23, 2011.

(56) References Cited

OTHER PUBLICATIONS

Tsuji et al., Random multi-recombinant PCR for the construction of combinatorial protein libraries. Nucleic Acids Res. Oct. 15, 2001;29(20):E97.
Tzagoloff et al., The Initial Steps in Infection With Coliphage M13. Virology. Nov. 1964;24:372-80.
Vidal et al., Yeast forward and reverse 'n'-hybrid systems. Nucleic Acids Res. Feb. 15, 1999;27(4):919-29.
Vidal-Aroca et al., One-step high-throughput assay for quantitative detection of beta-galactosidase activity in intact gram-negative bacteria, yeast, and mammalian cells. Biotechniques. Apr. 2006;40(4):433-4, 436, 438 passim.
Voigt et al., Rational evolutionary design: the theory of in vitro protein evolution. Adv Protein Chem. 2000;55:79-160.
Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Programming cells by multiplex genome engineering and accelerated evolution. Nature. Aug. 13, 2009;460(7257):894-8. Epub Jul. 26, 2009.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wright et al., Continuous in vitro evolution of catalytic function. Science. Apr. 25, 1997;276(5312):614-7.
Yuan et al., Laboratory-directed protein evolution. Microbiol Mol Biol Rev. Sep. 2005;69(3):373-92.
Zhou et al., Optimization of the Tet-On system for regulated gene expression through viral evolution. Gene Ther. Oct. 2006;13(19):1382-90. Epub May 25, 2006.
U.S. Appl. No. 15/713,403, filed Sep. 22, 2017, Liu et al.
U.S. Appl. No. 15/518,639, filed Apr. 12, 2017, Liu et al.
U.S. Appl. No. 15/567,312, filed Oct. 17, 2017, Liu et al.
U.S. Appl. No. 15/748,053, filed Jan. 26, 2018, Liu et al.
Extended European Search Report for EP 16 20 3684, dated May 26, 2017.
Extended European Search Report for EP 17 16 0955, dated May 16, 2017.
International Preliminary Report on Patentability for PCT/US/2016/043559, dated Feb. 1, 2018.
International Preliminary Report on Patentability for PCT/US2015/057012, dated May 4, 2017.
International Preliminary Report on Patentability for PCT/US2016/027795, dated Oct. 26, 2017.
International Preliminary Report on Patentability for PCT/US2016/044546, dated Feb. 8, 2018.
International Preliminary Report on Patentability for PCT/US2016/043513, dated Feb. 1, 2018.
Invitation to Pay Additional Fees for PCT/US2018/14867, dated Apr. 5, 2018.
International Search Report and Written Opinion for PCT/US2018/14867, dated May 23, 2018.
Badran et al., In vivo continuous directed evolution. Curr Opin Chem Biol. 2014;1-10.
Dickinson et al., A system for the continuous directed evolution of proteases rapidly reveals drug-resistance mutations. Nat Commun. Oct. 30, 2014;5:5352. doi: 10.1038/ncomms6352.
Leconte et al., A population-based experimental model for protein evolution: effects of mutation rate and selection stringency on evolutionary outcomes. Biochemistry. Feb. 26, 2013;52(8): 1490-1499.
Lei et al., Efficient targeted gene disruption in Xenopus embryos using engineered transcription activator-like effector nucleases (TALENs). PNAS Oct. 23, 2012;109(43):17484-17489; https://doi.org/10.1073/pnas.1215421109.
Maeder et al., Robust, synergistic regulation of human gene expression using TALE activators. Nat Methods. Mar. 2013;10(3):243-5. doi: 10.1038/nmeth.2366. Epub Feb. 10, 2013.
U.S. Appl. No. 13/062,098, filed Apr. 4, 2011, Liu et al.
U.S. Appl. No. 14/704,226, filed May 5, 2015, Liu et al.
U.S. Appl. No. 13/996,208, filed Jun. 20, 2013, Liu et al.
U.S. Appl. No. 15/112,759, filed Jul. 20, 2016, Liu et al.
U.S. Appl. No. 15/217,839, filed Jul. 22, 2016, Liu et al.
U.S. Appl. No. 15/216,844, filed Jul. 22, 2016, Liu et al.

SEQUENCE LISTING

```
<160> NUMBER OF SEQ ID NOS: 35

<210> SEQ ID NO 1
<211> LENGTH: 6407
<212> TYPE: DNA
<213> ORGANISM: M13 phage

<400> SEQUENCE: 1
aacgctacta ctattagtag aattgatgcc acctttcag ctcgcgcccc aaatgaaaat      60
atagctaaac aggttattga ccatttgcga aatgtatcta atggtcaaac taaatctact    120
```

```
cgttcgcaga attgggaatc aactgttaca tggaatgaaa cttccagaca ccgtacttta      180
gttgcatatt taaaacatgt tgagctacag caccagattc agcaattaag ctctaagcca      240
tccgcaaaaa tgacctctta tcaaaaggag caattaaagg tactctctaa tcctgacctg      300
ttggagtttg cttccggtct ggttcgcttt gaagctcgaa ttaaaacgcg atatttgaag      360
tctttcgggc ttcctcttaa tcttttgat gcaatccgct ttgcttctga ctataatagt       420
cagggtaaag acctgatttt tgatttatgg tcattctcgt tttctgaact gtttaaagca      480 tttgagggg attcaatgaa tatttatgac gattccgcag tattggacgc tatccagtct       540
aaacatttta ctattacccc ctctggcaaa acttcttttg caaaagcctc tcgctatttt      600
ggtttttatc gtcgtctggt aaacgagggt tatgatagtg ttgctcttac tatgcctcgt      660
aattcctttt ggcgttatgt atctgcatta gttgaatgtg gtattcctaa atctcaactg      720
atgaatcttt ctacctgtaa taatgttgtt ccgttagttc gttttattaa cgtagatttt      780
tcttcccaac gtcctgactg gtataatgag ccagttctta aaatcgcata aggtaattca      840
caatgattaa agttgaaatt aaaccatctc aagcccaatt tactactcgt tctggtgttt      900
ctcgtcaggg caagcctat tcactgaatg agcagctttg ttacgttgat ttgggtaatg       960
aatatccggt tcttgtcaag attactcttg atgaaggtca gccagcctat gcgcctggtc      1020
tgtacaccgt tcatctgtcc tcttttcaaag ttggtcagtt cggttccctt atgattgacc     1080
gtctgcgcct cgttccggct aagtaacatg gagcaggtcg cggatttcga cacaatttat     1140
caggcgatga tacaaatctc cgttgtactt tgtttcgcgc ttggtataat cgctgggggt     1200
caaagatgag tgttttagtg tattcttttcg cctctttcgt tttaggttgg tgccttcgta    1260
gtggcattac gtattttacc cgtttaatgg aaacttcctc atgaaaaagt ctttagtcct     1320
caaagcctct gtagccgttg ctaccctcgt tccgatgctg tctttcgctg ctgagggtga     1380
cgatcccgca aaagcggcct ttaactccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaccga tacaattaaa ggctcctttt ggagcctttt    1560
tttttggaga ttttcaacat gaaaaaatta ttattcgcaa ttcctttagt tgttcctttc   1620
tattctcact ccgctgaaac tgttgaaagt tgtttagcaa accccatac agaaaattca    1680 tttactaacg tctggaaaga cgacaaaact ttagatcgtt acgctaacta tgagggttgt    1740
ctgtggaatg ctacaggcgt tgtagtttgt actggtgacg aaactcagtg ttacggtaca    1800
tgggttccta ttgggcttgc tatccctgaa aatgagggtg gtggctctga gggtggcggt    1860
tctgagggtg gcggttctga gggtggcggt actaaacctc ctgagtacgg tgatacacct    1920
attccgggct atacttatat caaccctctc gacggcactt atccgcctgg tactgagcaa    1980
aaccccgcta atcctaatcc ttctcttgag gagtctcagc ctcttaatac tttcatgttt    2040
cagaataata ggttccgaaa taggcagggg gcattaactg tttatacggg cactgttact   2100
caaggcactg acccgttaa aacttattac cagtacactc ctgtatcatc aaaagccatg    2160
tatgacgctt actggaacgg taaattcaga gactgcgctt ccattctgg ctttaatgag    2220 gatccattcg tttgtgaata tcaaggccaa tcgtctgacc tgcctcaacc tcctgtcaat    2280
gctggcggcg gctctggtgg tggttctggt ggcggctctg agggtggtgg ctctgagggt    2340
ggcggttctg agggtggcgg ctctgaggga ggcggttccg gtggtggctc tggttccggt    2400
gattttgatt atgaaaagat ggcaaacgct aataagggg ctatgaccga aaatgccgat     2460
gaaaacgcgc tacagtctga cgctaaaggc aaacttgatt ctgtcgctac tgattacggt    2520
```

-continued

```
gctgctatcg atggtttcat tggtgacgtt tccggccttg ctaatggtaa tggtgctact      2580
ggtgattttg ctggctctaa ttcccaaatg gctcaagtcg gtgacggtga taattcacct      2640
ttaatgaata atttccgtca atatttacct tccctccctc aatcggttga atgtcgccct      2700
tttgtcttta gcgctggtaa accatatgaa ttttctattg attgtgacaa ataaacttta      2760
ttccgtggtg tctttgcgtt tcttttatat gttgccacct ttatgtatgt attttctacg      2820
tttgctaaca tactgcgtaa taaggagtct taatcatgcc agttcttttg ggtattccgt      2880
tattattgcg tttcctcggt ttccttctgg taactttgtt cggctatctg cttacttttc      2940
ttaaaaaggg cttcggtaag atagctattg ctatttcatt gtttcttgct cttattattg      3000
ggcttaactc aattcttgtg ggttatctct ctgatattag cgctcaatta ccctctgact      3060
ttgttcaggg tgttcagtta attctcccgt ctaatgcgct tccctgtttt tatgttattc      3120
tctctgtaaa ggctgctatt ttcatttttg acgttaaaca aaaaatcgtt tcttatttgg      3180
attgggataa ataatatggc tgtttatttt gtaactggca aattaggctc tggaaagacg      3240
ctcgttagcg ttggtaagat tcaggataaa attgtagctg ggtgcaaaat agcaactaat      3300
cttgatttaa ggcttcaaaa cctcccgcaa gtcgggaggt tcgctaaaac gcctcgcgtt      3360
cttagaatac cggataagcc ttctatatct gatttgcttg ctattgggcg cggtaatgat      3420
tcctacgatg aaaataaaaa cggcttgctt gttctcgatg agtgcggtac ttggtttaat      3480
acccgttctt ggaatgataa ggaaagacag ccgattattg attggtttct acatgctcgt      3540
aaattaggat gggatattat ttttcttgtt caggacttat ctattgttga taaacaggcg      3600
cgttctgcat tagctgaaca tgttgtttat tgtcgtcgtc tggacagaat tactttacct      3660
tttgtcggta ctttatattc tcttattact ggctcgaaaa tgcctctgcc taaattacat      3720
gttggcgttg ttaaatatgg cgattctcaa ttaagcccta ctgttgagcg ttggctttat      3780
actggtaaga atttgtataa cgcatatgat actaaacagg ctttttctag taattatgat      3840
tccggtgttt attcttattt aacgccttat ttatcacacg gtcggtattt caaaccatta      3900
aatttaggtc agaagatgaa attaactaaa atatatttga aaaagttttc tcgcgttctt      3960
tgtcttgcga ttggatttgc atcagcattt acatatagtt atataaccca acctaagccg      4020
gaggttaaaa aggtagtctc tcagacctat gattttgata aattcactat tgactcttct      4080
cagcgtctta atctaagcta tcgctatgtt ttcaaggatt ctaagggaaa attaattaat      4140
agcgacgatt tacagaagca aggttattca ctcacatata ttgatttatg tactgtttcc      4200
attaaaaaag gtaattcaaa tgaaattgtt aaatgtaatt aattttgttt tcttgatgtt      4260
tgtttcatca tcttcttttg ctcaggtaat tgaaatgaat aattcgcctc tgcgcgattt      4320
tgtaacttgg tattcaaagc aatcaggcga atccgttatt gtttctcccg atgtaaaagg      4380
tactgttact gtatattcat ctgacgttaa acctgaaaat ctacgcaatt tctttatttc      4440
tgttttacgt gctaataatt ttgatatggt tggttcaatt ccttccataa ttcagaagta      4500
taatccaaac aatcaggatt atattgatga attgccatca tctgataatc aggaatatga      4560
tgataattcc gctccttctg gtggtttctt tgttccgcaa aatgataatg ttactcaaac      4620
ttttaaaatt aataacgttc gggcaaagga tttaatacga gttgtcgaat gtttgtaaa       4680 gtctaatact tctaaatcct caaatgtatt atctattgac ggctctaatc tattagttgt      4740
tagtgcacct aaagatattt tagataacct tcctcaattc ctttctactg ttgatttgcc      4800
aactgaccag atattgattg agggtttgat atttgaggtt cagcaaggtg atgctttaga      4860
tttttcattt gctgctggct ctcagcgtgg cactgttgca ggcggtgtta atactgaccg      4920
```

```
cctcacctct gttttatctt ctgctggtgg ttcgttcggt atttttaatg gcgatgtttt    4980
agggctatca gttcgcgcat taaagactaa tagccattca aaatattgt ctgtgccacg     5040 tattcttacg ctttcaggtc agaagggttc tatctctgtt ggccagaatg tccctttat    5100 tactggtcgt gtgactggtg aatctgccaa tgtaaataat ccatttcaga cgattgagcg    5160
tcaaaatgta ggtatttcca tgagcgtttt tcctgttgca atggctggcg gtaatattgt    5220
tctggatatt accagcaagg ccgatagttt gagttcttct actcaggcaa gtgatgttat    5280
tactaatcaa agaagtattg ctacaacggt taatttgcgt gatggacaga ctctttact     5340 cggtggcctc actgattata aaacacttc tcaagattct ggcgtaccgt tcctgtctaa     5400
aatcccttta atcggcctcc tgtttagctc ccgctctgat tccaacgagg aaagcacgtt    5460
atacgtgctc gtcaaagcaa ccatagtacg cgccctgtag cggcgcatta agcgcggcgg    5520
gtgtggtggt tacgcgcagc gtgaccgcta cacttgccag cgccctagcg cccgctcctt    5580
tcgctttctt cccttccttt ctcgccacgt tcgccggctt tccccgtcaa gctctaaatc    5640
gggggctccc tttagggttc cgatttagtg ctttacggca cctcgacccc aaaaaacttg    5700
atttgggtga tggttcacgt agtgggccat cgccctgata dacggttttt cgccctttga    5760
cgttggagtc acgttctttt aatagtggac tcttgttcca aactggaaca acactcaacc    5820
ctatctcggg ctattctttt gatttataag gattttgcc gatttcggcc tattggttaa    5880
aaaatgagct gatttaacaa aaatttaacg cgaattttaa caaaatatta cgtttacaa    5940 tttaaatatt tgcttataca atcttcctgt ttttggggct tttctgatta tcaaccgggg    6000
tacatatgat tgacatgcta gttttacgat taccgttcat cgattctctt gtttgctcca    6060
gactctcagg caatgacctg atagcctttg tagacctctc aaaaatagct accctctccg    6120
gcatgaattt atcagctaga acggttgaat atcatattga tggtgatttg actgtctccg    6180
gcctttctca ccctttgaa tctttaccta cacattactc aggcattgca tttaaaatat    6240
atgagggttc taaaaatttt tatccttgcg ttgaaataaa ggcttctccc gcaaaagtat    6300
tacagggtca taatgttttt ggtacaaccg atttagcttt atgctctgag gctttattgc    6360
ttaattttgc taattctttg ccttgcctgt atgatttatt ggatgtt                 6407
```

<210> SEQ ID NO 2
<211> LENGTH: 410
<212> TYPE: PRT
<213> ORGANISM: M13 phage

<400> SEQUENCE: 2

Met Ile Asp Met Leu Val Leu Arg Leu Pro Phe Ile Asp Ser Leu Val
1               5                   10                  15

Cys Ser Arg Leu Ser Gly Asn Asp Leu Ile Ala Phe Val Asp Leu Ser
            20                  25                  30

Lys Ile Ala Thr Leu Ser Gly Met Asn Leu Ser Ala Arg Thr Val Glu
        35                  40                  45

Tyr His Ile Asp Gly Asp Leu Thr Val Ser Gly Leu Ser His Pro Phe
    50                  55                  60

Glu Ser Leu Pro Thr His Tyr Ser Gly Ile Ala Phe Lys Ile Tyr Glu
65                  70                  75                  80

Gly Ser Lys Asn Phe Tyr Pro Cys Val Glu Ile Lys Ala Ser Pro Ala
                85                  90                  95

Lys Val Leu Gln Gly His Asn Val Phe Gly Thr Thr Asp Leu Ala Leu
            100                 105                 110

```
Cys Ser Glu Ala Leu Leu Asn Phe Ala Asn Ser Leu Pro Cys Leu
            115                 120                 125

Tyr Asp Leu Leu Asp Val Asn Ala Thr Thr Ile Ser Arg Ile Asp Ala
130                 135                 140

Thr Phe Ser Ala Arg Ala Pro Asn Glu Asn Ile Ala Lys Gln Val Ile
145                 150                 155                 160

Asp His Leu Arg Asn Val Ser Asn Gly Gln Thr Lys Ser Thr Arg Ser
                165                 170                 175

Gln Asn Trp Glu Ser Thr Val Thr Trp Asn Gly Thr Ser Arg His Arg
            180                 185                 190

Thr Leu Val Ala Tyr Leu Lys His Val Glu Leu Gln His Gln Ile Gln
        195                 200                 205

Gln Leu Ser Ser Lys Pro Ser Ala Lys Met Thr Ser Tyr Gln Lys Glu
    210                 215                 220

Gln Leu Lys Val Leu Ser Asn Pro Asp Leu Leu Glu Phe Ala Ser Gly
225                 230                 235                 240

Leu Val Arg Phe Glu Ala Arg Ile Lys Thr Arg Tyr Leu Lys Ser Phe
                245                 250                 255

Gly Leu Pro Leu Asn Leu Phe Asp Ala Ile Arg Phe Ala Ser Asp Tyr
            260                 265                 270

Asn Ser Gln Gly Lys Asp Leu Ile Phe Asp Leu Trp Ser Phe Ser Phe
        275                 280                 285

Ser Glu Leu Phe Lys Ala Phe Glu Gly Asp Ser Met Asn Ile Tyr Asp
    290                 295                 300

Asp Ser Ala Val Leu Asp Ala Ile Gln Ser Lys His Phe Thr Ile Thr
305                 310                 315                 320

Pro Ser Gly Lys Thr Ser Phe Ala Lys Ala Ser Arg Tyr Phe Gly Phe
                325                 330                 335

Tyr Arg Arg Leu Val Asn Glu Gly Tyr Asp Ser Val Ala Leu Thr Met
            340                 345                 350

Pro Arg Asn Ser Phe Trp Arg Tyr Val Ser Ala Leu Val Glu Cys Gly
        355                 360                 365

Ile Pro Lys Ser Gln Leu Met Asn Leu Ser Thr Cys Asn Asn Val Val
    370                 375                 380

Pro Leu Val Arg Phe Ile Asn Val Asp Phe Ser Ser Gln Arg Pro Asp
385                 390                 395                 400

Trp Tyr Asn Glu Pro Val Leu Lys Ile Ala
                405                 410

<210> SEQ ID NO 3
<211> LENGTH: 111
<212> TYPE: PRT
<213> ORGANISM: M13 phage

<400> SEQUENCE: 3

Met Asn Ile Tyr Asp Asp Ser Ala Val Leu Asp Ala Ile Gln Ser Lys
1               5                   10                  15

His Phe Thr Ile Thr Pro Ser Gly Lys Thr Ser Phe Ala Lys Ala Ser
            20                  25                  30

Arg Tyr Phe Gly Phe Tyr Arg Arg Leu Val Asn Glu Gly Tyr Asp Ser
        35                  40                  45

Val Ala Leu Thr Met Pro Arg Asn Ser Phe Trp Arg Tyr Val Ser Ala
    50                  55                  60

Leu Val Glu Cys Gly Ile Pro Lys Ser Gln Leu Met Asn Leu Ser Thr
65                  70                  75                  80
```

```
Cys Asn Asn Val Val Pro Leu Val Arg Phe Ile Asn Val Asp Phe Ser
                85                  90                  95

Ser Gln Arg Pro Asp Trp Tyr Asn Glu Pro Val Leu Lys Ile Ala
            100                 105                 110
```

<210> SEQ ID NO 4
<211> LENGTH: 87
<212> TYPE: PRT
<213> ORGANISM: M13 phage

<400> SEQUENCE: 4

```
Met Ile Lys Val Glu Ile Lys Pro Ser Gln Ala Gln Phe Thr Thr Arg
1               5                   10                  15

Ser Gly Val Ser Arg Gln Gly Lys Pro Tyr Ser Leu Asn Glu Gln Leu
            20                  25                  30

Cys Tyr Val Asp Leu Gly Asn Glu Tyr Pro Val Leu Val Lys Ile Thr
            35                  40                  45

Leu Asp Glu Gly Gln Pro Ala Tyr Ala Pro Gly Leu Tyr Thr Val His
50                  55                  60

Leu Ser Ser Phe Lys Val Gly Gln Phe Gly Ser Leu Met Ile Asp Arg
65                  70                  75                  80

Leu Arg Leu Val Pro Ala Lys
                85
```

<210> SEQ ID NO 5
<211> LENGTH: 33
<212> TYPE: PRT
<213> ORGANISM: M13 phage

<400> SEQUENCE: 5

```
Met Glu Gln Val Ala Asp Phe Asp Thr Ile Tyr Gln Ala Met Ile Gln
1               5                   10                  15

Ile Ser Val Val Leu Cys Phe Ala Leu Gly Ile Ile Ala Gly Gly Gln
            20                  25                  30

Arg
```

<210> SEQ ID NO 6
<211> LENGTH: 32
<212> TYPE: PRT
<213> ORGANISM: M13 phage

<400> SEQUENCE: 6

```
Met Ser Val Leu Val Tyr Ser Phe Ala Ser Phe Val Leu Gly Trp Cys
1               5                   10                  15

Leu Arg Ser Gly Ile Thr Tyr Phe Thr Arg Leu Met Glu Thr Ser Ser
            20                  25                  30
```

<210> SEQ ID NO 7
<211> LENGTH: 73
<212> TYPE: PRT
<213> ORGANISM: M13 phage

<400> SEQUENCE: 7

```
Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asn Ser Leu Gln Ala Ser Ala Thr Glu Tyr Ile Gly Tyr Ala
            35                  40                  45
```

Trp Ala Met Val Val Ile Val Gly Ala Thr Gly Ile Lys Leu
 50                  55                  60

Phe Lys Lys Phe Thr Ser Lys Ala Ser
 65                  70

<210> SEQ ID NO 8
<211> LENGTH: 424
<212> TYPE: PRT
<213> ORGANISM: M13 phage

<400> SEQUENCE: 8

Met Lys Lys Leu Leu Phe Ala Ile Pro Leu Val Val Pro Phe Tyr Ser
 1               5                   10                  15

His Ser Ala Glu Thr Val Glu Ser Cys Leu Ala Lys Pro His Thr Glu
             20                  25                  30

Asn Ser Phe Thr Asn Val Trp Lys Asp Asp Lys Thr Leu Asp Arg Tyr
         35                  40                  45

Ala Asn Tyr Glu Gly Cys Leu Trp Asn Ala Thr Gly Val Val Val Cys
 50                  55                  60

Thr Gly Asp Glu Thr Gln Cys Tyr Gly Thr Trp Val Pro Ile Gly Leu
 65                  70                  75                  80

Ala Ile Pro Glu Asn Glu Gly Gly Gly Ser Glu Gly Gly Gly Ser Glu
                 85                  90                  95

Gly Gly Gly Ser Glu Gly Gly Thr Lys Pro Pro Glu Tyr Gly Asp
             100                 105                 110

Thr Pro Ile Pro Gly Tyr Thr Tyr Ile Asn Pro Leu Asp Gly Thr Tyr
         115                 120                 125

Pro Pro Gly Thr Glu Gln Asn Pro Ala Asn Pro Asn Pro Ser Leu Glu
130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Val Asn Ala Gly Gly Gly Ser Gly
225                 230                 235                 240

Gly Gly Ser Gly Gly Gly Ser Glu Gly Gly Ser Glu Gly Gly
                245                 250                 255

Ser Glu Gly Gly Gly Ser Glu Gly Gly Ser Gly Gly Ser Gly
            260                 265                 270

Ser Gly Asp Phe Asp Tyr Glu Lys Met Ala Asn Ala Asn Lys Gly Ala
        275                 280                 285

Met Thr Glu Asn Ala Asp Glu Asn Ala Leu Gln Ser Asp Ala Lys Gly
    290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
                325                 330                 335

Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
            355                 360                 365

Ser Val Glu Cys Arg Pro Phe Val Phe Ser Ala Gly Lys Pro Tyr Glu
    370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
            420

<210> SEQ ID NO 9
<211> LENGTH: 112
<212> TYPE: PRT
<213> ORGANISM: M13 phage

<400> SEQUENCE: 9

Met Pro Val Leu Leu Gly Ile Pro Leu Leu Arg Phe Leu Gly Phe
1               5                   10                  15

Leu Leu Val Thr Leu Phe Gly Tyr Leu Leu Thr Phe Leu Lys Lys Gly
                20                  25                  30

Phe Gly Lys Ile Ala Ile Ala Ile Ser Leu Phe Leu Ala Leu Ile Ile
            35                  40                  45

Gly Leu Asn Ser Ile Leu Val Gly Tyr Leu Ser Asp Ile Ser Ala Gln
50                  55                  60

Leu Pro Ser Asp Phe Val Gln Gly Val Gln Leu Ile Leu Pro Ser Asn
65                  70                  75                  80

Ala Leu Pro Cys Phe Tyr Val Ile Leu Ser Val Lys Ala Ala Ile Phe
                85                  90                  95

Ile Phe Asp Val Lys Gln Lys Ile Val Ser Tyr Leu Asp Trp Asp Lys
            100                 105                 110

<210> SEQ ID NO 10
<211> LENGTH: 348
<212> TYPE: PRT
<213> ORGANISM: M13 phage

<400> SEQUENCE: 10

Met Ala Val Tyr Phe Val Thr Gly Lys Leu Gly Ser Gly Lys Thr Leu
1               5                   10                  15

Val Ser Val Gly Lys Ile Gln Asp Lys Ile Val Ala Gly Cys Lys Ile
                20                  25                  30

Ala Thr Asn Leu Asp Leu Arg Leu Gln Asn Leu Pro Gln Val Gly Arg
            35                  40                  45

Phe Ala Lys Thr Pro Arg Val Leu Arg Ile Pro Asp Lys Pro Ser Ile
        50                  55                  60

Ser Asp Leu Leu Ala Ile Gly Arg Gly Asn Asp Ser Tyr Asp Glu Asn
65                  70                  75                  80

Lys Asn Gly Leu Leu Val Leu Asp Glu Cys Gly Thr Trp Phe Asn Thr
                85                  90                  95

Arg Ser Trp Asn Asp Lys Glu Arg Gln Pro Ile Ile Asp Trp Phe Leu
            100                 105                 110

His Ala Arg Lys Leu Gly Trp Asp Ile Ile Phe Leu Val Gln Asp Leu
            115                 120                 125

Ser Ile Val Asp Lys Gln Ala Arg Ser Ala Leu Ala Glu His Val Val
            130                 135                 140

Tyr Cys Arg Arg Leu Asp Arg Ile Thr Leu Pro Phe Val Gly Thr Leu
145                 150                 155                 160

Tyr Ser Leu Ile Thr Gly Ser Lys Met Pro Leu Pro Lys Leu His Val
            165                 170                 175

Gly Val Val Lys Tyr Gly Asp Ser Gln Leu Ser Pro Thr Val Glu Arg
            180                 185                 190

Trp Leu Tyr Thr Gly Lys Asn Leu Tyr Asn Ala Tyr Asp Thr Lys Gln
            195                 200                 205

Ala Phe Ser Ser Asn Tyr Asp Ser Gly Val Tyr Ser Tyr Leu Thr Pro
210                 215                 220

Tyr Leu Ser His Gly Arg Tyr Phe Lys Pro Leu Asn Leu Gly Gln Lys
225                 230                 235                 240

Met Lys Leu Thr Lys Ile Tyr Leu Lys Lys Phe Ser Arg Val Leu Cys
            245                 250                 255

Leu Ala Ile Gly Phe Ala Ser Ala Phe Thr Tyr Ser Tyr Ile Thr Gln
            260                 265                 270

Pro Lys Pro Glu Val Lys Val Val Ser Gln Thr Tyr Asp Phe Asp
            275                 280                 285

Lys Phe Thr Ile Asp Ser Ser Gln Arg Leu Asn Leu Ser Tyr Arg Tyr
            290                 295                 300

Val Phe Lys Asp Ser Lys Gly Lys Leu Ile Asn Ser Asp Asp Leu Gln
305                 310                 315                 320

Lys Gln Gly Tyr Ser Leu Thr Tyr Ile Asp Leu Cys Thr Val Ser Ile
                325                 330                 335

Lys Lys Gly Asn Ser Asn Glu Ile Val Lys Cys Asn
            340                 345

<210> SEQ ID NO 11
<211> LENGTH: 426
<212> TYPE: PRT
<213> ORGANISM: M13 phage

<400> SEQUENCE: 11

Met Lys Leu Leu Asn Val Ile Asn Phe Val Phe Leu Met Phe Val Ser
1                   5                   10                  15

Ser Ser Ser Phe Ala Gln Val Ile Glu Met Asn Asn Ser Pro Leu Arg
                20                  25                  30

Asp Phe Val Thr Trp Tyr Ser Lys Gln Ser Gly Glu Ser Val Ile Val
            35                  40                  45

Ser Pro Asp Val Lys Gly Thr Val Thr Val Tyr Ser Ser Asp Val Lys
50                  55                  60

Pro Glu Asn Leu Arg Asn Phe Phe Ile Ser Val Leu Arg Ala Asn Asn
65                  70                  75                  80

Phe Asp Met Val Gly Ser Ile Pro Ser Ile Ile Gln Lys Tyr Asn Pro
            85                  90                  95

Asn Asn Gln Asp Tyr Ile Asp Glu Leu Pro Ser Ser Asn Gln Glu
            100                 105                 110

Tyr Asp Asp Asn Ser Ala Pro Ser Gly Gly Phe Phe Val Pro Gln Asn
            115                 120                 125

Asp Asn Val Thr Gln Thr Phe Lys Ile Asn Asn Val Arg Ala Lys Asp
130                 135                 140

Leu Ile Arg Val Val Glu Leu Phe Val Lys Ser Asn Thr Ser Lys Ser
145                 150                 155                 160

Ser Asn Val Leu Ser Ile Asp Gly Ser Asn Leu Leu Val Val Ser Ala
            165                 170                 175

Pro Lys Asp Ile Leu Asp Asn Leu Pro Gln Phe Leu Ser Thr Val Asp
            180                 185                 190

Leu Pro Thr Asp Gln Ile Leu Ile Glu Gly Leu Ile Phe Glu Val Gln
        195                 200                 205

Gln Gly Asp Ala Leu Asp Phe Ser Phe Ala Ala Gly Ser Gln Arg Gly
    210                 215                 220

Thr Val Ala Gly Gly Val Asn Thr Asp Arg Leu Thr Ser Val Leu Ser
225                 230                 235                 240

Ser Ala Gly Gly Ser Phe Gly Ile Phe Asn Gly Asp Val Leu Gly Leu
                245                 250                 255

Ser Val Arg Ala Leu Lys Thr Asn Ser His Ser Lys Ile Leu Ser Val
            260                 265                 270

Pro Arg Ile Leu Thr Leu Ser Gly Gln Lys Gly Ser Ile Ser Val Gly
        275                 280                 285

Gln Asn Val Pro Phe Ile Thr Gly Arg Val Thr Gly Glu Ser Ala Asn
    290                 295                 300

Val Asn Asn Pro Phe Gln Thr Ile Glu Arg Gln Asn Val Gly Ile Ser
305                 310                 315                 320

Met Ser Val Phe Pro Val Ala Met Ala Gly Gly Asn Ile Val Leu Asp
                325                 330                 335

Ile Thr Ser Lys Ala Asp Ser Leu Ser Ser Thr Gln Ala Ser Asp
            340                 345                 350

Val Ile Thr Asn Gln Arg Ser Ile Ala Thr Thr Val Asn Leu Arg Asp
        355                 360                 365

Gly Gln Thr Leu Leu Leu Gly Gly Leu Thr Asp Tyr Lys Asn Thr Ser
    370                 375                 380

Gln Asp Ser Gly Val Pro Phe Leu Ser Lys Ile Pro Leu Ile Gly Leu
385                 390                 395                 400

Leu Phe Ser Ser Arg Ser Asp Ser Asn Glu Glu Ser Thr Leu Tyr Val
                405                 410                 415

Leu Val Lys Ala Thr Ile Val Arg Ala Leu
            420                 425

<210> SEQ ID NO 12
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 12
aaggaggtaa ctcatagtg                                               19

<210> SEQ ID NO 13
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 13
aaggaaataa ctcatagtg                                               19

<210> SEQ ID NO 14
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 14
aagaaaataa ctcatagtg                                              19

<210> SEQ ID NO 15
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 15
taatacgact cactataggg agagccacca ccaccaccac cacca                 45

<210> SEQ ID NO 16
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 16
taatacgact cactataaaa aaagccacca ccaccaccac cacca                 45

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
taatacgact cactataccc                                             20

<210> SEQ ID NO 18
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 18
cccacccaaa aaaaaaaaaa aaggggggta tagtgagtcg tatta                 45

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
taatacgact cactataggg                                             20

<210> SEQ ID NO 20
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 20
cccacccaaa aaaaaaaaaa aatctcccta tagtgagtcg tatta                 45

```
<210> SEQ ID NO 21
<211> LENGTH: 45
<212> TYPE: RNA
<213> ORGANISM: Artificial Sequence
<220> FEATURE:
<223> OTHER INFORMATION: synthetic oligonucleotide

<400> SEQUENCE: 21
gcugauggcg augaaugaac acugcguuug cuggcuuuga ugaaa           45

<210> SEQ ID NO 22
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 22
cccccaaacc cccaaaaaaa aaacccaccc aaaaaaaaaa aa              42

<210> SEQ ID NO 23
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 23
cgatccgaac gcagcattta cgctgatggc gatgaatgaa cactg           45

<210> SEQ ID NO 24
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 24
cccccaaacc cccaaaaaaa aaacccaccc aaaaaaaaaa aa              42

<210> SEQ ID NO 25
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 25
aacgccagca acgcgaataa gagaatacat cgatccgaac gcagc           45

<210> SEQ ID NO 26
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 26
gctagttatt gctcagcgga aaaaaaaaaa aaccccaaa ccccc            45

<210> SEQ ID NO 27
<211> LENGTH: 17
<212> TYPE: DNA
<213> ORGANISM: Artificial Sequence
<220> FEATURE:
<223> OTHER INFORMATION: synthetic oligonucleotide
```

<400> SEQUENCE: 27
taatacgact cactata                                                    17

<210> SEQ ID NO 28
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 28
aattaaccct cactaaa                                                    17

<210> SEQ ID NO 29
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Xaa represents Gly or Ser

<400> SEQUENCE: 29

Glu Asn Leu Tyr Phe Gln Xaa
1               5

<210> SEQ ID NO 30
<211> LENGTH: 5389
<212> TYPE: DNA
<213> ORGANISM: Artificial Sequence
<220> FEATURE:
<223> OTHER INFORMATION: recombinant nucleic acid construct

<400> SEQUENCE: 30
atgattgaca tgctagtttt acgattaccg ttcatcgatt ctcttgtttg ctccagactc      60
tcaggcaatg acctgatagc ctttgtagac ctctcaaaaa tagctaccct ctccggcatg     120
aatttatcag ctagaacggt tgaatatcat gttgatggtg atttgactgt ctccggcctt     180
tctcacccct ttgaatcttt acctacacat tactcaggca ttgcatttaa aatatatgag     240
ggttctaaaa attttttatcc ttgcgttgaa ataaaggctt ctcccgcaaa agtattacag     300
ggtcataatg ttttttggtac aaccgattta gctttatgct ctgaggcttt attgcttaat     360
tttgctaatt ctttgccttg cctgtatgat ttattggatg ttaacgctac tactattagt     420
agaattgatg ccaccttttc agctcgcgcc ccaaatgaaa atatagctaa acaggttatt     480
gaccatttgc gaaatgtatc taatggtcaa actaaatcta ctcgttcgca gaattgggaa     540
tcaactgtta catggaatga aacttccaga caccgtactt tagttgcata tttaaaacat     600
gttgagctac agcaccagat tcagcaatta agctctaagc catccgcaaa aatgacctct     660
tatcaaaagg agcaattaaa ggtactctct aatcctgacc tgttggagtt tgcttccggg     720
ctggttcgct ttgaagctcg aattagaacg cgatatttga agtctttcgg gcttcctctt     780
aatcttttg atgcaatccg ctttgcttct gactataata gtcagggtaa agacctgatt     840
tttgatttat ggtcattctc gttttctgaa ctgtttaaag catttgaggg ggattcaatg     900
aatatttatg acgattccgc agtattggac gctatccagt ctaaacattt tactattacc     960
ccctctggca aaacttcttt tgcaaaagcc tctcgctatt ttggttttta tcgtcgtctg    1020
gtaaacgagg gttatgatag tgttgctctt actatgcctc gtaattcctt ttggcgttat    1080

```
gtatctgcat tagttgaatg tggtattcct aaatctcaac tgatgaatct ttctacctgt    1140
aataatgttg ttccgttagt tcgttttatt aacgtagatt tttcttccca acgtcctgac    1200
tggtataatg agccagttct taaaatcgca taaggtaatt cacaatgatt aaagttgaaa    1260
ttaaaccatc tcaagcccaa tttactactc gttctggtgt ttctcgtcag ggcaagcctt    1320
attcactgaa tgagcagctt tgttacgttg atttgggtaa tgaatatccg gttcttgtca    1380
agattactct tgatgaaggt cagccagcct atgcgcctgg tctgtacacc gttcatctgt    1440
cctctttcaa agttggtcag ttcggttccc ttatgattga ccgtctgcgc ctcgttccgg    1500
ctaagtaaca tggagcaggt cgcggatttc gacacaattt atcaggcgat gatacaaatc    1560
tccgttgtac tttgtttcgc gcttggtata atcgctgggg gtcaaagatg agtgttttag    1620
tgtattcttt cgcctctttc gttttaggtt ggtgccttcg tagtggcatt acgtatttta    1680
cccgtttaat ggaaacttcc tcatgaaaaa gtctttagtc ctcaaagcct ctgtagccgt    1740
tgctaccctc gttccgatgc tgtctttcgc tgctgagggt gacgatcccg caaaagcggc    1800
ctttaactcc ctgcaagcct cagcgaccga atatatcggt tatgcgtggg cgatggttgt    1860
tgtcattgtc ggcgcaacta tcggtatcaa gctgtttaag aaattcacct cgaaagcaag    1920
ctgataaacc gatacaatta aaggctcctt ttggagcctt tttttcgcg ccagaaggag    1980 accaagcttg catgcctgca ggtcgactct agaggatccc cgggtaccga gctcgaattc    2040
tggagatttt caacatgctc cctcaatcgg ttgaatgtcg cccttttgtc tttagcgctg    2100
gtaaaccata tgaattttct attgattgtg acaaaatgaa cttattccgt ggtgtctttg    2160 cgttctttt atatgttgcc acctttatgt atgtattttc tacgtttgct aacatactgc    2220
gtaataagga gtcttaatca tgccagttct tttgggtatt ccgttattat tgcgtttcct    2280
cggtttcctt ctggtaactt tgttcggcta tctgcttact tttcttaaaa agggcttcgg    2340
taagatagct attgctattt cattgtttct tgctcttatt attgggctta actcaattct    2400
tgtgggttat ctctctgata ttagcgctca attaccctct gactttgttc agggtgttca    2460
gttaattctc ccgtctaatg cgcttccctg tttttatgtt attctctctg taaaggctgc    2520
tattttcatt tttgacgtta acaaaaaaat cgtttcttat ttggattggg ataaataata    2580
tggctgttta ttttgtaact ggcaaattag gctctggaaa gacgctcgtt agcgttggta    2640
agattcagga taaaattgta gctgggtgca aaatagcaac taatcttgat ttaaggcttc    2700
aaaacctccc gcaagtcggg aggttcgcta aaacgcctcg cgttcttaga ataccggata    2760
agccttctat atctgatttg cttgctattg ggcgcggtaa tgattcctac gatgaaaata    2820
aaaacggctt gcttgttctc gatgagtgcg gtacttggtt taatacccgt tcttggaatg    2880
ataaggaaag acagccgatt attgattggt ttctacatgc tcgtaaatta ggatgggata    2940
ttatttttct tgttcaggac ttatctattg ttgataaaca ggcgcgttct gcattagctg    3000
aacatgttgt ttattgtcgt cgtctggaca gaattacttt accttttgtc ggtactttat    3060
attctcttat tactggctcg aaaatgcctc tgcctaaatt acatgttggc gttgttaaat    3120
atggcgattc tcaattaagc cctactgttg agcgttggct ttatactggt aagaatttgt    3180
ataacgcata tgatactaaa caggcttttt ctagtaatta tgattccggt gtttattctt    3240
atttaacgcc ttatttatca cacggtcggt atttcaaacc attaaattta ggtcagaaga    3300
tgaaattaac taaaatatat ttgaaaaagt tttctcgcgt tctttgtctt gcgattggat    3360
ttgcatcagc atttacatat agttatataa cccaacctaa gccggaggtt aaaaaggtag    3420
tctctcagac ctatgatttt gataaattca ctattgactc ttctcagcgt cttaatctaa    3480
```

```
gctatcgcta tgttttcaag gattctaagg gaaaattaat taatagcgac gatttacaga    3540
agcaaggtta ttcactcaca tatattgatt tatgtactgt ttccattaaa aaaggtaatt    3600
caaatgaaat tgttaaatgt aattaatttt gttttcttga tgtttgtttc atcatcttct    3660
tttgctcagg taattgaaat gaataattcg cctctgcgcg attttgtaac ttggtattca    3720
aagcaatcag gcgaatccgt tattgtttct cccgatgtaa aaggtactgt tactgtatat    3780
tcatctgacg ttaaacctga aaatctacgc aatttcttta tttctgtttt acgtgcaagt    3840
aattttgata tggttggttc taacccttcc attattcaga agtataatcc aaacaatcag    3900
gattatattg atgaattgcc atcatctgat aatcaggaat atgatgataa ttccgctcct    3960
tctggtggtt tctttgttcc gcaaaatgat aatgttactc aaacttttaa aattaataac    4020
gttcgggcaa aggatttaat acgagttgtc gaattgtttg taaagtctaa tacttctaaa    4080
tcctcaaatg tattatctat tgacggctct aatctattag ttgttagtgc acctaaagat    4140
attttagata accttcctca attcctttct actgttgatt tgccaactga ccagatattg    4200
attgagggtt tgatatttga ggttcagcaa ggtgatgctt tagattttc atttgctgct    4260 ggctctcagc gtggcactgt tgcaggcggt gttaatactg accgcctcac ctctgtttta    4320
tcttctgctg tggttcgtt cggtattttt aatggcgatg ttttagggct atcagttcgc    4380
gcattaaaga ctaatagcca ttcaaaaata ttgtctgtgc cacgtattct tacgctttca    4440
ggtcagaagg gttctatctt tgttggccag aatgtccctt ttattactgg tcgtgtgact    4500
ggtgaatctg ccaatgtaaa taatccattt cagacgattg agcgtcaaaa tgtaggtatt    4560
tccatgagcg ttttcctgt tgcaatggct ggcggtaata ttgttctgga tattaccagc    4620
aaggccgata gtttgagttc ttctactcag gcaagtgatg ttattactaa tcaaagaagt    4680
actgctacaa cggttaattt gcgtgatgga cagactcttt tactcggtgg cctcactgat    4740
tataaaaaca cttctcagga ttctggcgta ccgttcctgt ctaaaatccc tttaatcggc    4800
ctcctgttta gctcccgctc tgattctaac gaggaaagca cgttatacgt gctcgtcaaa    4860
gcaaccatag tacgcgccct gtagcggcgc attaagcgcg gcgggtgtgg tggttacgcg    4920
cagcgtgacc gctacacttg ccagcgccct agcgcccgct cctttcgctt tcttcccttc    4980
ctttctcgcc acgttcgccg gctttccccg tcaagctcta aatcgggggc tccctttagg    5040
gttccgattt agtgctttac ggcacctcga ccccaaaaaa cttgatttgg gtgatggttc    5100
acgtagtggg ccatcgccct gatagacggt ttttcgccct ttgacgttgg agtccacgtt    5160
ctttaatagt ggactcttgt tccaaactgg aacaacactc aaccctatct cgggctattc    5220
ttttgattta agggatttt tgccgatttc ggcctattgg ttaaaaaatg agctgattta    5280
acaaaaattt aacgcgaatt ttaacaaaat attaacgttt acaatttaaa tatttgctta    5340
tacaatcttc ctgtttttgg ggcttttctt attatcaacc ggggtacat    5389
```

<210> SEQ ID NO 31
<211> LENGTH: 4630
<212> TYPE: DNA
<213> ORGANISM: Artificial Sequence
<220> FEATURE:
<223> OTHER INFORMATION: recombinant nucleic acid construct

<400> SEQUENCE: 31

```
ggctgttttg gcggatgaga gaagattttc agcctgatac agattaaatc agaacgcaga      60
agcggtctga taaaacagaa tttgcctggc ggcagtagcg cggtggtccc acctgacccc     120
atgccgaact cagaagtgaa acgccgtagc gccgatggta gtgtggggtc tccccatgcg     180
```

```
agagtaggga actgccaggc atcaaataaa acgaaaggct cagtcgaaag actgggcctt      240
tcgttttatc tgttgtttgt cggtgaacgc tctcctgagt aggacaaatc cgccgggagc      300
ggatttgaac gttgcgaagc aacggcccgg agggtggcgg gcaggacgcc cgccataaac      360
tgccaggcat caaattaagc agaaggccat cctgacggat ggccttttg cgtttctaca       420 aactctactc tgctagcaag taaggccgac aagcttgcat gcctgcaggt cgactctaga      480
ggatccccgg gtaccgagct cgaattccct ttttttttgg agattttcaa cgtgaaaaaa      540
ttattattcg caattccttt agttgttcct ttctattctc actccgctga aactgttgaa      600
agttgtttag caaaacccca tacagaaaat tcatttacta acgtctggaa agacgacaaa      660
actttagatc gttacgctaa ctatgagggc tgtctgtgga atgctacagg cgttgtagtt      720
tgtactggtg acgaaactca gtgttacggt acatgggttc ctattgggct tgctatccct      780
gaaaatgagg gtggtggctc tgaggtggc ggttctgagg gtggcggttc tgagggtggc       840
ggtactaaac ctcctgagta cggtgataca cctattccgg gctatactta tatcaaccct      900
ctcgacggca cttatccgcc tggtactgag caaaaccccg ctaatcctaa tccttctctt      960
gaggagtctc agcctcttaa tactttcatg tttcagaata taggttccg aaataggcag      1020 ggggcattaa ctgtttatac gggcactgtt actcaaggca ctgaccccgt taaaacttat      1080
taccagtaca ctcctgtatc atcaaaagcc atgtatgacg cttactggaa cggtaaattc      1140
agagactgcg ctttccattc tggctttaat gaggatccat tcgtttgtga atatcaaggc      1200
caatcgtctg acctgcctca acctcctgtc aatgctggcg gcggctctgg tggtggttct      1260
ggtggcggct ctgagggtgg tggctctgag ggtggcggtt ctgagggtgg cggctctgag      1320
ggaggcggtt ccggtggtgg ctctggttcc ggtgattttg attatgaaaa gatggcaaac      1380
gctaataagg gggctatgac cgaaaatgcc gatgaaaacg cgctacagtc tgacgctaaa      1440
ggcaaacttg attctgtcgc tactgattac ggtgctgcta tcgatggttt cattggtgac      1500
gtttccggcc ttgctaatgg taatggtgct actggtgatt ttgctggctc taattcccaa      1560
atggctcaag tcggtgacgg tgataattca cctttaatga ataatttccg tcaatattta      1620
ccttccctcc ctcaatcggt tgaatgtcgc cctttgtct tggcgctgg taaaccatat       1680 gaattttcta ttgattgtga caaaataaac ttattccgtg gtgtctttgc gtttctttta      1740
tatgttgcca cctttatgta tgtatttttct acgtttgcta acatactgcg taataaggag      1800
tcttaatcat gccagttcta gcataaccccc ttggggcctc taaacgggtc ttgaggggtt      1860
ttttgccttg tcggccttac ttgctaaata cattcaaata tgtatccgct catgagacaa      1920
taaccctgat aaatgcttca ataatattga aaaggaaga gtatgagtat tcaacatttc      1980
cgtgtcgccc ttattccctt ttttgcggca ttttgccttc ctgtttttgc tcacccagaa      2040
acgctggtga agtaaaaga tgctgaagat cagttgggtg cacgagtggg ttacatcgaa      2100
ctggatctca acagcggtaa gatccttgag agttttcgcc ccgaagaacg ttttccaatg      2160
atgagcactt ttaaagttct gctatgtggc gcggtattat cccgtattga cgccgggcaa      2220
gagcaactcg gtcgccgcat acactattct cagaatgact tggttgagta ctcaccagtc      2280
acagaaaagc atcttacgga tggcatgaca gtaagagaat tatgcagtgc tgccataacc      2340
atgagtgata acactgcggc caacttactt ctgacaacga tcggaggacc gaaggagcta      2400
accgcttttt tgcacaacat gggggatcat gtaactcgcc ttgatcgttg ggaaccggag      2460
ctgaatgaag ccataccaaa cgacgagcgt gacaccacga tgcctgtagc aatggcaaca      2520
acgttgcgca aactattaac tggcgaacta cttactctag cttcccggca acaattgata      2580
```

```
gactggatgg aggcggataa agttgcagga ccacttctgc gctcggccct tccggctggc    2640
tggtttattg ctgataaatc tggagccggt gagcgtggct ctcgcggtat cattgcagca    2700
ctggggccag atggtaagcc ctcccgtatc gtagttatct acacgacggg gagtcaggca    2760
actatggatg aacgaaatag acagatcgct gagataggtg cctcactgat taagcattgg    2820
taagaacctc agatccttcc gtgatggtaa cttcactagt ttaaaggat ctaggtgaag     2880 atccttttg ataatctcat gaccaaaatc ccttaacgtg agttttcgtt ccactgagcg     2940
tcagagaacc tcagatcctt ccgtatttag ccagtatgtt ctctagtgtg gttcgttgtt    3000
tttgcgtgag ccatgagaac gaaccattga gatcatgctt actttgcatg tcactcaaaa    3060
attttgcctc aaaactggtg agctgaattt ttgcagttaa agcatcgtgt agtgtttttc    3120
ttagtccgtt acgtaggtag gaatctgatg taatggttgt tggtattttg tcaccattca    3180 ttttatctg gttgttctca agttcggtta cgagatccat ttgtctatct agttcaactt     3240
ggaaaatcaa cgtatcagtc gggcggcctc gcttatcaac caccaatttc atattgctgt    3300
aagtgtttaa atctttactt attggtttca aacccattg gttaagcctt ttaaactcat     3360
ggtagttatt ttcaagcatt aacatgaact taaattcatc aaggctaatc tctatatttg    3420
ccttgtgagt tttcttttgt gttagttctt ttaataacca ctcataaatc ctcatagagt    3480 atttgtttc aaaagactta acatgttcca gattatattt tatgaatttt tttaactgga    3540
aaagataagg caatatctct tcactaaaaa ctaattctaa ttttttcgctt gagaacttgg   3600 catagtttgt ccactggaaa atctcaaagc ctttaaccaa aggattcctg atttccacag    3660
ttctcgtcat cagctctctg gttgctttag ctaatacacc ataagcattt tccctactga    3720
tgttcatcat ctgagcgtat tggttataag tgaacgatac cgtccgttct ttccttgtag    3780
ggttttcaat cgtggggttg agtagtgcca cacagcataa aattagcttg gtttcatgct    3840
ccgttaagtc atagcgacta atcgctagtt catttgcttt gaaaacaact aattcagaca    3900
tacatctcaa ttggtctagg tgattttaat cactatacca attgagatgg gctagtcaat    3960
gataattact agtccttttc ctttgagttg tgggtatctg taaattctgc tagacctttg    4020
ctggaaaact tgtaaattct gctagaccct ctgtaaattc cgctagacct ttgtgtgttt    4080
tttttgttta tattcaagtg gttataattt atagaataaa gaaagaataa aaaaagataa    4140
aaagaataga tccagccct gtgtataact cactacttta gtcagttccg cagtattaca     4200
aaaggatgtc gcaaacgctg tttgctcctc tacaaaacag accttaaaac cctaaaggct    4260
taagtagcac cctcgcaagc tcgggcaaat cgctgaatat tccttttgtc tccgaccatc    4320
aggcacctga gtcgctgtct ttttcgtgac attcagttcg ctgcgctcac ggctctggca    4380
gtgaatgggg gtaaatggca ctacaggcgc cttttatgga ttcatgcaag gaaactaccc    4440
ataatacaag aaaagcccgt cacgggcttc tcagggcgtt ttatggcggg tctgctatgt    4500
ggtgctatct gacttttgc tgttcagcag ttcctgccct ctgattttcc agtctgacca     4560
cttcggatta tcccgtgaca ggtcattcag actggctaat gcacccagta aggcagcggt    4620
atcatcaact                                                            4630
```

<210> SEQ ID NO 32
<211> LENGTH: 4630
<212> TYPE: DNA
<213> ORGANISM: Artificial Sequence
<220> FEATURE:
<223> OTHER INFORMATION: recombinant nucleic acid construct

```
<400> SEQUENCE: 32
ggctgttttg gcggatgaga gaagattttc agcctgatac agattaaatc agaacgcaga      60
agcggtctga taaaacagaa tttgcctggc ggcagtagcg cggtggtccc acctgacccc     120
atgccgaact cagaagtgaa acgccgtagc gccgatggta gtgtggggtc tccccatgcg     180
agagtaggga actgccaggc atcaaataaa acgaaaggct cagtcgaaag actgggcctt     240
tcgttttatc tgttgtttgt cggtgaacgc tctcctgagt aggacaaatc cgccgggagc     300
ggatttgaac gttgcgaagc aacggcccgg agggtggcgg gcaggacgcc cgccataaac     360
tgccaggcat caaattaagc agaaggccat cctgacggat ggcctttttg cgtttctaca     420
aactctactc tgctagcaag taaggccgac aagcttgcat gcctgcaggt cgactctaga     480
ggatccccgg gtaccgagct cgaattccct ttttttttgg agattttcaa cgtgaaaaaa     540
ttattattcg caattccttt agttgttcct ttctattctc actccgctga aactgttgaa     600
agttgtttag caaaccccca tacagaaaat tcatttacta acgtctggaa agacgacaaa     660
actttagatc gttacgctaa ctatgagggc tgtctgtgga atgctacagg cgttgtagtt     720
tgtactggtg acgaaactca gtgttacggt acatgggttc ctattgggct tgctatccct     780
gaaaatgagg gtggtggctc tgagggtggc ggttctgagg gtggcggttc tgagggtggc     840
ggtactaaac ctcctgagta cggtgataca cctattccgg gctatactta tcaaccctct     900
cgacggca cttatccgcc tggtactgag caaaaccccg ctaatcctaa tccttctctt     960
gaggagtctc agcctcttaa tactttcatg tttcagaata taggttccg aaataggcag    1020
ggggcattaa ctgtttatac gggcactgtt actcaaggca ctgaccccgt taaaacttat    1080
taccagtaca ctcctgtatc atcaaaagcc atgtatgacg cttactggaa cggtaaattc    1140
agagactgcg ctttccattc tggctttaat gaggatccat tcgtttgtga atatcaaggc    1200
caatcgtctg acctgcctca acctcctgtc aatgctggcg gcggctctgg tggtggttct    1260
ggtggcggct ctgagggtgg tggctctgag ggtggcggtt ctgagggtgg cggctctgag    1320
ggaggcggtt ccggtggtgg ctctggttcc ggtgattttg attatgaaaa gatggcaaac    1380
gctaataagg gggctatgac cgaaaatgcc gatgaaaacg cgctacagtc tgacgctaaa    1440
ggcaaacttg attctgtcgc tactgattac ggtgctgcta tcgatggttt cattggtgac    1500
gtttccggcc ttgctaatgg taatggtgct actggtgatt tgctggctc taattcccaa    1560
atggctcaag tcggtgacgg tgataattca cctttaatga ataatttccg tcaatattta    1620
ccttccctcc ctcaatcggt tgaatgtcgc ccttttgtct ttggcgctgg taaaccatat    1680
gaattttcta ttgattgtga caaaataaac ttattccgtg gtgtctttgc gtttcttta    1740
tatgttgcca cctttatgta tgtatttct acgtttgcta acatactgcg taataaggag    1800
tcttaatcat gccagttcta gcataaccc ttggggcctc taaacgggtc ttgaggggtt    1860
ttttgccttg tcggccttac ttgctaaata cattcaaata tgtatccgct catgagacaa    1920
taaccctgat aaatgcttca ataatattga aaaggaaga gtatgagtat tcaacatttc    1980
cgtgtcgccc ttattccctt ttttgcggca ttttgccttc ctgttttgc tcacccagaa    2040
acgctggtga agtaaaaga tgctgaagat cagttgggtg cacgagtggg ttacatcgaa    2100
ctggatctca acagcggtaa gatccttgag agttttcgcc ccgaagaacg ttttccaatg    2160
atgagcactt ttaaagttct gctatgtggc gcggtattat cccgtattga cgccgggcaa    2220
gagcaactcg gtcgccgcat acactattct cagaatgact tggttgagta ctcaccagtc    2280
acagaaaagc atcttacgga tggcatgaca gtaagagaat tatgcagtgc tgccataacc    2340
```

```
atgagtgata acactgcggc caacttactt ctgacaacga tcggaggacc gaaggagcta    2400
accgctttt  tgcacaacat gggggatcat gtaactcgcc ttgatcgttg ggaaccggag    2460
ctgaatgaag ccataccaaa cgacgagcgt gacaccacga tgcctgtagc aatggcaaca    2520
acgttgcgca aactattaac tggcgaacta cttactctag cttcccggca acaattgata    2580
gactggatgg aggcggataa agttgcagga ccacttctgc gctcggccct ccggctggc     2640
tggtttattg ctgataaatc tggagccggt gagcgtggct ctcgcggtat cattgcagca    2700
ctggggccag atggtaagcc ctcccgtatc gtagttatct acacgacggg gagtcaggca    2760
actatggatg aacgaaatag acagatcgct gagataggtg cctcactgat taagcattgg    2820
taagaacctc agatccttcc gtgatggtaa cttcactagt ttaaaaggat ctaggtgaag    2880
atcctttttg ataatctcat gaccaaaatc ccttaacgtg agttttcgtt ccactgagcg    2940
tcagagaacc tcagatcctt ccgtatttag ccagtatgtt ctctagtgtg gttcgttgtt    3000
tttgcgtgag ccatgagaac gaaccattga gatcatgctt actttgcatg tcactcaaaa    3060
attttgcctc aaaactggtg agctgaattt ttgcagttaa agcatcgtgt agtgttttc     3120
ttagtccgtt acgtaggtag gaatctgatg taatggttgt tggtattttg tcaccattca    3180
tttttatctg gttgttctca agttcggtta cgagatccat ttgtctatct agttcaactt    3240
ggaaaatcaa cgtatcagtc gggcggcctc gcttatcaac caccaatttc atattgctgt    3300
aagtgtttaa atctttactt attggtttca aaacccattg gttaagcctt ttaaactcat    3360
ggtagttatt ttcaagcatt aacatgaact taaattcatc aaggctaatc tctatatttg    3420
ccttgtgagt tttcttttgt gttagttctt ttaataacca ctcataaatc ctcatagagt    3480
atttgttttc aaaagactta acatgttcca gattatattt tatgaatttt tttaactgga    3540
aaagataagg caatatctct tcactaaaaa ctaattctaa ttttttcgctt gagaacttgg    3600
catagtttgt ccactggaaa atctcaaagc ctttaaccaa aggattcctg atttccacag    3660
ttctcgtcat cagctctctg gttgctttag ctaatacacc ataagcattt tccctactga    3720
tgttcatcat ctgagcgtat tggttataag tgaacgatac cgtccgttct ttccttgtag    3780
ggttttcaat cgtgggggttg agtagtgcca cacagcataa aattagcttg gtttcatgct    3840
ccgttaagtc atagcgacta atcgctagtt catttgcttt gaaaacaact aattcagaca    3900
tacatctcaa ttggtctagg tgattttaat cactatacca attgagatgg gctagtcaat    3960
gataattact agtcctttc  ctttgagttg tgggtatctg taaattctgc tagacctttg    4020
ctggaaaact tgtaaattct gctagaccct ctgtaaattc cgctagacct ttgtgtgttt    4080
tttttgttta tattcaagtg gttataattt atagaataaa gaaagaataa aaaagataa     4140
aaagaataga tcccagccct gtgtataact cactacttta gtcagttccg cagtattaca    4200
aaaggatgtc gcaaacgctg tttgctcctc tacaaaacag accttaaaac cctaaaggct    4260
taagtagcac cctcgcaagc tcgggcaaat cgctgaatat tccttttgtc tccgaccatc    4320
aggcacctga gtcgctgtct ttttcgtgac attcagttcg ctgcgctcac ggctctggca    4380
gtgaatgggg gtaaatggca ctacaggcgc cttttatgga ttcatgcaag gaaactaccc    4440
ataatacaag aaaagcccgt cacgggcttc tcagggcgtt ttatggcggg tctgctatgt    4500
ggtgctatct gacttttgc  tgttcagcag ttcctgccct ctgattttcc agtctgacca    4560
cttcggatta tcccgtgaca ggtcattcag actggctaat gcacccagta aggcagcggt    4620
atcatcaact                                                           4630
```

```
<210> SEQ ID NO 33
<211> LENGTH: 24
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (10)..(15)
<223> OTHER INFORMATION: N can represent A, T, G, or C

<400> SEQUENCE: 33
ttgatgaaan nnnnntttttt tttt                                          24

<210> SEQ ID NO 34
<211> LENGTH: 24
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (8)..(8)
<223> OTHER INFORMATION: N can represent A, T, G, or C
<220> FEATURE:
<221> NAME/KEY: misc_feature
<222> LOCATION: (16)..(16)
<223> OTHER INFORMATION: N can represent A, T, G, or C

<400> SEQUENCE: 34
ttgatganac cccccnttttt tttt                                          24

<210> SEQ ID NO 35
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 35
ttgatgaaag ggagattttt tttt                                           24
```

CONTINUOUS DIRECTED EVOLUTION

RELATED APPLICATION

This application is a continuation of and claims priority under 35 U.S.C. § 120 to U.S. application Ser. No. 13/996, 208, filed Aug. 20, 2013, which is a national stage filing under 35 U.S.C. § 371 of international PCT application, PCT/US2011/066747, filed Dec. 22, 2011, which claims priority under 35 U.S.C. § 119(e) to U.S. provisional patent application, U.S. Ser. No. 61/426,139, filed Dec. 22, 2010, entitled "Continuous Directed Evolution," the entire contents of each of which are incorporated herein by reference.

GOVERNMENT SUPPORT

This invention was made with government support under grant R01 GM065400 awarded by the National Institutes of Health. The government has certain rights in the invention.

BACKGROUND OF THE INVENTION

Conventional directed evolution involves discrete cycles of mutagenesis, transformation or in vitro expression, screening or selection, and gene harvesting and manipulation.[1,2] In contrast, evolution in nature occurs in a continuous, asynchronous format in which mutation, selection, and replication occur simultaneously. Although successful evolution is strongly dependent on the total number of rounds performed, [3] the labor- and time-intensive nature of discrete directed evolution cycles limit many laboratory evolution efforts to a modest number of rounds.

In contrast, continuous directed evolution has the potential to dramatically enhance the effectiveness of directed evolution efforts by enabling an enormous number of rounds of evolution to take place in a single experiment with minimal researcher time or effort. In a landmark experiment, Joyce and co-workers engineered a ribozyme self-replication cycle in vitro and used this cycle to continuously evolve a ribozyme with RNA ligase activity. This system remains the only reported example of continuous directed evolution and unfortunately cannot be easily adapted to evolve other biomolecules. [4-7]

Continuous directed evolution minimally requires (i) continuous mutagenesis of the gene(s) of interest, and (ii) continuous selective replication of genes encoding molecules with a desired activity. Several groups have developed methods to achieve continuous or rapid non-continuous cycles of mutagenesis.[8-13] For example, Church and coworkers recently developed multiplex automated genome engineering (MAGE), a system capable of generating targeted diversity in *E. coli* through automated cycles of transformation and recombination.[14] While these advances are capable of very efficiently creating gene libraries, they have not been linked to a rapid and general continuous selection, and consequently have not enabled continuous directed evolution.

SUMMARY OF THE INVENTION

Laboratory evolution has generated many biomolecules, e.g., nucleic acids and proteins, with desired properties. However, conventional laboratory evolution strategies rely on discrete mutation-selection rounds, and a single round of directed evolution typically requires days or longer with frequent intervention by a researcher, making complex evolution processes impractical to perform in the laboratory.

The present invention provides a platform that enables the continuous directed evolution of gene-encoded molecules that can be linked to protein production in a host cell, for example, in an *E. coli* cell. Some aspects of this invention provide a method of evolving a gene of interest by linking an activity of a molecule encoded by the gene of interest to the transfer of the gene of interest from cell to cell. In some embodiments, the platform includes a means of transferring a gene encoding a molecule of interest, for example, a protein or an RNA, from cell to cell. For example, the platform may include a phage genome, comprising a gene of interest, also referred to herein as a gene to be evolved, which replicates and mutates in a flow of host cells. The desired function of the gene of interest drives expression of a gene in the host cells that is essential for transfer of the gene from one cell to another, thus providing a selective advantage for those vectors in which the gene of interest has acquired a relevant gain-of-function mutation. For example, in some embodiments, a gene encoding a phage protein required for the production of infectious phage particles under the control of a conditional promoter the activity of which depends on a gene product encoded by the gene of interest. A population of transfer vectors comprising a gene of interest can continuously evolve in a flow of host cells over multiple transfer cycles, for example, multiple viral life cycles, and simultaneously be selected for a desired function of the gene of interest, or a product thereof, by predicating a step in the transfer cycle on the desired function, or product, thus conferring a competitive advantage on such mutants in the vector population.

Methods and vectors for the transfer of a gene of interest from cell to cell are well known in the art and include, for example, infection of suitable host cells with a viral vector (e.g., bacterial cells with a bacteriophage vector, mammalian cells with a retroviral vector, e.g., a vesicular stomatitis virus vector or a lentiviral vector), transfer of plasmids via bacterial conjugation, or intentional lysis of a cell comprising a gene of interest and uptake of naked DNA by a nearby cell.

In some embodiments, the evolution process is continuous, while in others, it is semi-continuous or involves discrete steps. In some embodiments, the evolution process is autonomous, or runs with only minimal human intervention, for example, by employing a system of controllers regulating the flow of cells or the rate of gene transfer between cells, or a robotic system performing multiple discrete steps or cycles of an evolution process.

The invention provides systems, methods, apparatuses, materials, cell lines, vectors, viruses, and reagents for directed continuous evolution, in which evolving genes are transferred from host cell to host cell through a modified viral life cycle in a manner that is dependent on an activity of interest. Dozens of cycles of viral replication, mutation, and selection can occur in a single day of directed continuous evolution without human intervention.

For example, in some embodiments, the invention provides systems, methods, apparatuses, materials, cell lines, vectors, viruses, and reagents for phage-assisted continuous evolution (PACE), in which evolving genes are transferred from host cell to host cell through a modified phage life cycle in a manner that is dependent on an activity of interest. In some such embodiments, a phage vector is provided that comprises a gene of interest to be evolved and is deficient in a gene required for the generation of infectious phage particles. In some embodiments, the gene required for the generation of infectious phage particles is under the control of a conditional promoter the activity of which is dependent on a desired activity of a product of the gene of interest (e.g., a protein or nucleic acid). In some embodiments, the phage vector is contacted with a population of host cells under conditions allowing for mutation of the gene of interest. A mutation in a gene of interest that confers a gain of the desired activity provides a competitive advantage over phage vectors without such a mutation or with a loss-of-function mutation, thus providing a continuous selective pressure on the mutating phage. Since phage life cycles are generally short (e.g., in the range of 10-20 minutes), a plurality of phage life cycles can occur in a single day of directed continuous evolution without human intervention.

As an example of a PACE process, T7 RNA polymerase (RNAP), a polymerase with highly specific requirements as to its promoter recognition sequence, was evolved to recognize a distinct promoter and to initiate transcripts with nucleotides other than G. See Example section below. Each of the three evolved activities emerged in less than one week of continuous evolution, and in all three cases PACE-evolved polymerase activities exceeded or were comparable to that of the wild-type T7 RNAP on the wild-type T7 promoter. By greatly accelerating laboratory evolution, PACE provides efficient solutions to intractable directed evolution problems.

This invention provides methods for continuous evolution of biomolecules, for example, of nucleic acids, of proteins, or of small molecules synthesized via a biosynthetic pathway. In some embodiments, a method is provided that includes the steps of (a) contacting a population of host cells with a population of viral vectors comprising a gene of interest, wherein the host cells are amenable to infection with the viral vector; (b) optionally, contacting the population of host cells with a mutagen; (c) incubating the population of host cells under conditions allowing for the production of viral particles, wherein cells are removed from the host cell population, and the population of host cells is replenished with fresh, uninfected host cells; and (d) isolating a mutated replication product of the viral vector, encoding an evolved gene of interest, from the population of host cells. In some embodiments, the expression of at least one viral gene required for the production of an infectious viral particle comprising a replication product of the viral vector is dependent on a function of a product, for example, a protein or nucleic acid, encoded by the gene of interest.

This invention also provides methods of phage-assisted continuous evolution (PACE) of a protein. In some embodiments, the method comprises providing a flow of host cells, for example, a flow of bacterial host cells through a lagoon, and a population of phage vectors encoding a gene of interest replicating in the flow of host cells under conditions allowing for replication and mutation of the phage genomes. In some embodiments, the host cells comprise a gene required for the generation of infectious phage under the control of a conditional promoter that is activated by a desired function of the gene of interest, thus conferring a selective advantage to phage genomes acquiring a gain-of function in the gene of interest. In some embodiments, the method includes contacting a population of bacterial host cells with a population of phage, for example, filamentous phages, such as M13 phages.

In some embodiments, a PACE method is provided in which a host cell population is contacted with a selection phage population, wherein the host cells comprise an expression construct in which expression of a gene required for the production of infectious phage is driven by a conditional promoter dependent on an activity of a gene product of the gene of interest, as described in more detail elsewhere herein. In some such embodiments, the selection phage comprises all remaining phage genes required for the generation of phage particles. For example, in some embodiments, a population of E. coli host cells comprising an expression construct, in which a nucleic acid encoding pIII is driven by a conditional promoter, is contacted with a population of M13 selection phage comprising a gene of interest and an origin of replication, and encoding pI, pII, and pIV-pX. In some such embodiments, the selection phage drives expression of the gene of interest from a phage promoter. In some such embodiments, the selection phage comprises all phage promoters of the wild-type phage, including the 3'-gIII promoter (see FIG. 16). In some embodiments, the selection phage comprises the last 180 bp of gIII, but not a full-length gIII coding sequence. In some embodiments, the host cells do not comprise a helper phage. One advantage of avoiding the use of a helper phage is that infection efficiency can be decreased in cells that express phage genes before infection. Accordingly, the use of a two-plasmid PACE vector system, comprising selection phage and accessory plasmid, is preferable, in some embodiments, over the use of a conventional, three-plasmid PACE vector system comprising a helper phage.

The invention also provides an apparatus or system for performing the continuous evolution methods provided herein. In some embodiments, the apparatus includes a lagoon holding an actively replicating population of phage vectors encoding a protein to be evolved, a population of phage host cells, an inflow, connected to a turbidostat holding fresh host cells, an outflow, and a controller regulating inflow and/or outflow. In some embodiments the flow rate through the lagoon is regulated so that the average time a host cell stays in the lagoon is longer than the phage life cycle, but shorter than the average time between cell divisions of the host cell. In some embodiments, the apparatus further comprises a vessel holding a mutagen, connected to an inflow of the lagoon. In some embodiments the apparatus further comprises a vessel holding an inducer of gene expression, connected to an inflow of the lagoon. In some embodiments, the host cell population comprises cells that harbor an accessory plasmid, as described in more detail elsewhere herein, but do not harbor a helper phage.

The invention further provides reagents for phage-assisted continuous evolution of biomolecules. In some embodiments, PACE vectors are provided, for example, a selection phage or phagemid, an accessory plasmid, a mutagenesis plasmid, and a helper plasmid. A selection phage or phagemid comprises a phage genome into which a gene of interest has been inserted, and in which a gene required for the generation of infectious phage particles is mutated, for example, by partial or complete deletion of the gene. In certain embodiments, the gene required for the generation of infectious phage particles is replaced, at least partially, with the gene of interest. The accessory plasmid includes the gene required for the generation of infectious phage under the control of a conditional promoter that is activated by a function of a gene product of the gene of interest and the helper phage or helper plasmid is provided that comprises an expression cassette for the expression of all genes required for the generation of phage particles that are not expressed from the selection phage or the accessory plasmid. In some embodiments, all genes required for the generation of infectious phage are expressed by the selection phage and the accessory plasmid, and a helper phage or plasmid is not required.

In some embodiments, a two-plasmid PACE vector system is provided, comprising a selection phage and an accessory plasmid, but no helper phage. In some such systems, the accessory plasmid comprises a gene encoding a protein required for the generation of infectious phage particles, and the selection phage provides all other phage genes required for phage particle generation, in addition to the gene of interest. Such a two-plasmid PACE vector system can be used by itself, or in combination with a mutagenesis plasmid as described elsewhere herein.

Host cells for PACE methods are also provided. In some embodiments, the host cells comprise an accessory plasmid with an expression construct in which the expression of a gene required for the generation of infectious phage, for example, pIII, is driven by a conditional promoter that is activated by a desired evolved function of the gene of interest. In some embodiments, the cells further comprise a mutagenesis plasmid for the expression of mutagenesis-inducing or -promoting genes, for example, genes of the bacterial SOS response or of proofreading-impaired DNA polymerases.

The invention also provides selection phages, viruses, or phagemids that include a gene of interest in their genome to be involved. In some embodiments, the selection phage is an M13 phage, the genome of which the pIII gene has been partially deleted and replaced with a gene of interest. In some embodiments, the selection phage comprises a wild-type M13 genome, comprising an origin of replication, all phage promoters and terminators comprised in the wild type genome (see FIG. 16 for reference), and a gene of interest inserted into the phage genome, but lacks a full-length coding region of a gene encoding a protein required for the generation of infectious phage particles. In some embodiments, the protein is pIII. In some such embodiments, the phage genome lacks a full-length pIII-encoding sequence, but comprises the 3'-fragment of gIII that comprises the promoter (see FIG. 16). In some embodiments, the 3'-fragment of gIII comprises the last 180 bases of gIII. In some embodiments, the gene of interest is a coding sequence that is cloned into the phage genome downstream of a wild type phage promoter. In some embodiments, the gene of interest does not comprise a transcriptional termination sequence, but uses a terminator of the phage genome. In some embodiments, the gene of interest is cloned into the phage genome to replace the gene or gene fragment encoding a protein required for the generation of infectious phage that is lacking in the phage genome. In some embodiments, the gene of interest is a coding nucleotide sequence cloned into an M13 selection phage downstream of the M13 promoter immediately downstream of the gVIII terminator, but upstream of the gIII 3'-promoter (see FIG. 16 for reference), in place of the nucleotide sequence encoding pIII in the wild-type M13.

The invention also provides evolved products of the inventive methodology. For example, in some embodiments, an evolved T7 RNA polymerase is provided that comprises a mutation conferring a modified substrate specificity and/or increased transcriptional activity to the evolved protein. Further, some aspects of this invention provide kits comprising reagents, vectors, cells, and/or apparatus for carrying out the methods provided herein. For example, in some embodiments, a kit for continuous directed evolution in a bacterial system is provided that includes a selection phage or phagemid; an accessory plasmid; optionally, a mutagenesis plasmid and/or a mutagen; and/or a host cell capable of producing infectious phage and amenable to phage infection. In some embodiments, a kit is provided that comprises a two-plasmid PACE vector system, as described in more detail elsewhere herein, for example, comprising a selection phage, an accessory plasmid, optionally, a mutagenesis plasmid, but no helper phage.

Other advantages, features, and uses of the invention will be apparent from the detailed description of certain non-limiting embodiments; the drawings, which are schematic and not intended to be drawn to scale; and the claims.

BRIEF DESCRIPTION OF THE DRAWINGS

(FIG. 2A) PACE in a single lagoon. Newly arrived host cells are infected with selection phage (SP) encoding library members. Functional library members induce production of pIII from the accessory plasmid (AP) and release progeny capable of infecting new host cells. Non-functional library members do not produce pIII and release only non-infectious progeny. Increased mutagenesis can be promoted by induction of the mutagenesis plasmid (MP). Host cells flow out of the lagoon on average faster than they can replicate, confining the accumulation of mutations to actively replicating SP. (FIG. 2B) Schematic of the PACE apparatus. Host E. coli cells maintained at a constant cell density are continuously fed into the lagoon by a peristaltic pump along with chemical inducers at a rate of approximately 1-4 volumes per hour.

(FIG. 3A) Linkage of three enzyme activities to pIII production and phage infectivity using three distinct APs. E. coli cells containing the accessory plasmids encoding conditionally expressed gene III (shown on the left) were transformed with kan$^r$ selection phage expressing T7 RNA polymerase (T7-RNAP), LGF2-RNAPα, or Zif268-Hin recombinase [43] and cultured for 8 hours at 37° C. The production of infectious phage was assayed by combining the resulting culture with spectinomycin-resistant recipient cells and incubating the culture at 37° C. for 90 minutes. Infected cells appear as colonies on plates containing kanamycin and spectinomycin (right). (Top panel) RNA polymerase activity leads to transcription of gene III and infection comparable to wild-type phage, while SP lacking T7 are not infectious. (Middle panel) Protein-protein interaction between a Gal11p domain tethered to a Zif268 DNA-binding domain and an LGF2a domain fused to RNA polymerase leads to increased gene III transcription and infection. (Bottom panel) Recombinase-catalyzed gene inversion induces gene III transcription and infection. (FIG. 3B) Exemplary designs of conditional promoters useful for accessory plasmids in continuous evolution methods.

(FIG. 5A) PACE schedule. (FIG. 5B) In vivo activity of T7 RNAP variants isolated from lagoon 1 at 48, 108, and 192 hours on the T7 and T3 promoters. Transcriptional activity was measured by cloning the protein-encoding regions of the T7 RNAP genes into a reporter construct in which the T7 or T3 promoter drives lacZ expression, introducing the resulting vector into *E. coli* cells, and quantifying beta-galactosidase activity spectrophotometrically. (FIG. 5C) In vivo activity of T7 RNAP variants isolated from lagoon 2. (FIG. 5D) In vitro activity of purified T7 RNAP variants from lagoons 1 and 2. Transcriptional activity was measured in vitro using a standard radioactive nucleotide incorporation assay. [36] Error bars represent the standard deviation of at least three independent assays.

(FIG. 7A) PACE schedule. (FIG. 7B) In vivo activity of T7 variants isolated at 80 hours on the T7 and $iC_6$ promoters. Assays were performed as described in FIG. 5B. (FIG. 7C) In vitro activity of a selection of purified T7 RNAP variants assayed in (FIG. 7B). Transcriptional activity was assayed as described in FIG. 5D. Error bars represent the standard deviation of at least three independent assays.

(FIG. 8A) PACE schedule. (FIG. 8B) In vivo activity of T7 RNAP variants isolated at 36 hours on the T7 and $iA_6$ promoters. Assays were performed as described in FIG. 5B. (FIG. 8C) In vitro activity of a selection of purified T7 RNAP variants assayed in (FIG. 8B). Transcriptional activity was assayed as described in FIG. 5D. Error bars represent the standard deviation of at least three independent assays.

DEFINITIONS

Continuous Evolution Concept

Figure 1A:
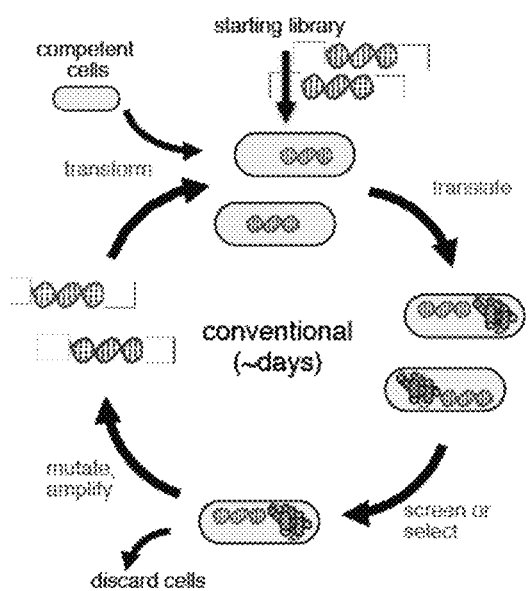
FIGS. 1A and 1B. Directed evolution cycles in (FIG. 1A) conventional directed evolution in cells and (FIG. 1B) phage-assisted continuous evolution (PACE). The conventional evolution cycle typically requires the intervention of a researcher in at least the steps of transformation, mutation/amplification, and screening/selecting, while the PACE cycle typically does not require researcher intervention.

The term "continuous evolution," as used herein, refers to an evolution procedure, in which a population of nucleic acids is subjected to multiple rounds of (a) replication, (b) mutation, and (c) selection to produce a desired evolved product, for example, a nucleic acid encoding a protein with a desired activity, wherein the multiple rounds can be performed without investigator interaction and wherein the processes under (a)-(c) can be carried out simultaneously. Typically, the evolution procedure is carried out in vitro, for example, using cells in culture as host cells. In general, a continuous evolution process provided herein relies on a system in which a gene of interest is provided in a nucleic acid vector that undergoes a life-cycle including replication in a host cell and transfer to another host cell, wherein a critical component of the life-cycle is deactivated and reactivation of the component is dependent upon a desired mutation in the gene of interest.

In some embodiments, a gene of interest is transferred from cell to cell in a manner dependent on the activity of the gene of interest. In some embodiments, the transfer vector is a virus infecting cells, for example, a bacteriophage, or a retroviral vector. In some embodiments, the viral vector is a phage vector infecting bacterial host cells. In some embodiments, the transfer vector is a retroviral vector, for example, a lentiviral vector or a vesicular stomatitis virus vector, infecting human or mouse cells. In some embodiments, the transfer vector is a conjugative plasmid transferred from a donor bacterial cell to a recipient bacterial cell.

In some embodiments, the nucleic acid vector comprising the gene of interest is a phage, a viral vector, or naked DNA (e.g., a mobilization plasmid). In some embodiments, transfer of the gene of interest from cell to cell is via infection, transfection, transduction, conjugation, or uptake of naked DNA, and efficiency of cell-to-cell transfer (e.g., transfer rate) is dependent on an activity of a product encoded by the gene of interest. For example, in some embodiments, the nucleic acid vector is a phage harboring the gene of interest and the efficiency of phage transfer (via infection) is dependent on an activity of the gene of interest in that a protein required for the generation of phage particles (e.g., pIII for M13 phage) is expressed in the host cells only in the presence of the desired activity of the gene of interest. In another example, the nucleic acid vector is a retroviral vector, for example, a lentiviral or vesicular stomatitis virus vector harboring the gene of interest, and the efficiency of viral transfer from cell to cell is dependent on an activity of the gene of interest in that a protein required for the generation of viral particles (e.g., an envelope protein, such as VSV-g) is expressed in the host cells only in the presence of the desired activity of the gene of interest. In another example, the nucleic acid vector is a DNA vector, for example, in the form of a mobilizable plasmid DNA, comprising the gene of interest, that is transferred between bacterial host cells via conjugation and the efficiency of conjugation-mediated transfer from cell to cell is dependent on an activity of the gene of interest in that a protein required for conjugation-mediated transfer (e.g., traA or traQ) is expressed in the host cells only in the presence of the desired activity of the gene of interest. Host cells contain F plasmid lacking one or both of those genes.

For example, some embodiments provide a continuous evolution system, in which a population of viral vectors comprising a gene of interest to be evolved replicates in a flow of host cells, e.g., a flow through a lagoon, wherein the viral vectors are deficient in a gene encoding a protein that is essential for the generation of infectious viral particles, and wherein that gene is comprised in the host cell under the control of a conditional promoter that can be activated by a gene product encoded by the gene of interest, or a mutated version thereof. In some embodiments, the activity of the conditional promoter depends on a desired function of a gene product encoded by the gene of interest. Viral vectors, in which the gene of interest has not acquired a mutation conferring the desired function, will not activate the conditional promoter, or only achieve minimal activation, while any mutation in the gene of interest that confers the desired mutation will result in activation of the conditional promoter. Since the conditional promoter controls an essential protein for the viral life cycle, activation of this promoter directly corresponds to an advantage in viral spread and replication for those vectors that have acquired an advantageous mutation.

The term "flow", as used herein in the context of host cells, refers to a stream of host cells, wherein fresh host cells are being introduced into a host cell population, for example, a host cell population in a lagoon, remain within the population for a limited time, and are then removed from the host cell population. In a simple form, a host cell flow may be a flow through a tube, or a channel, for example, at a controlled rate. In other embodiments, a flow of host cells is directed through a lagoon that holds a volume of cell culture media and comprises an inflow and an outflow. The introduction of fresh host cells may be continuous or intermittent and removal may be passive, e.g., by overflow, or active, e.g., by active siphoning or pumping. Removal further may be random, for example, if a stirred suspension culture of host cells is provided, removed liquid culture media will contain freshly introduced host cells as well as cells that have been a member of the host cell population within the lagoon for some time. Even though, in theory, a cell could escape removal from the lagoon indefinitely, the average host cell will remain only for a limited period of time within the lagoon, which is determined mainly by the flow rate of the culture media (and suspended cells) through the lagoon.

Since the viral vectors replicate in a flow of host cells, in which fresh, uninfected host cells are provided while infected cells are removed, multiple consecutive viral life cycles can occur without investigator interaction, which allows for the accumulation of multiple advantageous mutations in a single evolution experiment.

The term "phage-assisted continuous evolution (PACE)," as used herein, refers to continuous evolution that employs phage as viral vectors.

Viral Vectors

The term "viral vector," as used herein, refers to a nucleic acid comprising a viral genome that, when introduced into a suitable host cell, can be replicated and packaged into viral particles able to transfer the viral genome into another host cell. The term viral vector extends to vectors comprising truncated or partial viral genomes. For example, in some embodiments, a viral vector is provided that lacks a gene encoding a protein essential for the generation of infectious viral particles. In suitable host cells, for example, host cells comprising the lacking gene under the control of a conditional promoter, however, such truncated viral vectors can replicate and generate viral particles able to transfer the truncated viral genome into another host cell. In some embodiments, the viral vector is a phage, for example, a filamentous phage (e.g., an M13 phage). In some embodiments, a viral vector, for example, a phage vector, is provided that comprises a gene of interest to be evolved.

The term "nucleic acid," as used herein, refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

The term "protein," as used herein refers to a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain; see, for example, www.cco.caltech.edu/

~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term "gene of interest," as used herein, refers to a nucleic acid construct comprising a nucleotide sequence encoding a gene product of interest, for example, a gene product to be evolved in a continuous evolution process as provided herein. The term includes any variations of a gene of interest that are the result of a continuous evolution process according to methods provided herein. For example, in some embodiments, a gene of interest is a nucleic acid construct comprising a nucleotide sequence encoding a protein to be evolved, cloned into a viral vector, for example, a phage genome, so that the expression of the encoding sequence is under the control of one or more promoters in the viral genome. In other embodiments, a gene of interest is a nucleic acid construct comprising a nucleotide sequence encoding a protein to be evolved and a promoter operably linked to the encoding sequence. When cloned into a viral vector, for example, a phage genome, the expression of the encoding sequence of such genes of interest is under the control of the heterologous promoter and, in some embodiments, may also be influenced by one or more promoters comprised in the viral genome.

The term "function of a gene of interest," as interchangeably used with the term "activity of a gene of interest," refers to a function or activity of a gene product, for example, a nucleic acid, or a protein, encoded by the gene of interest. For example, a function of a gene of interest may be an enzymatic activity (e.g., an enzymatic activity resulting in the generation of a reaction product, phosphorylation activity, phosphatase activity, etc.), an ability to activate transcription (e.g., transcriptional activation activity targeted to a specific promoter sequence), a bond-forming activity, (e.g., an enzymatic activity resulting in the formation of a covalent bond), or a binding activity (e.g., a protein, DNA, or RNA binding activity).

The term "promoter" is art-recognized and refers to a nucleic acid molecule with a sequence recognized by the cellular transcription machinery and able to initiate transcription of a downstream gene. A promoter can be constitutively active, meaning that the promoter is always active in a given cellular context, or conditionally active, meaning that the promoter is only active in the presence of a specific condition. For example, a conditional promoter may only be active in the presence of a specific protein that connects a protein associated with a regulatory element in the promoter to the basic transcriptional machinery, or only in the absence of an inhibitory molecule. A subclass of conditionally active promoters are inducible promoters that require the presence of a small molecule "inducer" for activity. Examples of inducible promoters include, but are not limited to, arabinose-inducible promoters, Tet-on promoters, and tamoxifen-inducible promoters. A variety of constitutive, conditional, and inducible promoters are well known to the skilled artisan, and the skilled artisan will be able to ascertain a variety of such promoters useful in carrying out the instant invention, which is not limited in this respect.

The term "viral particle," as used herein, refers to a viral genome, for example, a DNA or RNA genome, that is associated with a coat of a viral protein or proteins, and, in some cases, with an envelope of lipids. For example, a phage particle comprises a phage genome packaged into a protein encoded by the wild type phage genome.

The term "infectious viral particle," as used herein, refers to a viral particle able to transport the viral genome it comprises into a suitable host cell. Not all viral particles are able to transfer the viral genome to a suitable host cell. Particles unable to accomplish this are referred to as a non-infectious viral particles. In some embodiments, a viral particle comprises a plurality of different coat proteins, wherein one or some of the coat proteins can be omitted without compromising the structure of the viral particle. In some embodiments, a viral particle is provided in which at least one coat protein cannot be omitted without the loss of infectivity. If a viral particle lacks a protein that confers infectivity, the viral particle is not infectious. For example, an M13 phage particle that comprises a phage genome packaged in a coat of phage proteins (e.g., pVIII) but lacks pIII (protein III) is a non-infectious M13 phage particle because pIII is essential for the infectious properties of M13 phage particles.

The term "viral life cycle," as used herein, refers to the viral reproduction cycle comprising insertion of the viral genome into a host cell, replication of the viral genome in the host cell, and packaging of a replication product of the viral genome into a viral particle by the host cell.

In some embodiments, the viral vector provided is a phage. The term "phage," as used herein interchangeably with the term "bacteriophage," refers to a virus that infects bacterial cells. Typically, phages consist of an outer protein capsid enclosing genetic material. The genetic material can be ssRNA, dsRNA, ssDNA, or dsDNA, in either linear or circular form. Phages and phage vectors are well known to those of skill in the art and non-limiting examples of phages that are useful for carrying out the methods provided herein are λ (Lysogen), T2, T4, T7, T12, R17, M13, MS2, G4, P1, P2, P4, Phi X174, N4, Φ6, and Φ29. In certain embodiments, the phage utilized in the present invention is M13. Additional suitable phages and host cells will be apparent to those of skill in the art and the invention is not limited in this aspect. For an exemplary description of additional suitable phages and host cells, see Elizabeth Kutter and Alexander Sulakvelidze: *Bacteriophages: Biology and Applications*. CRC Press; 1$^{st}$ edition (December 2004), ISBN: 0849313368; Martha R. J. Clokie and Andrew M. Kropinski: *Bacteriophages: Methods and Protocols, Volume 1: Isolation, Characterization, and Interactions (Methods in Molecular Biology)* Humana Press; 1$^{st}$ edition (December, 2008), ISBN: 1588296822; Martha R. J. Clokie and Andrew M. Kropinski: *Bacteriophages: Methods and Protocols, Volume 2: Molecular and Applied Aspects (Methods in Molecular Biology)* Humana Press; 1$^{st}$ edition (December 2008), ISBN: 1603275649; all of which are incorporated herein in their entirety by reference for disclosure of suitable phages and host cells as well as methods and protocols for isolation, culture, and manipulation of such phages).

Figure 16:
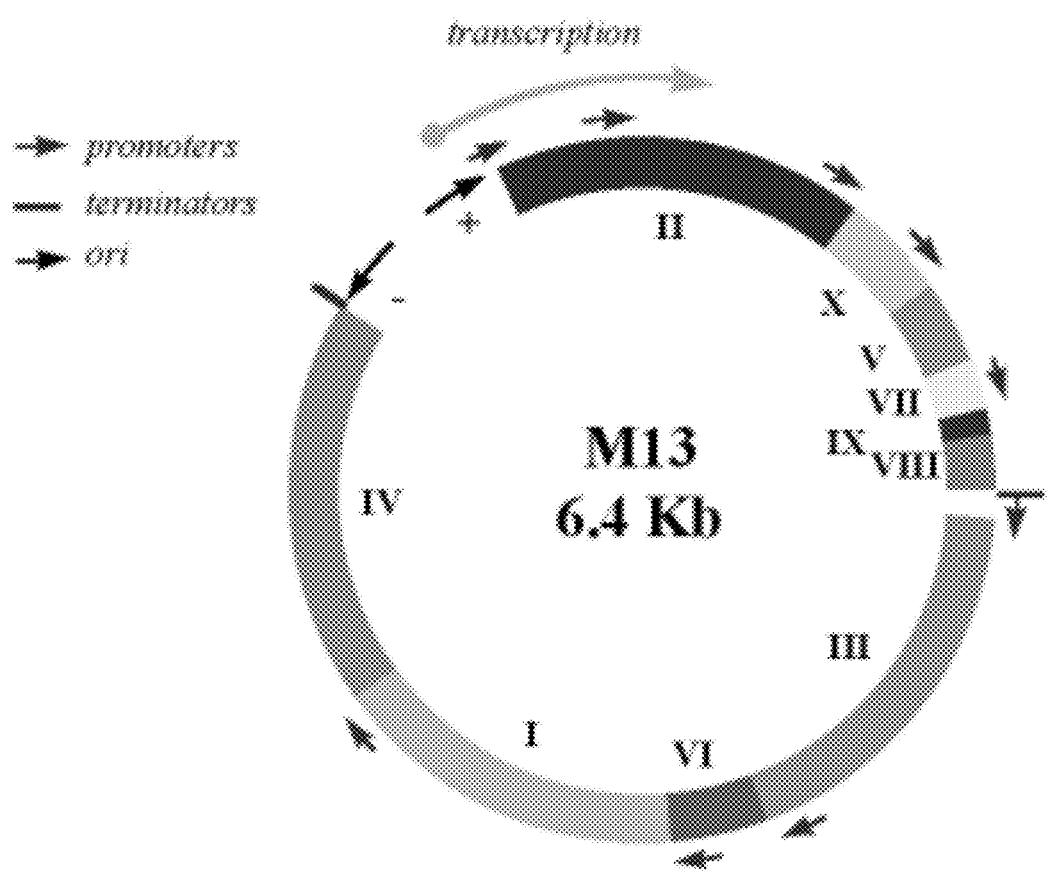
FIG. 16. Schematic illustration of an M13 phage genome. Ori: origin of replication.

In some embodiments, the phage is a filamentous phage. In some embodiments, the phage is an M13 phage. M13 phages are well known to those in the art and the biology of M13 phages has extensively been studied. A schematic representation of the wild-type M13 genome is provided in FIG. 16. Wild type M13 phage particles comprise a circular, single-stranded genome of approximately 6.4 kb. The wilt-type genome includes ten genes, gI-gX, which, in turn, encode the ten M13 proteins, pI-pX, respectively. gVIII encodes pVIII, also often referred to as the major structural protein of the phage particles, while gIII encodes pIII, also referred to as the minor coat protein, which is required for infectivity of M13 phage particles.

The M13 life cycle includes attachment of the phage to the sex pilus of a suitable bacterial host cell via the pIII protein and insertion of the phage genome into the host cell. The circular, single-stranded phage genome is then converted to a circular, double-stranded DNA, also termed the replicative form (RF), from which phage gene transcription is initiated. The wild type M13 genome comprises nine promoters and two transcriptional terminators as well as an origin of replication. This series of promoters provides a gradient of transcription such that the genes nearest the two transcriptional terminators (gVIII and IV) are transcribed at the highest levels. In wild-type M13 phage, transcription of all 10 genes proceeds in same direction. One of the phage-encode proteins, pII, initiates the generation of linear, single-stranded phage genomes in the host cells, which are subsequently circularized, and bound and stabilized by pV. The circularized, single-stranded M13 genomes are then bound by pVIII, while pV is stripped off the genome, which initiates the packaging process. At the end of the packaging process, multiple copies of pIII are attached to wild-type M13 particles, thus generating infectious phage ready to infect another host cell and concluding the life cycle.

The M13 phage genome can be manipulated, for example, by deleting one or more of the wild type genes, and/or inserting a heterologous nucleic acid construct into the genome. M13 does not have stringent genome size restrictions, and insertions of up to 42 kb have been reported. This allows M13 phage vectors to be used in continuous evolution experiments to evolve genes of interest without imposing a limitation on the length of the gene to be involved.

The M13 phage has been well characterized and the genomic sequence of M13 has been reported. Representative M13 genomic sequences can be retrieved from public databases and an exemplary sequence is provided in entry V00604 of the National Center for Biotechnology Information (NCBI) database (www.ncbi.nlm.nih.gov):

Phage M13 genome:

```
>gi|56713234|emb|V00604.2| Phage M13 genome
                                          (SEQ ID NO: 1)
AACGCTACTACTATTAGTAGAATTGATGCCACCTTTTCAGCTCGCGC

CCCAAATGAAAATATAGCTAAACAGGTTATTGACCATTTGCGAAATG

TATCTAATGGTCAAACTAAATCTACTCGTTCGCAGAATTGGGAATCA

ACTGTTACATGGAATGAAACTTCCAGACACCGTACTTTAGTTGCATA

TTTAAAACATGTTGAGCTACAGCACCAGATTCAGCAATTAAGCTCTA

AGCCATCCGCAAAAATGACCTCTTATCAAAAGGAGCAATTAAAGGTA

CTCTCTAATCCTGACCTGTTGGAGTTTGCTTCCGGTCTGGTTCGCTT

TGAAGCTCGAATTAAAACGCGATATTTGAAGTCTTTCGGGCTTCCTC

TTAATCTTTTTGATGCAATCCGCTTTGCTTCTGACTATAATAGTCAG

GGTAAAGACCTGATTTTTGATTTATGGTCATTCTCGTTTTCTGAACT

GTTTAAAGCATTTGAGGGGGATTCAATGAATATTTATGACGATTCCG

CAGTATTGGACGCTATCCAGTCTAAACATTTTACTATTACCCCCTCT

GGCAAAACTTCTTTTGCAAAAGCCTCTCGCTATTTTGGTTTTTATCG

TCGTCTGGTAAACGAGGGTTATGATAGTGTTGCTCTTACTATGCCTC

GTAATTCCTTTTGGCGTTATGTATCTGCATTAGTTGAATGTGGTATT

CCTAAATCTCAACTGATGAATCTTTCTACCTGTAATAATGTTGTTCC

GTTAGTTCGTTTTATTAACGTAGATTTTTCTTCCCAACGTCCTGACT

GGTATAATGAGCCAGTTCTTAAAATCGCATAAGGTAATTCACAATGA

TTAAAGTTGAAATTAAACCATCTCAAGCCCAATTTACTACTCGTTCT

GGTGTTTCTCGTCAGGGCAAGCCTTATTCACTGAATGAGCAGCTTTG

TTACGTTGATTTGGGTAATGAATATCCGGTTCTTGTCAAGATTACTC

TTGATGAAGGTCAGCCAGCCTATGCGCCTGGTCTGTACACCGTTCAT

CTGTCCTCTTTCAAAGTTGGTCAGTTCGGTTCCCTTATGATTGACCG

TCTGCGCCTCGTTCCGGCTAAGTAACATGGAGCAGGTCGCGGATTTC

GACACAATTTATCAGGCGATGATACAAATCTCCGTTGTACTTTGTTT

CGCGCTTGGTATAATCGCTGGGGGTCAAAGATGAGTGTTTTAGTGTA

TTCTTTCGCCTCTTTCGTTTTAGGTTGGTGCCTTCGTAGTGGCATTA

CGTATTTTACCCGTTTAATGGAAACTTCCTCATGAAAAAGTCTTTAG

TCCTCAAAGCCTCTGTAGCCGTTGCTACCCTCGTTCCGATGCTGTCT

TTCGCTGCTGAGGGTGACGATCCCGCAAAAGCGGCCTTTAACTCCCT

GCAAGCCTCAGCGACCGAATATATCGGTTATGCGTGGGCGATGGTTG

TTGTCATTGTCGGCGCAACTATCGGTATCAAGCTGTTTAAGAAATTC

ACCTCGAAAGCAAGCTGATAAACCGATACAATTAAAGGCTCCTTTTG

GAGCCTTTTTTTTGGAGATTTTCAACATGAAAAAATTATTATTCGC

AATTCCTTTAGTTGTTCCTTTCTATTCTCACTCCGCTGAAACTGTTG

AAAGTTGTTTAGCAAAACCCCATACAGAAAATTCATTTACTAACGTC

TGGAAAGACGACAAAACTTTAGATCGTTACGCTAACTATGAGGGTTG

TCTGTGGAATGCTACAGGCGTTGTAGTTTGTACTGGTGACGAAACTC

AGTGTTACGGTACATGGGTTCCTATTGGGCTTGCTATCCCTGAAAAT

GAGGGTGGTGGCTCTGAGGGTGGCGGTTCTGAGGGTGGCGGTTCTGA

GGGTGGCGGTACTAAACCTCCTGAGTACGGTGATACACCTATTCCGG

GCTATACTTATATCAACCCTCTCGACGGCACTTATCCGCCTGGTACT

GAGCAAAACCCCGCTAATCCTAATCCTTCTCTTGAGGAGTCTCAGCC

TCTTAATACTTTCATGTTTCAGAATAATAGGTTCCGAAATAGGCAGG

GGGCATTAACTGTTTATACGGGCACTGTTACTCAAGGCACTGACCCC

GTTAAAACTTATTACCAGTACACTCCTGTATCATCAAAAGCCATGTA

TGACGCTTACTGGAACGGTAAATTCAGAGACTGCGCTTTCCATTCTG

GCTTTAATGAGGATCCATTCGTTTGTGAATATCAAGGCCAATCGTCT

GACCTGCCTCAACCTCCTGTCAATGCTGGCGGCGGCTCTGGTGGTGG

TTCTGGTGGCGGCTCTGAGGGTGGTGGCTCTGAGGGTGGCGGTTCTG

AGGGTGGCGGCTCTGAGGGAGGCGGTTCCGGTGGTGGCTCTGGTTCC

GGTGATTTTGATTATGAAAGATGGCAAACGCTAATAAGGGGGCTAT

GACCGAAAATGCCGATGAAAACGCGCTACAGTCTGACGCTAAAGGCA
```

-continued

```
AACTTGATTCTGTCGCTACTGATTACGGTGCTGCTATCGATGGTTTC
ATTGGTGACGTTTCCGGCCTTGCTAATGGTAATGGTGCTACTGGTGA
TTTTGCTGGCTCTAATTCCCAAATGGCTCAAGTCGGTGACGGTGATA
ATTCACCTTTAATGAATAATTTCCGTCAATATTTACCTTCCCTCCCT
CAATCGGTTGAATGTCGCCCTTTTGTCTTTAGCGCTGGTAAACCATA
TGAATTTTCTATTGATTGTGACAAAATAAACTTATTCCGTGGTGTCT
TTGCGTTTCTTTTATATGTTGCCACCTTTATGTATGTATTTTCTACG
TTTGCTAACATACTGCGTAATAAGGAGTCTTAATCATGCCAGTTCTT
TTGGGTATTCCGTTATTATTGCGTTTCCTCGGTTTCCTTCTGGTAAC
TTTGTTCGGCTATCTGCTTACTTTTCTTAAAAAGGGCTTCGGTAAGA
TAGCTATTGCTATTTCATTGTTTCTTGCTCTTATTATTGGGCTTAAC
TCAATTCTTGTGGGTTATCTCTCTGATATTAGCGCTCAATTACCCTC
TGACTTTGTTCAGGGTGTTCAGTTAATTCTCCCGTCAATGCGCTTC
CCTGTTTTTATGTTATTCTCTCTGTAAAGGCTGCTATTTTCATTTTT
GACGTTAAACAAAAAATCGTTTCTTATTTGGATTGGGATAAATAATA
TGGCTGTTTATTTTGTAACTGGCAAATTAGGCTCTGGAAAGACGCTC
GTTAGCGTTGGTAAGATTCAGGATAAAATTGTAGCTGGGTGCAAAAT
AGCAACTAATCTTGATTTAAGGCTTCAAAACCTCCCGCAAGTCGGGA
GGTTCGCTAAAACGCCTCGCGTTCTTAGAATACCGGATAAGCCTTCT
ATATCTGATTTGCTTGCTATTGGGCGCGGTAATGATTCCTACGATGA
AAATAAAAACGGCTTGCTTGTTCTCGATGAGTGCGGTACTTGGTTTA
ATACCCGTTCTTGGAATGATAAGGAAAGACAGCCGATTATTGATTGG
TTTCTACATGCTCGTAAATTAGGATGGGATATTATTTTTCTTGTTCA
GGACTTATCTATTGTTGATAAACAGGCGCGTTCTGCATTAGCTGAAC
ATGTTGTTTATTGTCGTCGTCTGGACAGAATTACTTTACCTTTTGTC
GGTACTTTATATTCTCTTATTACTGGCTCGAAAATGCCTCTGCCTAA
ATTACATGTTGGCGTTGTTAAATATGGCGATTCTCAATTAAGCCCTA
CTGTTGAGCGTTGGCTTTATACTGGTAAGAATTTGTATAACGCATAT
GATACTAAACAGGCTTTTTCTAGTAATTATGATTCCGGTGTTTATTC
TTATTTAACGCCTTATTTATCACACGGTCGGTATTTCAAACCATTAA
ATTTAGGTCAGAAGATGAAATTAACTAAAATATATTTGAAAAAGTTT
TCTCGCGTTCTTTGTCTTGCGATTGGATTTGCATCAGCATTTACATA
TAGTTATATAACCCAACCTAAGCCGGAGGTTAAAAAGGTAGTCTCTC
AGACCTATGATTTTGATAAATTCACTATTGACTCTTCTCAGCGTCTT
AATCTAAGCTATCGCTATGTTTTCAAGGATTCTAAGGGAAAATTAAT
TAATAGCGACGATTTACAGAAGCAAGGTTATTCACTCACATATATTG
ATTTATGTACTGTTTCCATTAAAAAAGGTAATTCAAATGAAATTGTT
AAATGTAATTAATTTTGTTTTCTTGATGTTTGTTTCATCATCTTCTT
TTGCTCAGGTAATTGAAATGAATAATTCGCCTCTGCGCGATTTTGTA
ACTTGGTATTCAAAGCAATCAGGCGAATCCGTTATTGTTTCTCCCGA
TGTAAAAGGTACTGTTACTGTATATTCATCTGACGTTAAACCTGAAA
```

-continued

```
ATCTACGCAATTTCTTTATTTCTGTTTTACGTGCTAATAATTTTGAT
ATGGTTGGTTCAATTCCTTCCATAATTCAGAAGTATAATCCAAACAA
TCAGGATTATATTGATGAATTGCCATCATCTGATAATCAGGAATATG
ATGATAATTCCGCTCCTTCTGGTGGTTTCTTTGTTCCGCAAATGAT
AATGTTACTCAAACTTTTAAAATTAATAACGTTCGGGCAAAGGATTT
AATACGAGTTGTCGAATTGTTTGTAAAGTCTAATACTTCTAAATCCT
CAAATGTATTATCTATTGACGGCTCTAATCTATTAGTTGTTAGTGCA
CCTAAAGATATTTTAGATAACCTTCCTCAATTCCTTTCTACTGTTGA
TTTGCCAACTGACCAGATATTGATTGAGGGTTTGATATTTGAGGTTC
AGCAAGGTGATGCTTTAGATTTTTCATTTGCTGCTGGCTCTCAGCGT
GGCACTGTTGCAGGCGGTGTTAATACTGACCGCCTCACCTCTGTTTT
ATCTTCTGCTGGTGGTTCGTTCGGTATTTTTAATGGCGATGTTTTAG
GGCTATCAGTTCGCGCATTAAAGACTAATAGCCATTCAAAAATATTG
TCTGTGCCACGTATTCTTACGCTTTCAGGTCAGAAGGGTTCTATCTC
TGTTGGCCAGAATGTCCCTTTTATTACTGGTCGTGTGACTGGTGAAT
CTGCCAATGTAAATAATCCATTTCAGACGATTGAGCGTCAAAATGTA
GGTATTTCCATGAGCGTTTTTCCTGTTGCAATGGCTGGCGGTAATAT
TGTTCTGGATATTACCAGCAAGGCCGATAGTTTGAGTTCTTCTACTC
AGGCAAGTGATGTTATTACTAATCAAAGAAGTATTGCTACAACGGTT
AATTTGCGTGATGGACAGACTCTTTTACTCGGTGGCCTCACTGATTA
TAAAAACACTTCTCAAGATTCTGGCGTACCGTTCCTGTCTAAAATCC
CTTTAATCGGCCTCCTGTTTAGCTCCCGCTCTGATTCCAACGAGGAA
AGCACGTTATACGTGCTCGTCAAAGCAACCATAGTACGCGCCCTGTA
GCGGCGCATTAAGCGCGGCGGGTGTGGTGGTTACGCGCAGCGTGACC
GCTACACTTGCCAGCGCCCTAGCGCCCGCTCCTTTCGCTTTCTTCCC
TTCCTTTCTCGCCACGTTCGCCGGCTTTCCCCGTCAAGCTCTAAATC
GGGGGCTCCCTTTAGGGTTCCGATTTAGTGCTTTACGGCACCTCGAC
CCCAAAAAACTTGATTTGGGTGATGGTTCACGTAGTGGGCCATCGCC
CTGATAGACGGTTTTTCGCCCTTTGACGTTGGAGTCCACGTTCTTTA
ATAGTGGACTCTTGTTCCAAACTGGAACAACACTCAACCCTATCTCG
GGCTATTCTTTTGATTTATAAGGGATTTTGCCGATTTCGGCCTATTG
GTTAAAAAATGAGCTGATTTAACAAAAATTTAACGCGAATTTTAACA
AAATATTAACGTTTACAATTTAAATATTTGCTTATACAATCTTCCTG
TTTTTGGGGCTTTTCTGATTATCAACCGGGGTACATATGATTGACAT
GCTAGTTTACGATTACCGTTCATCGATTCTCTTGTTTGCTCCAGAC
TCTCAGGCAATGACCTGATAGCCTTTGTAGACCTCTCAAAAATAGCT
ACCCTCTCCGGCATGAATTTATCAGCTAGAACGGTTGAATATCATAT
TGATGGTGATTTGACTGTCTCCGGCCTTTCTCACCCTTTTGAATCTT
TACCTACACATTACTCAGGCATTGCATTTAAAATATATGAGGGTTCT
AAAAATTTTTATCCTTGCGTTGAAATAAAGGCTTCTCCCGCAAAAGT
ATTACAGGGTCATAATGTTTTTGGTACAACCGATTTAGCTTTATGCT
```

```
CTGAGGCTTTATTGCTTAATTTTGCTAATTCTTTGCCTTGCCTGTAT

GATTTATTGGATGTT
```

GENE II: join (6006..6407,1..831)

(SEQ ID NO: 2)
```
translation=MIDMLVLRLPFIDSLVCSRLSGNDLIAFVDLSKIA

TLSGMNLSARTVEYHIDGDLTVSGLSHPFESLPTHYSGIAFKIYEGS

KNEYPCVEIKASPAKVLQGHNVEGTTDLALCSEALLLNFANSLPCLY

DLLDVNATTISRIDATFSARAPNENIAKQVIDHLRNVSNGQTKSTRS

QNWESTVTWNETSRHRTLVAYLKHVELQHQIQQLSSKPSAKMTSYQK

EQLKVLSNPDLLEFASGLVRFEARIKTRYLKSFGLPLNLFDAIRFAS

DYNSQGKDLIFDLWSFSFSELFKAFEGDSMNIYDDSAVLDAIQSKHF

TITPSGKTSFAKASRYFGFYRRLVNEGYDSVALTMPRNSFWRYVSAL

VECGIPKSQLMNLSTCNNVVPLVRFINVDFSSQRPDWYNEPVLKIA
```

GENE X: 496..831

(SEQ ID NO: 3)
```
translation=MNIYDDSAVLDAIQSKHFTITPSGKTSFAKASRYF

GFYRRLVNEGYDSVALTMPRNSFWRYVSALVECGIPKSQLMNLSTCN

NVVPLVRFINVDFSSQRPDWYNEPVLKIA
```

GENE V: 843..1106

(SEQ ID NO: 4)
```
translation=MIKVEIKPSQAQFTTRSGVSRQGKPYSLNEQLCYV

DLGNEYPVLVKITLDEGQPAYAPGLYTVHLSSFKVGQFGSLMIDRLR

LVPAK
```

GENE VII: 1108..1209

(SEQ ID NO: 5)
```
translation=MEQVADFDTIYQAMIQISVVLCFALGIIAGGQR
```

GENE IX: 1206..1304

(SEQ ID NO: 6)
```
translation=MSVLVYSFASFVLGWCLRSGITYFTRLMETSS
```

GENE VIII: 1301..1522

(SEQ ID NO: 7)
```
translation=MKKSLVLKASVAVATLVPMLSFAAEGDDPAKAAFN

SLQASATEYIGYAWAMVVVIVGATIGIKLFKKFTSKAS
```

GENE III: 1579..2853

(SEQ ID NO: 8)
```
translation=MKKLLFAIPLVVPFYSHSAETVESCLAKPHTENSF

TNVWKDDKTLDRYANYEGCLWNATGVVVCTGDETQCYGTWVPIGLAI

PENEGGGSEGGGSEGGGSEGGGTKPPEYGDTPIPGYTYINPLDGTYP

PGTEQNPANPNPSLEESQPLNTFMFQNNRFRNRQGALTVYTGTVTQG

TDPVKTYYQYTPVSSKAMYDAYWNGKFRDCAFHSGFNEDPFVCEYQG

QSSDLPQPPVNAGGGSGGGSGGGSEGGGSEGGGSEGGGSEGGGSGGG

SGSGDFDYEKMANANKGAMTENADENALQSDAKGKLDSVATDYGAAI

DGFIGDVSGLANGNGATGDFAGSNSQMAQVGDGDNSPLMNNFRQYLP

SLPQSVECRPFVFSAGKPYEFSIDCDKINLFRGVFAFLLYVATFMYV

FSTFANILRNKES
```

GENE VI: 2856..3194

(SEQ ID NO: 9)
```
translation=MPVLLGIPLLLRFLGFLLVTLFGYLLTFLKKGFGK

IAIAISLFLALIIGLNSILVGYLSDISAQLPSDFVQGVQLILPSNAL

PCFYVILSVKAAIFIFDVKQKIVSYLDWDK
```

GENE I: 3196..4242

(SEQ ID NO: 10)
```
translation=MAVYFVTGKLGSGKTLVSVGKIQDKIVAGCKIATN

LDLRLQNLPQVGRFAKTPRVLRIPDKPSISDLLAIGRGNDSYDENKN

GLLVLDECGTWFNTRSWNDKERQPIIDWFLHARKLGWDIIFLVQDLS

IVDKQARSALAEHVVYCRRLDRITLPFVGTLYSLITGSKMPLPKLHV

GVVKYGDSQLSPTVERWLYTGKNLYNAYDTKQAFSSNYDSGVYSYLT

PYLSHGRYFKPLNLGQKMKLTKIYLKKFSRVLCLAIGFASAFTYSYI

TQPKPEVKKVVSQTYDFDKFTIDSSQRLNLSYRYVFKDSKGKLINSD

DLQKQGYSLTYIDLCTVSIKKGNSNEIVKCN
```

GENE IV: 4220..5500

(SEQ ID NO: 11)
```
translation=MKLLNVINFVFLMFVSSSSFAQVIEMNNSPLRDFV

TWYSKQSGESVIVSPDVKGTVTVYSSDVKPENLRNFFISVLRANNFD

MVGSIPSIIQKYNPNNQDYIDELPSSDNQEYDDNSAPSGGFFVPQND

NVTQTFKINNVRAKDLIRVVELFVKSNTSKSSNVLSIDGSNLLVVSA

PKDILDNLPQFLSTVDLPTDQILIEGLIFEVQQGDALDFSFAAGSQR

GTVAGGVNTDRLTSVLSSAGGSFGIFNGDVLGLSVRALKTNSHSKIL

SVPRILTLSGQKGSISVGQNVPFITGRVTGESANVNNPFQTIERQNV

GISMSVFPVAMAGGNIVLDITSKADSLSSSTQASDVITNQRSIATTV

NLRDGQTLLLGGLTDYKNTSQDSGVPFLSKIPLIGLLFSSRSDSNEE

STLYVLVKATIVRAL
```

The term "selection phage," as used herein interchangeably with the term "selection plasmid," refers to a modified phage that comprises a gene of interest to be evolved and lacks a full-length gene encoding a protein required for the generation of infective phage particles. For example, some M13 selection phage provided herein comprise a nucleic acid sequence encoding a protein to be evolved, e.g., under the control of an M13 promoter, and lack all or part of a phage gene encoding a protein required for the generation of infective phage particles, e.g., gI, gII, gIII, gIV, gV, gVI, gVII, gVIII, gIX, or gX, or any combination thereof. For example, some M13 selection phage provided herein comprise a nucleic acid sequence encoding a protein to be evolved, e.g., under the control of an M13 promoter, and lack all or part of a gene encoding a protein required for the generation of infective phage particles, e.g., the gIII gene encoding the pIII protein. An exemplary, non-limiting selection plasmid sequence, SP-MCS, comprising a multiple cloning site, is provided below:

(SEQ ID NO: 30)
```
ATGATTGACATGCTAGTTTTACGATTACCGTTCATCGATTCTCTTGT

TTGCTCCAGACTCTCAGGCAATGACCTGATAGCCTTTGTAGACCTCT

CAAAAATAGCTACCCTCTCCGGCATGAATTTATCAGCTAGAACGGTT
```

-continued

```
GAATATCATGTTGATGGTGATTTGACTGTCTCCGGCCTTTCTCACCC
TTTTGAATCTTTACCTACACATTACTCAGGCATTGCATTTAAAATAT
ATGAGGGTTCTAAAAATTTTTATCCTTGCGTTGAAATAAAGGCTTCT
CCCGCAAAAGTATTACAGGGTCATAATGTTTTTGGTACAACCGATTT
AGCTTTATGCTCTGAGGCTTTATTGCTTAATTTTGCTAATTCTTTGC
CTTGCCTGTATGATTTATTGGATGTTAACGCTACTACTATTAGTAGA
ATTGATGCCACCTTTTCAGCTCGCGCCCCAAATGAAAATATAGCTAA
ACAGGTTATTGACCATTTGCGAAATGTATCTAATGGTCAAACTAAAT
CTACTCGTTCGCAGAATTGGGAATCAACTGTTACATGGAATGAAACT
TCCAGACACCGTACTTTAGTTGCATATTTAAAACATGTTGAGCTACA
GCACCAGATTCAGCAATTAAGCTCTAAGCCATCCGCAAAAATGACCT
CTTATCAAAAGGAGCAATTAAAGGTACTCTCTAATCCTGACCTGTTG
GAGTTTGCTTCCGGGCTGGTTCGCTTTGAAGCTCGAATTAGAACGCG
ATATTTGAAGTCTTTCGGGCTTCCTCTTAATCTTTTTGATGCAATCC
GCTTTGCTTCTGACTATAATAGTCAGGGTAAAGACCTGATTTTTGAT
TTATGGTCATTCTCGTTTTCTGAACTGTTTAAAGCATTTGAGGGGGA
TTCAATGAATATTTATGACGATTCCGCAGTATTGGACGCTATCCAGT
CTAAACATTTTACTATTACCCCCTCTGGCAAAACTTCTTTTGCAAAA
GCCTCTCGCTATTTTGGTTTTTATCGTCGTCTGGTAAACGAGGGTTA
TGATAGTGTTGCTCTTACTATGCCTCGTAATTCCTTTTGGCGTTATG
TATCTGCATTAGTTGAATGTGGTATTCCTAAATCTCAACTGATGAAT
CTTTCTACCTGTAATAATGTTGTTCCGTTAGTTCGTTTTATTAACGT
AGATTTTCTTCCCAACGTCCTGACTGGTATAATGAGCCAGTTCTTA
AAATCGCATAAGGTAATTCACAATGATTAAAGTTGAAATTAAACCAT
CTCAAGCCCAATTTACTACTCGTTCTGGTGTTTCTCGTCAGGGCAAG
CCTTATTCACTGAATGAGCAGCTTTGTTACGTTGATTTGGGTAATGA
ATATCCGGTTCTTGTCAAGATTACTCTTGATGAAGGTCAGCCAGCCT
ATGCGCCTGGTCTGTACACCGTTCATCTGTCCTCTTTCAAAGTTGGT
CAGTTCGGTTCCCTTATGATTGACCGTCTGCGCCTCGTTCCGGCTAA
GTAACATGGAGCAGGTCGCGGATTTCGACACAATTTATCAGGCGATG
ATACAAATCTCCGTTGTACTTTGTTTCGCGCTTGGTATAATCGCTGG
GGGTCAAAGATGAGTGTTTTAGTGTATTCTTTCGCCTCTTTCGTTTT
AGGTTGGTGCCTTCGTAGTGGCATTACGTATTTTACCCGTTTAATGG
AAACTTCCTCATGAAAAGTCTTTAGTCCTCAAAGCCTCTGTAGCCG
TTGCTACCCTCGTTCCGATGCTGTCTTTCGCTGCTGAGGGTGACGAT
CCCGCAAAAGCGGCCTTTAACTCCCTGCAAGCCTCAGCGACCGAATA
TATCGGTTATGCGTGGGCGATGGTTGTTGTCATTGTCGGCGCAACTA
TCGGTATCAAGCTGTTTAAGAAATTCACCTCGAAAGCAAGCTGATAA
ACCGATACAATTAAAGGCTCCTTTTGGAGCCTTTTTTTTCGCGCCAG
AAGGAGACCAAGCTTGCATGCCTGCAGGTCGACTCTAGAGGATCCCC
GGGTACCGAGCTCGAATTCTGGAGATTTTCAACATGCTCCCTCAATC
```

-continued

```
GGTTGAATGTCGCCCTTTTGTCTTTAGCGCTGGTAAACCATATGAAT
TTTCTATTGATTGTGACAAAATGAACTTATTCCGTGGTGTCTTTGCG
TTTCTTTTATATGTTGCCACCTTTATGTATGTATTTTCTACGTTTGC
TAACATACTGCGTAATAAGGAGTCTTAATCATGCCAGTTCTTTTGGG
TATTCCGTTATTATTGCGTTTCCTCGGTTTCCTTCTGGTAACTTTGT
TCGGCTATCTGCTTACTTTTCTTAAAAAGGGCTTCGGTAAGATAGCT
ATTGCTATTTCATTGTTTCTTGCTCTTATTATTGGGCTTAACTCAAT
TCTTGTGGGTTATCTCTCTGATATTAGCGCTCAATTACCCTCTGACT
TTGTTCAGGGTGTTCAGTTAATTCTCCCGTCTAATGCGCTTCCCTGT
TTTTATGTTATTCTCTCTGTAAAGGCTGCTATTTTCATTTTTGACGT
TAAACAAAAAATCGTTTCTTATTTGGATTGGGATAAATAATATGGCT
GTTTATTTTGTAACTGGCAAATTAGGCTCTGGAAAGACGCTCGTTAG
CGTTGGTAAGATTCAGGATAAAATTGTAGCTGGGTGCAAAATAGCAA
CTAATCTTGATTTAAGGCTTCAAAACCTCCCGCAAGTCGGGAGGTTC
GCTAAAACGCCTCGCGTTCTTAGAATACCGGATAAGCCTTCTATATC
TGATTTGCTTGCTATTGGGCGCGGTAATGATTCCTACGATGAAAATA
AAAACGGCTTGCTTGTTCTCGATGAGTGCGGTACTTGGTTTAATACC
CGTTCTTGGAATGATAAGGAAAGACAGCCGATTATTGATTGGTTTCT
ACATGCTCGTAAATTAGGATGGGATATTATTTTTCTTGTTCAGGACT
TATCTATTGTTGATAAACAGGCGCGTTCTGCATTAGCTGAACATGTT
GTTTATTGTCGTCGTCTGGACAGAATTACTTTACCTTTTGTCGGTAC
TTTATATTCTCTTATTACTGGCTCGAAAATGCCTCTGCCTAAATTAC
ATGTTGGCGTTGTTAAATATGGCGATTCTCAATTAAGCCCTACTGTT
GAGCGTTGGCTTTATACTGGTAAGAATTTGTATAACGCATATGATAC
TAAACAGGCTTTTTCTAGTAATTATGATTCCGGTGTTTATTCTTATT
TAACGCCTTATTTATCACACGGTCGGTATTTCAAACCATTAAATTTA
GGTCAGAAGATGAAATTAACTAAAATATATTTGAAAAAGTTTTCTCG
CGTTCTTTGTCTTGCGATTGGATTTGCATCAGCATTTACATATAGTT
ATATAACCCAACCTAAGCCGGAGGTTAAAAAGGTAGTCTCTCAGACC
TATGATTTTGATAAATTCACTATTGACTCTTCTCAGCGTCTTAATCT
AAGCTATCGCTATGTTTTCAAGGATTCTAAGGGAAAATTAATTAATA
GCGACGATTTACAGAAGCAAGGTTATTCACTCACATATATTGATTTA
TGTACTGTTTCCATTAAAAAAGGTAATTCAAATGAAATTGTTAAATG
TAATTAATTTTGTTTTCTTGATGTTTGTTTCATCATCTTCTTTTGCT
CAGGTAATTGAAATGAATAATTCGCCTCTGCGCGATTTTGTAACTTG
GTATTCAAAGCAATCAGGCGAATCCGTTATTGTTTCTCCCGATGTAA
AAGGTACTGTTACTGTATATTCATCTGACGTTAAACCTGAAATCTA
CGCAATTTCTTTATTTCTGTTTTACGTGCAAGTAATTTTGATATGGT
TGGTTCTAACCCTTCCATTATTCAGAAGTATAATCCAAACAATCAGG
ATTATATTGATGAATTGCCATCATCTGATAATCAGGAATATGATGAT
AATTCCGCTCCTTCTGGTGGTTTCTTTGTTCCGCAAAATGATAATGT
```

-continued

```
TACTCAAACTTTTAAAATTAATAACGTTCGGGCAAAGGATTTAATAC

GAGTTGTCGAATTGTTTGTAAAGTCTAATACTTCTAAATCCTCAAAT

GTATTATCTATTGACGGCTCTAATCTATTAGTTGTTAGTGCACCTAA

AGATATTTTAGATAACCTTCCTCAATTCCTTTCTACTGTTGATTTGC

CAACTGACCAGATATTGATTGAGGGTTTGATATTTGAGGTTCAGCAA

GGTGATGCTTTAGATTTTTCATTTGCTGCTGGCTCTCAGCGTGGCAC

TGTTGCAGGCGGTGTTAATACTGACCGCCTCACCTCTGTTTTATCTT

CTGCTGGTGGTTCGTTCGGTATTTTTAATGGCGATGTTTTAGGGCTA

TCAGTTCGCGCATTAAAGACTAATAGCCATTCAAAAATATTGTCTGT

GCCACGTATTCTTACGCTTTCAGGTCAGAAGGGTTCTATCTTTGTTG

GCCAGAATGTCCCTTTTATTACTGGTCGTGTGACTGGTGAATCTGCC

AATGTAAATAATCCATTTCAGACGATTGAGCGTCAAAATGTAGGTAT

TTCCATGAGCGTTTTTCCTGTTGCAATGGCTGGCGGTAATATTGTTC

TGGATATTACCAGCAAGGCCGATAGTTTGAGTTCTTCTACTCAGGCA

AGTGATGTTATTACTAATCAAAGAAGTACTGCTACAACGGTTAATTT

GCGTGATGGACAGACTCTTTTACTCGGTGGCCTCACTGATTATAAAA

ACACTTCTCAGGATTCTGGCGTACCGTTCCTGTCTAAAATCCCTTTA

ATCGGCCTCCTGTTTAGCTCCCGCTCTGATTCTAACGAGGAAAGCAC

GTTATACGTGCTCGTCAAAGCAACCATAGTACGCGCCCTGTAGCGGC

GCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCT

TTCTCGCCACGTTCGCCGGCTTTCCCCGTCAAGCTCTAAATCGGGG

CTCCCTTTAGGGTTCCGATTTAGTGCTTTACGGCACCTCGACCCCAA

AAAACTTGATTTGGGTGATGGTTCACGTAGTGGGCCATCGCCCTGAT

AGACGGTTTTTCGCCCTTTGACGTTGGAGTCCACGTTCTTTAATAGT

GGACTCTTGTTCCAAACTGGAACAACACTCAACCCTATCTCGGGCTA

TTCTTTTGATTTATAAGGGATTTTGCCGATTTCGGCCTATTGGTTAA

AAAATGAGCTGATTTAACAAAAATTTAACGCGAATTTTAACAAAATA

TTAACGTTTACAATTTAAATATTTGCTTATACAATCTTCCTGTTTTT

GGGGCTTTTCTTATTATCAACCGGGGTACAT
```

The term "helper phage," as used herein interchangeable with the terms "helper phagemid" and "helper plasmid," refers to a nucleic acid construct comprising a phage gene required for the phage life cycle, or a plurality of such genes, but lacking a structural element required for genome packaging into a phage particle. For example, a helper phage may provide a wild-type phage genome lacking a phage origin of replication. In some embodiments, a helper phage is provided that comprises a gene required for the generation of phage particles, but lacks a gene required for the generation of infectious particles, for example, a full-length pIII gene. In some embodiments, the helper phage provides only some, but not all, genes required for the generation of phage particles. Helper phages are useful to allow modified phages that lack a gene required for the generation of phage particles to complete the phage life cycle in a host cell. Typically, a helper phage will comprise the genes required for the generation of phage particles that are lacking in the phage genome, thus complementing the phage genome. In the continuous evolution context, the helper phage typically complements the selection phage, but both lack a phage gene required for the production of infectious phage particles.

The term "replication product," as used herein, refers to a nucleic acid that is the result of viral genome replication by a host cell. This includes any viral genomes synthesized by the host cell from a viral genome inserted into the host cell. The term includes non-mutated as well as mutated replication products.

Accessory Plasmids and Helper Constructs

The term "accessory plasmid," as used herein, refers to a plasmid comprising a gene required for the generation of infectious viral particles under the control of a conditional promoter. In the context of continuous evolution described herein, the conditional promoter of the accessory plasmid is typically activated by a function of the gene of interest to be evolved. Accordingly, the accessory plasmid serves the function of conveying a competitive advantage to those viral vectors in a given population of viral vectors that carry a gene of interest able to activate the conditional promoter. Only viral vectors carrying an "activating" gene of interest will be able to induce expression of the gene required to generate infectious viral particles in the host cell, and, thus, allow for packaging and propagation of the viral genome in the flow of host cells. Vectors carrying non-activating versions of the gene of interest, on the other hand, will not induce expression of the gene required to generate infectious viral vectors, and, thus, will not be packaged into viral particles that can infect fresh host cells.

In some embodiments, the conditional promoter of the accessory plasmid is a promote the transcriptional activity of which can be regulated over a wide range, for example, over 2, 3, 4, 5, 6, 7, 8, 9, or 10 orders of magnitude by the activating function, for example, function of a protein encoded by the gene of interest. In some embodiments, the level of transcriptional activity of the conditional promoter depends directly on the desired function of the gene of interest. This allows for starting a continuous evolution process with a viral vector population comprising versions of the gene of interest that only show minimal activation of the conditional promoter. In the process of continuous evolution, any mutation in the gene of interest that increases activity of the conditional promoter directly translates into higher expression levels of the gene required for the generation of infectious viral particles, and, thus, into a competitive advantage over other viral vectors carrying minimally active or loss-of-function versions of the gene of interest.

The stringency of selective pressure imposed by the accessory plasmid in a continuous evolution procedure as provided herein can be modulated. In some embodiments, the use of low copy number accessory plasmids results in an elevated stringency of selection for versions of the gene of interest that activate the conditional promoter on the accessory plasmid, while the use of high copy number accessory plasmids results in a lower stringency of selection. The terms "high copy number plasmid" and "low copy number plasmid" are art-recognized and those of skill in the art will be able to ascertain whether a given plasmid is a high or low copy number plasmid. In some embodiments, a low copy number accessory plasmid is a plasmid exhibiting an average copy number of plasmid per host cell in a host cell population of about 5 to about 100. In some embodiments, a very low copy number accessory plasmid is a plasmid exhibiting an average copy number of plasmid per host cell in a host cell population of about 1 to about 10. In some embodiments, a very low copy number accessory plasmid is a single-copy per cell plasmid. In some embodiments, a high copy number accessory plasmid is a plasmid exhibiting an average copy number of plasmid per host cell in a host cell population of about 100 to about 5000. The copy number of an accessory plasmid will depend to a large part on the origin of replication employed. Those of skill in the art will be able to determine suitable origins of replication in order to achieve a desired copy number. The following table lists some non-limiting examples of vectors of different copy numbers and with different origins of replication,

| Plasmids | | | |
| --- | --- | --- | --- |
| pUC vectors | pMB1* | 500-700 | high copy |
| pBluescript ® vectors | ColE1 | 300-500 | high copy |
| pGEM ® vectors | pMB1* | 300-400 | high copy |
| pTZ vectors | pMB1* | >1000 | high copy |
| pBR322 and derivatives | pMB1* | 15-20 | low copy |
| pACYC and derivatives | p15A | 10-12 | low copy |
| pSC101 and derivatives | pSC101 | ~5 | very low copy |

*The pMB1 origin of replication is closely related to that of ColE1 and falls in the same incompatibility group. The high-copy plasmids listed here contain mutated versions of this origin.

It should be understood that the function of the accessory plasmid, namely to provide a gene required for the generation of viral particles under the control of a conditional promoter the activity of which depends on a function of the gene of interest, can be conferred to a host cell in alternative ways. Such alternatives include, but are not limited to, permanent insertion of a gene construct comprising the conditional promoter and the respective gene into the genome of the host cell, or introducing it into the host cell using an different vector, for example, a phagemid, a cosmid, a phage, a virus, or an artificial chromosome. Additional ways to confer accessory plasmid function to host cells will be evident to those of skill in the art, and the invention is not limited in this respect.

The sequences of two exemplary, non-limiting accessory plasmids, AP-MCS-A, and AP-MCS-P, respectively, are provided below:

```
AP-MCS-A:
                                          (SEQ ID NO: 31)
GGCTGTTTTGGCGGATGAGAGAAGATTTTCAGCCTGATACAGATTAA

ATCAGAACGCAGAAGCGGTCTGATAAAACAGAATTTGCCTGGCGGCA

GTAGCGCGGTGGTCCCACCTGACCCCATGCCGAACTCAGAAGTGAAA

CGCCGTAGCGCCGATGGTAGTGTGGGGTCTCCCCATGCGAGAGTAGG

GAACTGCCAGGCATCAAATAAAACGAAAGGCTCAGTCGAAAGACTGG

GCCTTTCGTTTTATCTGTTGTTTGTCGGTGAACGCTCTCCTGAGTAG

GACAAATCCGCCGGGAGCGGATTTGAACGTTGCGAAGCAACGGCCCG

GAGGGTGGCGGGCAGGACGCCCGCCATAAACTGCCAGGCATCAAATT

AAGCAGAAGGCCATCCTGACGGATGGCCTTTTTGCGTTTCTACAAAC

TCTACTCTGCTAGCAAGTAAGGCCGACAAGCTTGCATGCCTGCAGGT

CGACTCTAGAGGATCCCCGGGTACCGAGCTCGAATTCCCTTTTTTT

TGGAGATTTTCAACGTGAAAAAATTATTATTCGCAATTCCTTTAGTT

GTTCCTTTCTATTCTCACTCCGCTGAAACTGTTGAAAGTTGTTTAGC

AAAACCCCATACAGAAAATTCATTTACTAACGTCTGGAAAGACGACA

AAACTTTAGATCGTTACGCTAACTATGAGGGCTGTCTGTGGAATGCT

ACAGGCGTTGTAGTTTGTACTGGTGACGAAACTCAGTGTTACGGTAC

ATGGGTTCCTATTGGGCTTGCTATCCCTGAAAATGAGGGTGGTGGCT

CTGAGGGTGGCGGTTCTGAGGGTGGCGGTTCTGAGGGTGGCGGTACT

AAACCTCCTGAGTACGGTGATACACCTATTCCGGGCTATACTTATAT

CAACCCTCTCGACGGCACTTATCCGCCTGGTACTGAGCAAAACCCCG

CTAATCCTAATCCTTCTCTTGAGGAGTCTCAGCCTCTTAATACTTTC

ATGTTTCAGAATAATAGGTTCCGAAATAGGCAGGGGGCATTAACTGT

TTATACGGGCACTGTTACTCAAGGCACTGACCCCGTTAAAACTTATT

ACCAGTACACTCCTGTATCATCAAAAGCCATGTATGACGCTTACTGG

AACGGTAAATTCAGAGACTGCGCTTTCCATTCTGGCTTTAATGAGGA

TCCATTCGTTTGTGAATATCAAGGCCAATCGTCTGACCTGCCTCAAC

CTCCTGTCAATGCTGGCGGCGGCTCTGGTGGTGGTTCTGGTGGCGGC

TCTGAGGGTGGTGGCTCTGAGGGTGGCGGTTCTGAGGGTGGCGGCTC

TGAGGGAGGCGGTTCCGGTGGTGGCTCTGGTTCCGGTGATTTTGATT

ATGAAAGATGGCAAACGCTAATAAGGGGGCTATGACCGAAAATGCC

GATGAAAACGCGCTACAGTCTGACGCTAAAGGCAAACTTGATTCTGT

CGCTACTGATTACGGTGCTGCTATCGATGGTTTCATTGGTGACGTTT

CCGGCCTTGCTAATGGTAATGGTGCTACTGGTGATTTTGCTGGCTCT

AATTCCCAAATGGCTCAAGTCGGTGACGGTGATAATTCACCTTTAAT

GAATAATTTCCGTCAATATTTACCTTCCCTCCCTCAATCGGTTGAAT

GTCGCCCTTTTGTCTTTGGCGCTGGTAAACCATATGAATTTTCTATT

GATTGTGACAAAATAAACTTATTCCGTGGTGTCTTTGCGTTTCTTTT

ATATGTTGCCACCTTTATGTATGTATTTTCTACGTTTGCTAACATAC

TGCGTAATAAGGAGTCTTAATCATGCCAGTTCTAGCATAACCCCTTG

GGGCCTCTAAACGGGTCTTGAGGGGTTTTTTGCCTTGTCGGCCTTAC

TTGCTAAATACATTCAAATATGTATCCGCTCATGAGACAATAACCCT

GATAAATGCTTCAATAATATTGAAAAAGGAAGAGTATGAGTATTCAA

CATTTCCGTGTCGCCCTTATTCCCTTTTTTGCGGCATTTTGCCTTCC

TGTTTTTGCTCACCCAGAAACGCTGGTGAAAGTAAAAGATGCTGAAG

ATCAGTTGGGTGCACGAGTGGGTTACATCGAACTGGATCTCAACAGC

GGTAAGATCCTTGAGAGTTTTCGCCCCGAAGAACGTTTTCCAATGAT

GAGCACTTTTAAAGTTCTGCTATGTGGCGCGGTATTATCCCGTATTG

ACGCCGGGCAAGAGCAACTCGGTCGCCGCATACACTATTCTCAGAAT

GACTTGGTTGAGTACTCACCAGTCACAGAAAAGCATCTTACGGATGG

CATGACAGTAAGAGAATTATGCAGTGCTGCCATAACCATGAGTGATA

ACACTGCGGCCAACTTACTTCTGACAACGATCGGAGGACCGAAGGAG

CTAACCGCTTTTTTGCACAACATGGGGGATCATGTAACTCGCCTTGA

TCGTTGGGAACCGGAGCTGAATGAAGCCATACCAAACGACGAGCGTG

ACACCACGATGCCTGTAGCAATGGCAACAACGTTGCGCAAACTATTA

ACTGGCGAACTACTTACTCTAGCTTCCCGGCAACAATTGATAGACTG
```

```
GATGGAGGCGGATAAAGTTGCAGGACCACTTCTGCGCTCGGCCCTTC
CGGCTGGCTGGTTTATTGCTGATAAATCTGGAGCCGGTGAGCGTGGC
TCTCGCGGTATCATTGCAGCACTGGGGCCAGATGGTAAGCCCTCCCG
TATCGTAGTTATCTACACGACGGGGAGTCAGGCAACTATGGATGAAC
GAAATAGACAGATCGCTGAGATAGGTGCCTCACTGATTAAGCATTGG
TAAGAACCTCAGATCCTTCCGTGATGGTAACTTCACTAGTTTAAAAG
GATCTAGGTGAAGATCCTTTTTGATAATCTCATGACCAAAATCCCTT
AACGTGAGTTTTCGTTCCACTGAGCGTCAGAGAACCTCAGATCCTTC
CGTATTTAGCCAGTATGTTCTCTAGTGTGGTTCGTTGTTTTGCGTG
AGCCATGAGAACGAACCATTGAGATCATGCTTACTTTGCATGTCACT
CAAAAATTTTGCCTCAAAACTGGTGAGCTGAATTTTTGCAGTTAAAG
CATCGTGTAGTGTTTTTCTTAGTCCGTTACGTAGGTAGGAATCTGAT
GTAATGGTTGTTGGTATTTTGTCACCATTCATTTTTATCTGGTTGTT
CTCAAGTTCGGTTACGAGATCCATTTGTCTATCTAGTTCAACTTGGA
AAATCAACGTATCAGTCGGGCGGCCTCGCTTATCAACCACCAATTTC
ATATTGCTGTAAGTGTTTAAATCTTTACTTATTGGTTTCAAAACCCA
TTGGTTAAGCCTTTTAAACTCATGGTAGTTATTTTCAAGCATTAACA
TGAACTTAAATTCATCAAGGCTAATCTCTATATTTGCCTTGTGAGTT
TTCTTTTGTGTTAGTTCTTTTAATAACCACTCATAAATCCTCATAGA
GTATTTGTTTTCAAAAGACTTAACATGTTCCAGATTATATTTTATGA
ATTTTTTTAACTGGAAAAGATAAGGCAATATCTCTTCACTAAAAACT
AATTCTAATTTTTCGCTTGAGAACTTGGCATAGTTTGTCCACTGGAA
AATCTCAAAGCCTTTAACCAAAGGATTCCTGATTTCCACAGTTCTCG
TCATCAGCTCTCTGGTTGCTTTAGCTAATACACCATAAGCATTTTCC
CTACTGATGTTCATCATCTGAGCGTATTGGTTATAAGTGAACGATAC
CGTCCGTTCTTTCCTTGTAGGGTTTTCAATCGTGGGGTTGAGTAGTG
CCACACAGCATAAAATTAGCTTGGTTTCATGCTCCGTTAAGTCATAG
CGACTAATCGCTAGTTCATTTGCTTTGAAAACAACTAATTCAGACAT
ACATCTCAATTGGTCTAGGTGATTTTAATCACTATACCAATTGAGAT
GGGCTAGTCAATGATAATTACTAGTCCTTTTCCTTTGAGTTGTGGGT
ATCTGTAAATTCTGCTAGACCTTTGCTGGAAAACTTGTAAATTCTGC
TAGACCCTCTGTAAATTCCGCTAGACCTTTGTGTGTTTTTTTGTTT
ATATTCAAGTGGTTATAATTTATAGAATAAAGAAAGAATAAAAAAAG
ATAAAAAGAATAGATCCCAGCCCTGTGTATAACTCACTACTTTAGTC
AGTTCCGCAGTATTACAAAAGGATGTCGCAAACGCTGTTTGCTCCTC
TACAAAACAGACCTTAAAACCCTAAAGGCTTAAGTAGCACCCTCGCA
AGCTCGGGCAAATCGCTGAATATTCCTTTTGTCTCCGACCATCAGGC
ACCTGAGTCGCTGTCTTTTTCGTGACATTCAGTTCGCTGCGCTCACG
GCTCTGGCAGTGAATGGGGGTAAATGGCACTACAGGCGCCTTTTATG
GATTCATGCAAGGAAACTACCCATAATACAAGAAAAGCCCGTCACGG
GCTTCTCAGGGCGTTTTATGGCGGGTCTGCTATGTGGTGCTATCTGA
```

```
CTTTTTGCTGTTCAGCAGTTCCTGCCCTCTGATTTTCCAGTCTGACC
ACTTCGGATTATCCCGTGACAGGTCATTCAGACTGGCTAATGCACCC
AGTAAGGCAGCGGTATCATCAACT
```

AP-MCS-P:

(SEQ ID NO: 32)

```
GGCTGTTTTGGCGGATGAGAGAAGATTTTCAGCCTGATACAGATTAA
ATCAGAACGCAGAAGCGGTCTGATAAAACAGAATTTGCCTGGCGGCA
GTAGCGCGGTGGTCCCACCTGACCCCATGCCGAACTCAGAAGTGAAA
CGCCGTAGCGCCGATGGTAGTGTGGGGTCTCCCCATGCGAGAGTAGG
GAACTGCCAGGCATCAAATAAAACGAAAGGCTCAGTCGAAAGACTGG
GCCTTTCGTTTTATCTGTTGTTTGTCGGTGAACGCTCTCCTGAGTAG
GACAAATCCGCCGGGAGCGGATTTGAACGTTGCGAAGCAACGGCCCG
GAGGGTGGCGGGCAGGACGCCCGCCATAAACTGCCAGGCATCAAATT
AAGCAGAAGGCCATCCTGACGGATGGCCTTTTTGCGTTTCTACAAAC
TCTACTCTGCTAGCAAGTAAGGCCGACAAGCTTGCATGCCTGCAGGT
CGACTCTAGAGGATCCCCGGGTACCGAGCTCGAATTCCCTTTTTTTT
TGGAGATTTTCAACGTGAAAAAATTATTATTCGCAATTCCTTTAGTT
GTTCCTTTCTATTCTCACTCCGCTGAAACTGTTGAAAGTTGTTTAGC
AAAACCCCATACAGAAAATTCATTTACTAACGTCTGGAAAGACGACA
AAACTTTAGATCGTTACGCTAACTATGAGGGCTGTCTGTGGAATGCT
ACAGGCGTTGTAGTTTGTACTGGTGACGAAACTCAGTGTTACGGTAC
ATGGGTTCCTATTGGGCTTGCTATCCCTGAAAATGAGGGTGGTGGCT
CTGAGGGTGGCGGTTCTGAGGGTGGCGGTTCTGAGGGTGGCGGTACT
AAACCTCCTGAGTACGGTGATACACCTATTCCGGGCTATACTTATAT
CAACCCTCTCGACGGCACTTATCCGCCTGGTACTGAGCAAAACCCCG
CTAATCCTAATCCTTCTCTTGAGGAGTCTCAGCCTCTTAATACTTTC
ATGTTTCAGAATAATAGGTTCCGAAATAGGCAGGGGGCATTAACTGT
TTATACGGGCACTGTTACTCAAGGCACTGACCCCGTTAAAACTTATT
ACCAGTACACTCCTGTATCATCAAAAGCCATGTATGACGCTTACTGG
AACGGTAAATTCAGAGACTGCGCTTTCCATTCTGGCTTTAATGAGGA
TCCATTCGTTTGTGAATATCAAGGCCAATCGTCTGACCTGCCTCAAC
CTCCTGTCAATGCTGGCGGCGGCTCTGGTGGTGGTTCTGGTGGCGGC
TCTGAGGGTGGTGGCTCTGAGGGTGGCGGTTCTGAGGGTGGCGGCTC
TGAGGGAGGCGGTTCCGGTGGTGGCTCTGGTTCCGGTGATTTTGATT
ATGAAAAGATGGCAAACGCTAATAAGGGGGCTATGACCGAAAATGCC
GATGAAAACGCGCTACAGTCTGACGCTAAAGGCAAACTTGATTCTGT
CGCTACTGATTACGGTGCTGCTATCGATGGTTTCATTGGTGACGTTT
CCGGCCTTGCTAATGGTAATGGTGCTACTGGTGATTTTGCTGGCTCT
AATTCCCAAATGGCTCAAGTCGGTGACGGTGATAATTCACCTTTAAT
GAATAATTTCCGTCAATATTTACCTTCCCTCCCTCAATCGGTTGAAT
GTCGCCCTTTTGTCTTTGGCGCTGGTAAACCATATGAATTTTCTATT
GATTGTGACAAAATAAACTTATTCCGTGGTGTCTTTGCGTTTCTTTT
```

```
ATATGTTGCCACCTTTATGTATGTATTTTCTACGTTTGCTAACATAC
TGCGTAATAAGGAGTCTTAATCATGCCAGTTCTAGCATAACCCCTTG
GGGCCTCTAAACGGGTCTTGAGGGGTTTTTTGCCTTGTCGGCCTTAC
TTGCTAAATACATTCAAATATGTATCCGCTCATGAGACAATAACCCT
GATAAATGCTTCAATAATATTGAAAAAGGAAGAGTATGAGTATTCAA
CATTTCCGTGTCGCCCTTATTCCCTTTTTTGCGGCATTTTGCCTTCC
TGTTTTTGCTCACCCAGAAACGCTGGTGAAAGTAAAAGATGCTGAAG
ATCAGTTGGGTGCACGAGTGGGTTACATCGAACTGGATCTCAACAGC
GGTAAGATCCTTGAGAGTTTTCGCCCCGAAGAACGTTTTCCAATGAT
GAGCACTTTTAAAGTTCTGCTATGTGGCGCGGTATTATCCCGTATTG
ACGCCGGGCAAGAGCAACTCGGTCGCCGCATACACTATTCTCAGAAT
GACTTGGTTGAGTACTCACCAGTCACAGAAAAGCATCTTACGGATGG
CATGACAGTAAGAGAATTATGCAGTGCTGCCATAACCATGAGTGATA
ACACTGCGGCCAACTTACTTCTGACAACGATCGGAGGACCGAAGGAG
CTAACCGCTTTTTTGCACAACATGGGGGATCATGTAACTCGCCTTGA
TCGTTGGGAACCGGAGCTGAATGAAGCCATACCAAACGACGAGCGTG
ACACCACGATGCCTGTAGCAATGGCAACAACGTTGCGCAAACTATTA
ACTGGCGAACTACTTACTCTAGCTTCCCGGCAACAATTGATAGACTG
GATGGAGGCGGATAAAGTTGCAGGACCACTTCTGCGCTCGGCCCTTC
CGGCTGGCTGGTTTATTGCTGATAAATCGGAGCCGGTGAGCGTGGC
TCTCGCGGTATCATTGCAGCACTGGGGCCAGATGGTAAGCCCTCCCG
TATCGTAGTTATCTACACGACGGGGAGTCAGGCAACTATGGATGAAC
GAAATAGACAGATCGCTGAGATAGGTGCCTCACTGATTAAGCATTGG
TAAGAACCTCAGATCCTTCCGTGATGGTAACTTCACTAGTTTAAAAG
GATCTAGGTGAAGATCCTTTTTGATAATCTCATGACCAAAATCCCTT
AACGTGAGTTTTCGTTCCACTGAGCGTCAGAGAACCTCAGATCCTTC
CGTATTTAGCCAGTATGTTCTCTAGTGTGGTTCGTTGTTTTTGCGTG
AGCCATGAGAACGAACCATTGAGATCATGCTTACTTTGCATGTCACT
CAAAATTTTGCCTCAAAACTGGTGAGCTGAATTTTTGCAGTTAAAG
CATCGTGTAGTGTTTTCTTAGTCCGTTACGTAGGTAGGAATCTGAT
GTAATGGTTGTTGGTATTTTGTCACCATTCATTTTTATCTGGTTGTT
CTCAAGTTCGGTTACGAGATCCATTTGTCTATCTAGTTCAACTTGGA
AAATCAACGTATCAGTCGGGCGGCCTCGCTTATCAACCACCAATTTC
ATATTGCTGTAAGTGTTTAAATCTTTACTTATTGGTTTCAAAACCCA
TTGGTTAAGCCTTTTAAACTCATGGTAGTTATTTTCAAGCATTAACA
TGAACTTAAATTCATCAAGGCTAATCTCTATATTTGCCTTGTGAGTT
TTCTTTTGTGTTAGTTCTTTTAATAACCACTCATAAATCCTCATAGA
GTATTTGTTTTCAAAAGACTTAACATGTTCCAGATTATATTTTATGA
ATTTTTTTAACTGGAAAAGATAAGGCAATATCTCTTCACTAAAAACT
AATTCTAATTTTTCGCTTGAGAACTTGGCATAGTTTGTCCACTGGAA
AATCTCAAAGCCTTTAACCAAAGGATTCCTGATTTCCACAGTTCTCG
```

```
TCATCAGCTCTCTGGTTGCTTTAGCTAATACACCATAAGCATTTTCC
CTACTGATGTTCATCATCTGAGCGTATTGGTTATAAGTGAACGATAC
CGTCCGTTCTTTCCTTGTAGGGTTTTCAATCGTGGGGTTGAGTAGTG
CCACACAGCATAAAATTAGCTTGGTTTCATGCTCCGTTAAGTCATAG
CGACTAATCGCTAGTTCATTTGCTTTGAAAACAACTAATTCAGACAT
ACATCTCAATTGGTCTAGGTGATTTTAATCACTATACCAATTGAGAT
GGGCTAGTCAATGATAATTACTAGTCCTTTTCCTTTGAGTTGTGGGT
ATCTGTAAATTCTGCTAGACCTTTGCTGGAAAACTTGTAAATTCTGC
TAGACCCTCTGTAAATTCCGCTAGACCTTTGTGTGTTTTTTTTGTTT
ATATTCAAGTGGTTATAATTTATAGAATAAAGAAAGAATAAAAAAAG
ATAAAAAGAATAGATCCCAGCCCTGTGTATAACTCACTACTTTAGTC
AGTTCCGCAGTATTACAAAAGGATGTCGCAAACGCTGTTTGCTCCTC
TACAAAACAGACCTTAAAACCCTAAAGGCTTAAGTAGCACCCTCGCA
AGCTCGGGCAAATCGCTGAATATTCCTTTTGTCTCCGACCATCAGGC
ACCTGAGTCGCTGTCTTTTTCGTGACATTCAGTTCGCTGCGCTCACG
GCTCTGGCAGTGAATGGGGGTAAATGGCACTACAGGCGCCTTTTATG
GATTCATGCAAGGAAACTACCCATAATACAAGAAAAGCCCGTCACGG
GCTTCTCAGGGCGTTTTATGGCGGGTCTGCTATGTGGTGCTATCTGA
CTTTTTGCTGTTCAGCAGTTCCTGCCCTCTGATTTTCCAGTCTGACC
ACTTCGGATTATCCCGTGACAGGTCATTCAGACTGGCTAATGCACCC
AGTAAGGCAGCGGTATCATCAACT
```

Mutagens and Mutagenesis-Promoting Expression Constructs

The term "mutagen," as used herein, refers to an agent that induces mutations or increases the rate of mutation in a given biological system, for example, a host cell, to a level above the naturally-occurring level of mutation in that system. Some exemplary mutagens useful for continuous evolution procedures are provided elsewhere herein and other useful mutagens will be evident to those of skill in the art. Useful mutagens include, but are not limited to, ionizing radiation, ultraviolet radiation, base analogs, deaminating agents (e.g., nitrous acid), intercalating agents (e.g., ethidium bromide), alkylating agents (e.g., ethylnitrosourea), transposons, bromine, azide salts, psoralen, benzene, 3-Chloro-4-(dichloromethyl)-5-hydroxy-2(5H)-furanone (MX) (CAS no. 77439-76-0), O,O-dimethyl-S-(phthalimidomethyl)phosphorodithioate (phos-met) (CAS no. 732-11-6), formaldehyde (CAS no. 50-00-0), 2-(2-furyl)-3-(5-nitro-2-furyl)acrylamide (AF-2) (CAS no. 3688-53-7), glyoxal (CAS no. 107-22-2), 6-mercaptopurine (CAS no. 50-44-2), N-(trichloromethylthio)-4-cyclohexane-1,2-dicarboximide (captan) (CAS no. 133-06-2), 2-aminopurine (CAS no. 452-06-2), methyl methane sulfonate (MMS) (CAS No. 66-27-3), 4-nitroquinoline 1-oxide (4-NQO) (CAS No. 56-57-5), N4-Aminocytidine (CAS no. 57294-74-3), sodium azide (CAS no. 26628-22-8), N-ethyl-N-nitrosourea (ENU) (CAS no. 759-73-9), N-methyl-N-nitrosourea (MNU) (CAS no. 820-60-0), 5-azacytidine (CAS no. 320-67-2), cumene hydroperoxide (CHP) (CAS no. 80-15-9), ethyl methanesulfonate (EMS) (CAS no. 62-50-0), N-ethyl-N-nitro-N-nitrosoguanidine (ENNG) (CAS no. 4245-77-6), N-methyl-N-nitro-N-nitrosoguanidine (MNNG) (CAS no.

70-25-7), 5-diazouracil (CAS no. 2435-76-9) and t-butyl hydroperoxide (BHP) (CAS no. 75-91-2). Additional mutagens can be used in continuous evolution procedures as provided herein, and the invention is not limited in this respect.

Ideally, a mutagen is used at a concentration or level of exposure that induces a desired mutation rate in a given host cell or viral vector population, but is not significantly toxic to the host cells used within the average time frame a host cell is exposed to the mutagen or the time a host cell is present in the host cell flow before being replaced by a fresh host cell.

The term "mutagenesis plasmid," as used herein, refers to a plasmid comprising a gene encoding a gene product that acts as a mutagen. In some embodiments, the gene encodes a DNA polymerase lacking a proofreading capability. In some embodiments, the gene is a gene involved in the bacterial SOS stress response, for example, a UmuC, UmuD', or RecA gene.

Host Cells

The term "host cell," as used herein, refers to a cell that can host a viral vector useful for a continuous evolution process as provided herein. A cell can host a viral vector if it supports expression of genes of viral vector, replication of the viral genome, and/or the generation of viral particles. One criterion to determine whether a cell is a suitable host cell for a given viral vector is to determine whether the cell can support the viral life cycle of a wild-type viral genome that the viral vector is derived from. For example, if the viral vector is a modified M13 phage genome, as provided in some embodiments described herein, then a suitable host cell would be any cell that can support the wild-type M13 phage life cycle. Suitable host cells for viral vectors useful in continuous evolution processes are well known to those of skill in the art, and the invention is not limited in this respect.

In some embodiments, modified viral vectors are used in continuous evolution processes as provided herein. In some embodiments, such modified viral vectors lack a gene required for the generation of infectious viral particles. In some such embodiments, a suitable host cell is a cell comprising the gene required for the generation of infectious viral particles, for example, under the control of a constitutive or a conditional promoter (e.g., in the form of an accessory plasmid, as described herein). In some embodiments, the viral vector used lacks a plurality of viral genes. In some such embodiments, a suitable host cell is a cell that comprises a helper construct providing the viral genes required for the generation of viral particles. A cell is not required to actually support the life cycle of a viral vector used in the methods provided herein. For example, a cell comprising a gene required for the generation of infectious viral particles under the control of a conditional promoter may not support the life cycle of a viral vector that does not comprise a gene of interest able to activate the promoter, but it is still a suitable host cell for such a viral vector. In some embodiments, the viral vector is a phage and the host cell is a bacterial cell. In some embodiments, the host cell is an $E.$ $coli$ cell. Suitable $E. coli$ host strains will be apparent to those of skill in the art, and include, but are not limited to, New England Biolabs (NEB) Turbo, Top10F', DH12S, ER2738, ER2267, and XL1-Blue MRF'. These strain names are art recognized and the genotype of these strains has been well characterized. It should be understood that the above strains are exemplary only and that the invention is not limited in this respect.

The term "fresh," as used herein interchangeably with the terms "non-infected" or "uninfected" in the context of host cells, refers to a host cell that has not been infected by a viral vector comprising a gene of interest as used in a continuous evolution process provided herein. A fresh host cell can, however, have been infected by a viral vector unrelated to the vector to be evolved or by a vector of the same or a similar type but not carrying the gene of interest.

In some embodiments, the host cell is a prokaryotic cell, for example, a bacterial cell. In some embodiments, the host cell is an $E. coli$ cell. In some embodiments, the host cell is a eukaryotic cell, for example, a yeast cell, an insect cell, or a mammalian cell. The type of host cell, will, of course, depend on the viral vector employed, and suitable host cell/viral vector combinations will be readily apparent to those of skill in the art.

In some PACE embodiments, for example, in embodiments employing an M13 selection phage, the host cells are $E. coli$ cells expressing the Fertility factor, also commonly referred to as the F factor, sex factor, or F-plasmid. The F-factor is a bacterial DNA sequence that allows a bacterium to produce a sex pilus necessary for conjugation and is essential for the infection of $E. coli$ cells with certain phage, for example, with M13 phage. For example, in some embodiments, the host cells for M13-PACE are of the genotype F'proA$^+$B$^+$ Δ(lacIZY) zzf::Tn10(TetR)/endA1 recA1 galE15 galK16 nupG rpsL ΔlacIZYA araD139 Δ(ara, leu)7697 mcrA Δ(mrr-hsdRMS-mcrBC) proBA::pir116λ$^-$ Lagoons, Cellstats, Turbidostats The term "lagoon," as used herein, refers to a vessel through which a flow of host cells is directed. When used for a continuous evolution process as provided herein, a lagoon typically holds a population of host cells and a population of viral vectors replicating within the host cell population, wherein the lagoon comprises an outflow through which host cells are removed from the lagoon and an inflow through which fresh host cells are introduced into the lagoon, thus replenishing the host cell population. In some embodiments, the flow of cells through the lagoon is regulated to result in an essentially constant number of host cells within the lagoon. In some embodiments, the flow of cells through the lagoon is regulated to result in an essentially constant number of fresh host cells within the lagoon.

The term "cellstat," as used herein, refers to a culture vessel comprising host cells, in which the number of cells is substantially constant over time.

The term "turbidostat," as used herein, refers to a culture vessel comprising host cells in suspension culture, in which the turbidity of the culture medium is substantially essentially constant over time. In some embodiments, the turbidity of a suspension culture, for example, of bacterial cells, is a measure for the cell density in the culture medium. In some embodiments, a turbidostat comprises an inflow of fresh media and an outflow, and a controller that regulates the flow into and/or out of the turbidostat based on the turbidity of the suspension culture in the turbidostat.

DETAILED DESCRIPTION OF CERTAIN EMBODIMENTS OF THE INVENTION

Some aspects of this invention provide methods for the continuous evolution of a nucleic acid, for example, of a gene of interest. Some aspects of this invention provide experimental configurations, systems, apparatuses, reagents, and materials for the continuous evolution methods described herein. Vectors, vector systems, and kits for continuous evolution as described herein are also provided.

Continuous Evolution Methods

The continuous evolution methods provided herein allow for a gene of interest in a viral vector to be evolved over multiple generations of viral life cycles in a flow of host cells to acquire a desired function or activity.

Some aspects of this invention provide a method of continuous evolution of a gene of interest, comprising (a) contacting a population of host cells with a population of viral vectors comprising the gene of interest, wherein (1) the host cell is amenable to infection by the viral vector; (2) the host cell expresses viral genes required for the generation of viral particles; (3) the expression of at least one viral gene required for the production of an infectious viral particle is dependent on a function of the gene of interest; and (4) the viral vector allows for expression of the protein in the host cell, and can be replicated and packaged into a viral particle by the host cell. In some embodiments, the method comprises (b) contacting the host cells with a mutagen. In some embodiments, the method further comprises (c) incubating the population of host cells under conditions allowing for viral replication and the production of viral particles, wherein host cells are removed from the host cell population, and fresh, uninfected host cells are introduced into the population of host cells, thus replenishing the population of host cells and creating a flow of host cells. The cells are incubated in all embodiments under conditions allowing for the gene of interest to acquire a mutation. In some embodiments, the method further comprises (d) isolating a mutated version of the viral vector, encoding an evolved gene product (e.g., protein), from the population of host cells.

In some embodiments, a method of phage-assisted continuous evolution is provided comprising (a) contacting a population of bacterial host cells with a population of phages that comprise a gene of interest to be evolved and that are deficient in a gene required for the generation of infectious phage, wherein (1) the phage allows for expression of the gene of interest in the host cells; (2) the host cells are suitable host cells for phage infection, replication, and packaging; and (3) the host cells comprise an expression construct encoding the gene required for the generation of infectious phage, wherein expression of the gene is dependent on a function of a gene product of the gene of interest. In some embodiments the method further comprises (b) incubating the population of host cells under conditions allowing for the mutation of the gene of interest, the production of infectious phage, and the infection of host cells with phage, wherein infected cells are removed from the population of host cells, and wherein the population of host cells is replenished with fresh host cells that have not been infected by the phage. In some embodiments, the method further comprises (c) isolating a mutated phage replication product encoding an evolved protein from the population of host cells.

In some embodiments, the viral vector or the phage is a filamentous phage, for example, an M13 phage, such as an M13 selection phage as described in more detail elsewhere herein. In some such embodiments, the gene required for the production of infectious viral particles is the M13 gene III (gIII).

In some embodiments, the viral vector infects mammalian cells. In some embodiments, the viral vector is a retroviral vector. In some embodiments, the viral vector is a vesicular stomatitis virus (VSV) vector. As a dsRNA virus, VSV has a high mutation rate, and can carry cargo, including a gene of interest, of up to 4.5 kb in length. The generation of infectious VSV particles requires the envelope protein VSV-G, a viral glycoprotein that mediates phosphatidylserine attachment and cell entry. VSV can infect a broad spectrum of host cells, including mammalian and insect cells. VSV is therefore a highly suitable vector for continuous evolution in human, mouse, or insect host cells. Similarly, other retroviral vectors that can be pseudotyped with VSV-G envelope protein are equally suitable for continuous evolution processes as described herein.

It is known to those of skill in the art that many retroviral vectors, for example, Murine Leukemia Virus vectors, or Lentiviral vectors can efficiently be packaged with VSV-G envelope protein as a substitute for the virus's native envelope protein. In some embodiments, such VSV-G packagable vectors are adapted for use in a continuous evolution system in that the native envelope (env) protein (e.g., VSV-G in VSVS vectors, or env in MLV vectors) is deleted from the viral genome, and a gene of interest is inserted into the viral genome under the control of a promoter that is active in the desired host cells. The host cells, in turn, express the VSV-G protein, another env protein suitable for vector pseudotyping, or the viral vector's native env protein, under the control of a promoter the activity of which is dependent on an activity of a product encoded by the gene of interest, so that a viral vector with a mutation leading to an increased activity of the gene of interest will be packaged with higher efficiency than a vector with baseline or a loss-of-function mutation.

In some embodiments, mammalian host cells are subjected to infection by a continuously evolving population of viral vectors, for example, VSV vectors comprising a gene of interest and lacking the VSV-G encoding gene, wherein the host cells comprise a gene encoding the VSV-G protein under the control of a conditional promoter. Such retrovirus-bases system could be a two-vector system (the viral vector and an expression construct comprising a gene encoding the envelope protein), or, alternatively, a helper virus can be employed, for example, a VSV helper virus. A helper virus typically comprises a truncated viral genome deficient of structural elements required to package the genome into viral particles, but including viral genes encoding proteins required for viral genome processing in the host cell, and for the generation of viral particles. In such embodiments, the viral vector-based system could be a three-vector system (the viral vector, the expression construct comprising the envelope protein driven by a conditional promoter, and the helper virus comprising viral functions required for viral genome propagation but not the envelope protein). In some embodiments, expression of the five genes of the VSV genome from a helper virus or expression construct in the host cells, allows for production of infectious viral particles carrying a gene of interest, indicating that unbalanced gene expression permits viral replication at a reduced rate, suggesting that reduced expression of VSV-G would indeed serve as a limiting step in efficient viral production.

One advantage of using a helper virus is that the viral vector can be deficient in genes encoding proteins or other functions provided by the helper virus, and can, accordingly, carry a longer gene of interest. In some embodiments, the helper virus does not express an envelope protein, because expression of a viral envelope protein is known to reduce the infectability of host cells by some viral vectors via receptor interference. Viral vectors, for example retroviral vectors, suitable for continuous evolution processes, their respective envelope proteins, and helper viruses for such vectors, are well known to those of skill in the art. For an overview of some exemplary viral genomes, helper viruses, host cells, and envelope proteins suitable for continuous evolution procedures as described herein, see Coffin et al., Retroviruses, CSHL Press 1997, ISBN0-87969-571-4, incorporated herein in its entirety.

In some embodiments, the incubating of the host cells is for a time sufficient for at least 10, at least 20, at least 30, at least 40, at least 50, at least 100, at least 200, at least 300, at least 400, at least, 500, at least 600, at least 700, at least 800, at least 900, at least 1000, at least 1250, at least 1500, at least 1750, at least 2000, at least 2500, at least 3000, at least 4000, at least 5000, at least 7500, at least 10000, or more consecutive viral life cycles. In certain embodiments, the viral vector is an M13 phage, and the length of a single viral life cycle is about 10-20 minutes.

In some embodiments, the cells are contacted and/or incubated in suspension culture. For example, in some embodiments, bacterial cells are incubated in suspension culture in liquid culture media. Suitable culture media for bacterial suspension culture will be apparent to those of skill in the art, and the invention is not limited in this regard. See, for example, *Molecular Cloning: A Laboratory Manual*, 2nd Ed., ed. by Sambrook, Fritsch, and Maniatis (Cold Spring Harbor Laboratory Press: 1989); Elizabeth Kutter and Alexander Sulakvelidze: *Bacteriophages: Biology and Applications*. CRC Press; 1$^{st}$ edition (December 2004), ISBN: 0849313368; Martha R. J. Clokie and Andrew M. Kropinski: *Bacteriophages: Methods and Protocols, Volume 1: Isolation, Characterization, and Interactions (Methods in Molecular Biology)* Humana Press; 1$^{st}$ edition (December, 2008), ISBN: 1588296822; Martha R. J. Clokie and Andrew M. Kropinski: *Bacteriophages: Methods and Protocols, Volume 2: Molecular and Applied Aspects (Methods in Molecular Biology)* Humana Press; 1$^{st}$ edition (December 2008), ISBN: 1603275649; all of which are incorporated herein in their entirety by reference for disclosure of suitable culture media for bacterial host cell culture). Suspension culture typically requires the culture media to be agitated, either continuously or intermittently. This is achieved, in some embodiments, by agitating or stirring the vessel comprising the host cell population. In some embodiments, the outflow of host cells and the inflow of fresh host cells is sufficient to maintain the host cells in suspension. This in particular, if the flow rate of cells into and/or out of the lagoon is high.

In some embodiments, a viral vector/host cell combination is chosen in which the life cycle of the viral vector is significantly shorter than the average time between cell divisions of the host cell. Average cell division times and viral vector life cycle times are well known in the art for many cell types and vectors, allowing those of skill in the art to ascertain such host cell/vector combinations. In certain embodiments, host cells are being removed from the population of host cells contacted with the viral vector at a rate that results in the average time of a host cell remaining in the host cell population before being removed to be shorter than the average time between cell divisions of the host cells, but to be longer than the average life cycle of the viral vector employed. The result of this is that the host cells, on average, do not have sufficient time to proliferate during their time in the host cell population while the viral vectors do have sufficient time to infect a host cell, replicate in the host cell, and generate new viral particles during the time a host cell remains in the cell population. This assures that the only replicating nucleic acid in the host cell population is the viral vector, and that the host cell genome, the accessory plasmid, or any other nucleic acid constructs cannot acquire mutations allowing for escape from the selective pressure imposed.

For example, in some embodiments, the average time a host cell remains in the host cell population is about 10, about 11, about 12, about 13, about 14, about 15, about 16, about 17, about 18, about 19, about 20, about 21, about 22, about 23, about 24, about 25, about 30, about 35, about 40, about 45, about 50, about 55, about 60, about 70, about 80, about 90, about 100, about 120, about 150, or about 180 minutes.

In some embodiments, the average time a host cell remains in the host cell population depends on how fast the host cells divide and how long infection (or conjugation) requires. In general, the flow rate should be faster than the average time required for cell division, but slow enough to allow viral (or conjugative) propagation. The former will vary, for example, with the media type, and can be delayed by adding cell division inhibitor antibiotics (FtsZ inhibitors in *E. coli*, etc.). Since the limiting step in continuous evolution is production of the protein required for gene transfer from cell to cell, the flow rate at which the vector washes out will depend on the current activity of the gene(s) of interest. In some embodiments, titratable production of the protein required for the generation of infectious particles, as described herein, can mitigate this problem. In some embodiments, an indicator of phage infection allows computer-controlled optimization of the flow rate for the current activity level in real-time.

In some embodiments, the host cell population is continuously replenished with fresh, uninfected host cells. In some embodiments, this is accomplished by a steady stream of fresh host cells into the population of host cells. In other embodiments, however, the inflow of fresh host cells into the lagoon is semi-continuous or intermittent (e.g., batch-fed). In some embodiments, the rate of fresh host cell inflow into the cell population is such that the rate of removal of cells from the host cell population is compensated. In some embodiments, the result of this cell flow compensation is that the number of cells in the cell population is substantially constant over the time of the continuous evolution procedure. In some embodiments, the portion of fresh, uninfected cells in the cell population is substantially constant over the time of the continuous evolution procedure. For example, in some embodiments, about 10%, about 15%, about 20%, about 25%, about 30%, about 40%, about 50%, about 60%, about 70%, about 75%, about 80%, or about 90% of the cells in the host cell population are not infected by virus. In general, the faster the flow rate of host cells is, the smaller the portion of cells in the host cell population that are infected will be. However, faster flow rates allow for more transfer cycles, e.g., viral life cycles, and, thus, for more generations of evolved vectors in a given period of time, while slower flow rates result in a larger portion of infected host cells in the host cell population and therefore a larger library size at the cost of slower evolution. In some embodiments, the range of effective flow rates is invariably bounded by the cell division time on the slow end and vector washout on the high end In some embodiments, the viral load, for example, as measured in infectious viral particles per volume of cell culture media is substantially constant over the time of the continuous evolution procedure.

In some embodiments, the fresh host cells comprise the accessory plasmid required for selection of viral vectors, for example, the accessory plasmid comprising the gene required for the generation of infectious phage particles that is lacking from the phages being evolved. In some embodiments, the host cells are generated by contacting an uninfected host cell with the relevant vectors, for example, the accessory plasmid and, optionally, a mutagenesis plasmid, and growing an amount of host cells sufficient for the replenishment of the host cell population in a continuous evolution experiment. Methods for the introduction of plasmids and other gene constructs into host cells are well known to those of skill in the art and the invention is not limited in this respect. For bacterial host cells, such methods include, but are not limited to electroporation and heat-shock of competent cells. In some embodiments, the accessory plasmid comprises a selection marker, for example, an antibiotic resistance marker, and the fresh host cells are grown in the presence of the respective antibiotic to ensure the presence of the plasmid in the host cells. Where multiple plasmids are present, different markers are typically used. Such selection markers and their use in cell culture are known to those of skill in the art, and the invention is not limited in this respect.

In some embodiments, the host cell population in a continuous evolution experiment is replenished with fresh host cells growing in a parallel, continuous culture. In some embodiments, the cell density of the host cells in the host cell population contacted with the viral vector and the density of the fresh host cell population is substantially the same.

Typically, the cells being removed from the cell population contacted with the viral vector comprise cells that are infected with the viral vector and uninfected cells. In some embodiments, cells are being removed from the cell populations continuously, for example, by effecting a continuous outflow of the cells from the population. In other embodiments, cells are removed semi-continuously or intermittently from the population. In some embodiments, the replenishment of fresh cells will match the mode of removal of cells from the cell population, for example, if cells are continuously removed, fresh cells will be continuously introduced. However, in some embodiments, the modes of replenishment and removal may be mismatched, for example, a cell population may be continuously replenished with fresh cells, and cells may be removed semi-continuously or in batches.

In some embodiments, the rate of fresh host cell replenishment and/or the rate of host cell removal is adjusted based on quantifying the host cells in the cell population. For example, in some embodiments, the turbidity of culture media comprising the host cell population is monitored and, if the turbidity falls below a threshold level, the ratio of host cell inflow to host cell outflow is adjusted to effect an increase in the number of host cells in the population, as manifested by increased cell culture turbidity. In other embodiments, if the turbidity rises above a threshold level, the ratio of host cell inflow to host cell outflow is adjusted to effect a decrease in the number of host cells in the population, as manifested by decreased cell culture turbidity. Maintaining the density of host cells in the host cell population within a specific density range ensures that enough host cells are available as hosts for the evolving viral vector population, and avoids the depletion of nutrients at the cost of viral packaging and the accumulation of cell-originated toxins from overcrowding the culture.

In some embodiments, the cell density in the host cell population and/or the fresh host cell density in the inflow is about $10^2$ cells/ml to about $10^{12}$ cells/ml. In some embodiments, the host cell density is about $10^2$ cells/ml, about $10^3$ cells/ml, about $10^4$ cells/ml, about $10^5$ cells/ml, about $5 \cdot 10^5$ cells/ml, about $10^6$ cells/ml, about $5 \cdot 10^6$ cells/ml, about $10^7$ cells/ml, about $5 \cdot 10^7$ cells/ml, about $10^8$ cells/ml, about $5 \cdot 10^8$ cells/ml, about $10^9$ cells/ml, about $5 \cdot 10^9$ cells/ml, about $10^{10}$ cells/ml, or about $5 \cdot 10^{10}$ cells/ml. In some embodiments, the host cell density is more than about $10^{10}$ cells/ml.

In some embodiments, the host cell population is contacted with a mutagen. In some embodiments, the cell population contacted with the viral vector (e.g., the phage), is continuously exposed to the mutagen at a concentration that allows for an increased mutation rate of the gene of interest, but is not significantly toxic for the host cells during their exposure to the mutagen while in the host cell population. In other embodiments, the host cell population is contacted with the mutagen intermittently, creating phases of increased mutagenesis, and accordingly, of increased viral vector diversification. For example, in some embodiments, the host cells are exposed to a concentration of mutagen sufficient to generate an increased rate of mutagenesis in the gene of interest for about 10%, about 20%, about 50%, or about 75% of the time.

In some embodiments, the host cells comprise a mutagenesis expression construct, for example, in the case of bacterial host cells, a mutagenesis plasmid. In some embodiments, the mutagenesis plasmid comprises a gene expression cassette encoding a mutagenesis-promoting gene product, for example, a proofreading-impaired DNA polymerase. In other embodiments, the mutagenesis plasmid, including a gene involved in the SOS stress response, (e.g., UmuC, UmuD', and/or RecA). In some embodiments, the mutagenesis-promoting gene is under the control of an inducible promoter. Suitable inducible promoters are well known to those of skill in the art and include, for example, arabinose-inducible promoters, tetracycline or doxycyclin-inducible promoters, and tamoxifen-inducible promoters. In some embodiments, the host cell population is contacted with an inducer of the inducible promoter in an amount sufficient to effect an increased rate of mutagenesis. For example, in some embodiments, a bacterial host cell population is provided in which the host cells comprise a mutagenesis plasmid in which a dnaQ926, UmuC, UmuD', and RecA expression cassette is controlled by an arabinose-inducible promoter. In some such embodiments, the population of host cells is contacted with the inducer, for example, arabinose in an amount sufficient to induce an increased rate of mutation.

The use of an inducible mutagenesis plasmid allows one to generate a population of fresh, uninfected host cells in the absence of the inducer, thus avoiding an increased rate of mutation in the fresh host cells before they are introduced into the population of cells contacted with the viral vector. Once introduced into this population, however, these cells can then be induced to support an increased rate of mutation, which is particularly useful in some embodiments of continuous evolution. For example, in some embodiments, the host cell comprise a mutagenesis plasmid as described herein, comprising an arabinose-inducible promoter driving expression of dnaQ926, UmuC, UmuD', and RecA730 from a pBAD promoter (see, e.g., Khlebnikov A, Skaug T, Keasling J D. *Modulation of gene expression from the arabinose-inducible araBAD promoter*. J Ind Microbiol Biotechnol. 2002 July; 29(1):34-7; incorporated herein by reference for disclosure of a pBAD promoter). In some embodiments, the fresh host cells are not exposed to arabinose, which activates expression of the above identified genes and, thus, increases the rate of mutations in the arabinose-exposed cells, until the host cells reach the lagoon in which the population of selection phage replicates. Accordingly, in some embodiments, the mutation rate in the host cells is normal until they become part of the host cell population in the lagoon, where they are exposed to the inducer (e.g., arabinose) and, thus, to increased mutagenesis. In some embodiments, a method of continuous evolution is provided that includes a phase of diversifying the population of viral vectors by mutagenesis, in which the cells are incubated under conditions suitable for mutagenesis of the viral vector in the absence of stringent selection for the mutated replication product of the viral vector encoding the evolved protein. This is particularly useful in embodiments in which a desired function to be evolved is not merely an increase in an already present function, for example, an increase in the transcriptional activation rate of a transcription factor, but the acquisition of a function not present in the gene of interest at the outset of the evolution procedure. A step of diversifying the pool of mutated versions of the gene of interest within the population of viral vectors, for example, of phage, allows for an increase in the chance to find a mutation that conveys the desired function.

In some embodiments, diversifying the viral vector population is achieved by providing a flow of host cells that does not select for gain-of-function mutations in the gene of interest for replication, mutagenesis, and propagation of the population of viral vectors. In some embodiments, the host cells are host cells that express all genes required for the generation of infectious viral particles, for example, bacterial cells that express a complete helper phage, and, thus, do not impose selective pressure on the gene of interest. In other embodiments, the host cells comprise an accessory plasmid comprising a conditional promoter with a baseline activity sufficient to support viral vector propagation even in the absence of significant gain-of-function mutations of the gene of interest. This can be achieved by using a "leaky" conditional promoter, by using a high-copy number accessory plasmid, thus amplifying baseline leakiness, and/or by using a conditional promoter on which the initial version of the gene of interest effects a low level of activity while a desired gain-of-function mutation effects a significantly higher activity.

For example, as described in more detail in the Example section, in some embodiments, a population of host cells comprising a high-copy accessory plasmid with a gene required for the generation of infectious phage particles is contacted with a selection phage comprising a gene of interest, wherein the accessory plasmid comprises a conditional promoter driving expression of the gene required for the generation from a conditional promoter, the activity of which is dependent on the activity of a gene product encoded by the gene of interest. In some such embodiments, a low stringency selection phase can be achieved by designing the conditional promoter in a way that the initial gene of interest exhibits some activity on that promoter. For example, if a transcriptional activator, such as a T7RNAP or a transcription factor is to be evolved to recognize a non-native target DNA sequence (e.g., a T3RNAP promoter sequence, on which T7RNAP has no activity), a low-stringency accessory plasmid can be designed to comprise a conditional promoter in which the target sequence comprises a desired characteristic, but also retains a feature of the native recognition sequence that allows the transcriptional activator to recognize the target sequence, albeit with less efficiency than its native target sequence. Initial exposure to such a low-stringency accessory plasmid comprising a hybrid target sequence (e.g., a T7/T3 hybrid promoter, with some features of the ultimately desired target sequence and some of the native target sequence) allows the population of phage vectors to diversify by acquiring a plurality of mutations that are not immediately selected against based on the permissive character of the accessory plasmid. Such a diversified population of phage vectors can then be exposed to a stringent selection accessory plasmid, for example, a plasmid comprising in its conditional promoter the ultimately desired target sequence that does not retain a feature of the native target sequence, thus generating a strong negative selective pressure against phage vectors that have not acquired a mutation allowing for recognition of the desired target sequence.

In some embodiments, an initial host cell population contacted with a population of evolving viral vectors is replenished with fresh host cells that are different from the host cells in the initial population. For example, in some embodiments, the initial host cell population is made of host cells comprising a low-stringency accessory plasmid, or no such plasmid at all, or are permissible for viral infection and propagation. In some embodiments, after diversifying the population of viral vectors in the low-stringency or no-selection host cell population, fresh host cells are introduced into the host cell population that impose a more stringent selective pressure for the desired function of the gene of interest. For example, in some embodiments, the secondary fresh host cells are not permissible for viral replication and propagation anymore. In some embodiments, the stringently selective host cells comprise an accessory plasmid in which the conditional promoter exhibits none or only minimal baseline activity, and/or which is only present in low or very low copy numbers in the host cells.

Such methods involving host cells of varying selective stringency allow for harnessing the power of continuous evolution methods as provided herein for the evolution of functions that are completely absent in the initial version of the gene of interest, for example, for the evolution of a transcription factor recognizing a foreign target sequence that a native transcription factor, used as the initial gene of interest, does not recognize at all. Or, for another example, the recognition of a desired target sequence by a DNA-binding protein, a recombinase, a nuclease, a zinc-finger protein, or an RNA-polymerase, that does not bind to or does not exhibit any activity directed towards the desired target sequence.

In some embodiments, negative selection is applied during a continuous evolution method as described herein, by penalizing undesired activities. In some embodiments, this is achieved by causing the undesired activity to interfere with pIII production. For example, expression of an antisense RNA complementary to the gIII RBS and/or start codon is one way of applying negative selection, while expressing a protease (e.g., TEV) and engineering the protease recognition sites into pIII is another.

In some embodiments, negative selection is applied during a continuous evolution method as described herein, by penalizing the undesired activities of evolved products. This is useful, for example, if the desired evolved product is an enzyme with high specificity, for example, a transcription factor or protease with altered, but not broadened, specificity. In some embodiments, negative selection of an undesired activity is achieved by causing the undesired activity to interfere with pIII production, thus inhibiting the propagation of phage genomes encoding gene products with an undesired activity. In some embodiments, expression of a dominant-negative version of pIII or expression of an antisense RNA complementary to the gIII RBS and/or gIII start codon is linked to the presence of an undesired activity. In some embodiments, a nuclease or protease cleavage site, the recognition or cleavage of which is undesired, is inserted into a pIII transcript sequence or a pIII amino acid sequence, respectively. In some embodiments, a transcriptional or translational repressor is used that represses expression of a dominant negative variant of pIII and comprises a protease cleavage site the recognition or cleaveage of which is undesired.

In some embodiments, counter-selection against activity on non-target substrates is achieved by linking undesired evolved product activities to the inhibition of phage propagation. For example, in some embodiments, in which a transcription factor is evolved to recognize a specific target sequence, but not an undesired off-target sequence, a negative selection cassette is employed, comprising a nucleic acid sequence encoding a dominant-negative version of pIII (pIII-neg) under the control of a promoter comprising the off-target sequence. If an evolution product recognizes the off-target sequence, the resulting phage particles will incorporate pIII-neg, which results in an inhibition of phage infective potency and phage propagation, thus constituting a selective disadvantage for any phage genomes encoding an evolution product exhibiting the undesired, off-target activity, as compared to evolved products not exhibiting such an activity. In some embodiments, a dual selection strategy is applied during a continuous evolution experiment, in which both positive selection and negative selection constructs are present in the host cells. In some such embodiments, the positive and negative selection constructs are situated on the same plasmid, also referred to as a dual selection accessory plasmid.

For example, in some embodiments, a dual selection accessory plasmid is employed comprising a positive selection cassette, comprising a pIII-encoding sequence under the control of a promoter comprising a target nucleic acid sequence, and a negative selection cassette, comprising a pIII-neg encoding cassette under the control of a promoter comprising an off-target nucleic acid sequence. One advantage of using a simultaneous dual selection strategy is that the selection stringency can be fine-tuned based on the activity or expression level of the negative selection construct as compared to the positive selection construct. Another advantage of a dual selection strategy is the selection is not dependent on the presence or the absence of a desired or an undesired activity, but on the ratio of desired and undesired activities, and, thus, the resulting ratio of pIII and pIII-neg that is incorporated into the respective phage particle.

Some aspects of this invention provide or utilize a dominant negative variant of pIII (pIII-neg). These aspects are based on the surprising discovery that a pIII variant that comprises the two N-terminal domains of pIII and a truncated, termination-incompetent C-terminal domain is not only inactive but is a dominant-negative variant of pIII. A pIII variant comprising the two N-terminal domains of pIII and a truncated, termination-incompetent C-terminal domain was described in Bennett, N. J.; Rakonjac, J., Unlocking of the filamentous bacteriophage virion during infection is mediated by the C domain of pIII. *Journal of Molecular Biology* 2006, 356 (2), 266-73; the entire contents of which are incorporated herein by reference. However, the dominant negative property of such pIII variants has not been previously described. Some aspects of this invention are based on the surprising discovery that a pIII-neg variant as provided herein is efficiently incorporated into phage particles, but it does not catalyze the unlocking of the particle for entry during infection, rendering the respective phage noninfectious even if wild type pIII is present in the same phage particle. Accordingly, such pIII-neg variants are useful for devising a negative selection strategy in the context of PACE, for example, by providing an expression construct comprising a nucleic acid sequence encoding a pIII-neg variant under the control of a promoter comprising a recognition motif, the recognition of which is undesired. In other embodiments, pIII-neg is used in a positive selection strategy, for example, by providing an expression construct in which a pIII-neg encoding sequence is controlled by a promoter comprising a nuclease target site or a repressor recognition site, the recognition of either one is desired.

Positive and negative selection strategies can further be designed to link non-DNA directed activities to phage propagation efficiency. For example, protease activity towards a desired target protease cleavage site can be linked to pIII expression by devising a repressor of gene expression that can be inactivated by a protease recognizing the target site. In some embodiments, pIII expression is driven by a promoter comprising a binding site for such a repressor. Suitable transcriptional repressors are known to those in the art, and one exemplary repressor is the lambda repressor protein, that efficiently represses the lambda promoter pR and can be modified to include a desired protease cleavage site (see, e.g., Sices, H. J.; Kristie, T. M., A genetic screen for the isolation and characterization of site-specific proteases. *Proc Natl Acad Sci USA* 1998, 95 (6), 2828-33; and Sices, H. J.; Leusink, M. D.; Pacheco, A.; Kristie, T. M., Rapid genetic selection of inhibitor-resistant protease mutants: clinically relevant and novel mutants of the HIV protease. *AIDS Res Hum Retroviruses* 2001, 17 (13), 1249-55, the entire contents of each of which are incorporated herein by reference). The lambda repressor (cI) contains an N-terminal DNA binding domain and a C-terminal dimerization domain. These two domains are connected by a flexible linker. Efficient transcriptional repression requires the dimerization of cI, and, thus, cleavage of the linker connecting dimerization and binding domains results in abolishing the repressor activity of cI.

Some embodiments provide a pIII expression construct that comprises a pR promoter (containing cI binding sites) driving expression of pIII. When expressed together with a modified cI comprising a desired protease cleavage site in the linker sequence connecting dimerization and binding domains, the cI molecules will repress pIII transcription in the absence of the desired protease activity, and this repression will be abolished in the presence of such activity, thus providing a linkage between protease cleavage activity and an increase in pIII expression that is useful for positive PACE protease selection. Some embodiments provide a negative selection strategy against undesired protease activity in PACE evolution products. In some embodiments, the negative selection is conferred by an expression cassette comprising a pIII-neg encoding nucleic acid under the control of a cI-repressed promoter. When co-expressed with a cI repressor protein comprising an undesired protease cleavage site, expression of pIII-neg will occur in cell harboring phage expressing a protease exhibiting protease activity towards the undesired target site, thus negatively selecting against phage encoding such undesired evolved products. A dual selection for protease target specificity can be achieved by co-expressing cI-repressible pIII and pIII-neg encoding expression constructs with orthogonal cI variants recognizing different DNA target sequences, and thus allowing for simultaneous expression without interfering with each other. Orthogonal cI variants in both dimerization specificity and DNA-binding specificity are known to those of skill in the art (see, e.g., Wharton, R. P.; Ptashne, M., Changing the binding specificity of a repressor by redesigning an alphahelix. *Nature* 1985, 316 (6029), 601-5; and Wharton, R. P.; Ptashne, M., A new-specificity mutant of 434 repressor that defines an amino acid-base pair contact. *Nature* 1987, 326 (6116), 888-91, the entire contents of each of which are incorporated herein by reference).

Other selection schemes for gene products having a desired activity are well known to those of skill in the art or will be apparent from the instant disclosure. Selection strategies that can be used in continuous evolution processes and methods as provided herein include, but are not limited to, selection strategies useful in two-hybrid screens. For example, the T7 RNAP selection strategy described in more detail elsewhere herein is an example of a promoter recognition selection strategy. Two-hybrid accessory plasmid set-ups further permit the evolution of protein-protein interactions, and accessory plasmids requiring site-specific recombinase activity for production of the protein required for the generation of infectious viral particles, for example, pIII, allow recombinases to be evolved to recognize any desired target site. A two-hybrid setup or a related one-hybrid setup can further be used to evolve DNA-binding proteins, while a three-hybrid setup can evolve RNA-protein interactions.

Biosynthetic pathways producing small molecules can also be evolved with a promoter or riboswitch (e.g., controlling gene III expression/translation) that is responsive to the presence of the desired small molecule. For example, a promoter that is transcribed only in the presence of butanol could be placed on the accessory plasmid upstream of gene III to optimize a biosynthetic pathway encoding the enzymes for butanol synthesis. A phage vector carrying a gene of interest that has acquired an activity boosting butanol synthesis would have a selective advantage over other phages in an evolving phage population that have not acquired such a gain-of-function. Alternatively, a chemical complementation system, for example, as described in Baker and Cornish, *PNAS*, 2002, incorporated herein by reference, can be used to evolve individual proteins or enzymes capable of bond formation reactions ( ). In other embodiments, a trans-splicing intron designed to splice itself into a particular target sequence can be evolved by expressing only the latter half of gene III from the accessory plasmid, preceded by the target sequence, and placing the other half (fused to the trans-splicing intron) on the selection phage. Successful splicing would reconstitute full-length pIII-encoding mRNA. Protease specificity and activity can be evolved by expressing pIII fused to a large protein from the accessory plasmid, separated by a linker containing the desired protease recognition site. Cleavage of the linker by active protease encoded by the selection phage would result in infectious pIII, while uncleaved pIII would be unable to bind due to the blocking protein. Further, As described, for example, by Malmborg and Borrebaeck 1997, a target antigen can be fused to the F pilus of a bacteria, blocking wild-type pIII from binding. Phage displaying antibodies specific to the antigen could bind and infect, yielding enrichments of >1000-fold in phage display. In some embodiments, this system can be adapted for continuous evolution, in that the accessory plasmid is designed to produce wild-type pIII to contact the tolA receptor and perform the actual infection (as the antibody-pIII fusion binds well but infects with low efficiency), while the selection phage encodes the pIII-antibody fusion protein. Progeny phage containing both types of pIII tightly adsorb to the F pilus through the antibody-antigen interaction, with the wild-type pIII contacting tolA and mediating high-efficiency infection. To allow propagation when the initial antibody-antigen interaction is weak, a mixture of host cells could flow into the lagoon: a small fraction expressing wild-type pili and serving as a reservoir of infected cells capable of propagating any selection phage regardless of activity, while the majority of cells requires a successful interaction, serving as the "reward" for any mutants that improve their binding affinity. This last system, in some embodiments, can evolve new antibodies that are effective against a target pathogen faster than the pathogen itself can evolve, since the evolution rates of PACE and other systems described herein are higher than those of human-specific pathogens, for example, those of human viruses.

Methods and strategies to design conditional promoters suitable for carrying out the selections strategies described herein are well known to those of skill in the art. Some exemplary design strategies are summarized in FIG. 3B. For an overview over exemplary suitable selection strategies and methods for designing conditional promoters driving the expression of a gene required for cell-cell gene transfer, e.g. gIII, see Vidal and Legrain, *Yeast n-hybrid review*, Nucleic Acid Research 27, 919 (1999), incorporated herein in its entirety.

Apparatus for Continued Evolution

The invention also provides apparatuses for continuous evolution of a nucleic acid. The core element of such an apparatus is a lagoon allowing for the generation of a flow of host cells in which a population of viral vectors can replicate and propagate. In some embodiments, the lagoon comprises a cell culture vessel comprising an actively replicating population of viral vectors, for example, phage vectors comprising a gene of interest, and a population of host cells, for example, bacterial host cells. In some embodiments, the lagoon comprises an inflow for the introduction of fresh host cells into the lagoon and an outflow for the removal of host cells from the lagoon. In some embodiments, the inflow is connected to a turbidostat comprising a culture of fresh host cells. In some embodiments, the outflow is connected to a waste vessel, or a sink. In some embodiments, the lagoon further comprises an inflow for the introduction of a mutagen into the lagoon. In some embodiments that inflow is connected to a vessel holding a solution of the mutagen. In some embodiments, the lagoon comprises an inflow for the introduction of an inducer of gene expression into the lagoon, for example, of an inducer activating an inducible promoter within the host cells that drives expression of a gene promoting mutagenesis (e.g., as part of a mutagenesis plasmid), as described in more detail elsewhere herein. In some embodiments, that inflow is connected to a vessel comprising a solution of the inducer, for example, a solution of arabinose.

In some embodiments, the lagoon comprises a population of viral vectors. In some embodiments, the lagoon comprises a population of viral vectors. In some embodiments, the viral vectors are phage, for example, M13 phages deficient in a gene required for the generation of infectious viral particles as described herein. In some such embodiments, the host cells are prokaryotic cells amenable to phage infection, replication, and propagation of phage, for example, host cells comprising an accessory plasmid comprising a gene required for the generation of infectious viral particles under the control of a conditional promoter as described herein.

In some embodiments, the lagoon comprises a controller for regulation of the inflow and outflow rates of the host cells, the inflow of the mutagen, and/or the inflow of the inducer. In some embodiments, a visual indicator of phage presence, for example, a fluorescent marker, is tracked and used to govern the flow rate, keeping the total infected population constant. In some embodiments, the visual marker is a fluorescent protein encoded by the phage genome, or an enzyme encoded by the phage genome that, once expressed in the host cells, results in a visually detectable change in the host cells. In some embodiments, the visual tracking of infected cells is used to adjust a flow rate to keep the system flowing as fast as possible without risk of vector washout.

In some embodiments, the expression of the gene required for the generation of infectious particles is titratable. In some embodiments, this is accomplished with an accessory plasmid producing pIII proportional to the amount of anhydrotetracycline added to the lagoon. Other In some embodiments, such a titrable expression construct can be combined with another accessory plasmid as described herein, allowing simultaneous selection for activity and titratable control of pIII. This permits the evolution of activities too weak to otherwise survive in the lagoon, as well as allowing neutral drift to escape local fitness peak traps. In some embodiments, negative selection is applied during a continuous evolution method as described herein, by penalizing undesired activities. In some embodiments, this is achieved by causing the undesired activity to interfere with pIII production. For example, expression of an antisense RNA complementary to the gIII RBS and/or start codon is one way of applying negative selection, while expressing a protease (e.g., TEV) and engineering the protease recognition sites into pIII is another.

In some embodiments, the apparatus comprises a turbidostat. In some embodiments, the turbidostat comprises a cell culture vessel in which the population of fresh host cells is situated, for example, in liquid suspension culture. In some embodiments, the turbidostat comprises an outflow that is connected to an inflow of the lagoon, allowing the introduction of fresh cells from the turbidostat into the lagoon. In some embodiments, the turbidostat comprises an inflow for the introduction of fresh culture media into the turbidostat. In some embodiments, the inflow is connected to a vessel comprising sterile culture media. In some embodiments, the turbidostat further comprises an outflow for the removal of host cells from the turbidostat. In some embodiments, that outflow is connected to a waste vessel or drain.

In some embodiments, the turbidostat comprises a turbidity meter for measuring the turbidity of the culture of fresh host cells in the turbidostat. In some embodiments, the turbidostat comprises a controller that regulated the inflow of sterile liquid media and the outflow into the waste vessel based on the turbidity of the culture liquid in the turbidostat.

In some embodiments, the lagoon and/or the turbidostat comprises a shaker or agitator for constant or intermittent agitation, for example, a shaker, mixer, stirrer, or bubbler, allowing for the population of host cells to be continuously or intermittently agitated and oxygenated.

In some embodiments, the controller regulates the rate of inflow of fresh host cells into the lagoon to be substantially the same (volume/volume) as the rate of outflow from the lagoon. In some embodiments, the rate of inflow of fresh host cells into and/or the rate of outflow of host cells from the lagoon is regulated to be substantially constant over the time of a continuous evolution experiment. In some embodiments, the rate of inflow and/or the rate of outflow is from about 0.1 lagoon volumes per hour to about 25 lagoon volumes per hour. In some embodiments, the rate of inflow and/or the rate of outflow is approximately 0.1 lagoon volumes per hour (lv/h), approximately 0.2 lv/h, approximately 0.25 lv/h, approximately 0.3 lv/h, approximately 0.4 lv/h, approximately 0.5 lv/h, approximately 0.6 lv/h, approximately 0.7 lv/h, approximately 0.75 lv/h, approximately 0.8 lv/h, approximately 0.9 lv/h, approximately 1 lv/h, approximately 2 lv/h, approximately 2.5 lv/h, approximately 3 lv/h, approximately 4 lv/h, approximately 5 lv/h, approximately 7.5 lv/h, approximately 10 lv/h, or more than 10 lv/h.

In some embodiments, the inflow and outflow rates are controlled based on a quantitative assessment of the population of host cells in the lagoon, for example, by measuring the cell number, cell density, wet biomass weight per volume, turbidity, or cell growth rate. In some embodiments, the lagoon inflow and/or outflow rate is controlled to maintain a host cell density of from about $10^2$ cells/ml to about $10^{12}$ cells/ml in the lagoon. In some embodiments, the inflow and/or outflow rate is controlled to maintain a host cell density of about $10^2$ cells/ml, about $10^3$ cells/ml, about $10^4$ cells/ml, about $10^5$ cells/ml, about $5\times10^5$ cells/ml, about $10^6$ cells/ml, about $5\times10^6$ cells/ml, about $10^7$ cells/ml, about $5\times10^7$ cells/ml, about $10^8$ cells/ml, about $5\times10^8$ cells/ml, about $10^9$ cells/ml, about $5\times10^9$ cells/ml, about $10^{10}$ cells/ml, about $5\times10^{10}$ cells/ml, or more than $5\times10^{10}$ cells/ml, in the lagoon. In some embodiments, the density of fresh host cells in the turbidostat and the density of host cells in the lagoon are substantially identical.

In some embodiments, the lagoon inflow and outflow rates are controlled to maintain a substantially constant number of host cells in the lagoon. In some embodiments, the inflow and outflow rates are controlled to maintain a substantially constant frequency of fresh host cells in the lagoon. In some embodiments, the population of host cells is continuously replenished with fresh host cells that are not infected by the phage. In some embodiments, the replenishment is semi-continuous or by batch-feeding fresh cells into the cell population.

In some embodiments, the lagoon volume is from approximately 1 ml to approximately 100 l, for example, the lagoon volume is approximately 1 ml, approximately 10 ml, approximately 50 ml, approximately 100 ml, approximately 200 ml, approximately 250 ml, approximately 500 ml, approximately 750 ml, approximately 1 l, approximately 2 ml, approximately 2.5 l, approximately 3 l, approximately 4 l, approximately 5 l, approximately 10 l, approximately 1 ml-10 ml, approximately 10 ml-50 ml, approximately 50 ml-100, approximately 100 ml-250 ml, approximately 250 ml-500 ml, approximately 500 ml-1 l, approximately 1 l-2 l, approximately 2 l-5 l, approximately 5 l-10 l, approximately 10-50 l, approximately 50-100 l, or more than 100 l.

In some embodiments, the lagoon and/or the turbidostat further comprises a heater and a thermostat controlling the temperature. In some embodiments, the temperature in the lagoon and/or the turbidostat is controlled to be from about 4° C. to about 55° C., preferably from about 25° C. to about 39° C., for example, about 37° C.

In some embodiments, the inflow rate and/or the outflow rate is controlled to allow for the incubation and replenishment of the population of host cells for a time sufficient for at least 10, at least 20, at least 30, at least 40, at least 50, at least 100, at least 200, at least 300, at least 400, at least, 500, at least 600, at least 700, at least 800, at least 900, at least 1000, at least 1250, at least 1500, at least 1750, at least 2000, at least 2500, at least 3000, at least 4000, at least 5000, at least 7500, at least 10000, or more consecutive viral vector or phage life cycles. In some embodiments, the time sufficient for one phage life cycle is about 10 minutes.

Therefore, in some embodiments, the time of the entire evolution procedure is about 12 hours, about 18 hours, about 24 hours, about 36 hours, about 48 hours, about 50 hours, about 3 days, about 4 days, about 5 days, about 6 days, about 7 days, about 10 days, about two weeks, about 3 weeks, about 4 weeks, or about 5 weeks.

For example, in some embodiments, a PACE apparatus is provided, comprising a lagoon of about 100 ml, or about 1 l volume, wherein the lagoon is connected to a turbidostat of about 0.5 l, 1 l, or 3 l volume, and to a vessel comprising an inducer for a mutagenesis plasmid, for example, arabinose, wherein the lagoon and the turbidostat comprise a suspension culture of *E. coli* cells at a concentration of about $5\times10^8$ cells/ml. In some embodiments, the flow of cells through the lagoon is regulated to about 3 lagoon volumes per hour. In some embodiments, cells are removed from the lagoon by continuous pumping, for example, by using a waste needle set at a height of the lagoon vessel that corresponds to a desired volume of fluid (e.g., about 100 ml, in the lagoon. In some embodiments, the host cells are *E. coli* cells comprising the F' plasmid, for example, cells of the genotype F'proA⁺B⁺ Δ(lacIZY) zzf::Tn10(TetR)/endA1 recA1 galE15 galK16 nupG rpsL ΔlacIZYA araD139 Δ(ara,leu)7697 mcrA Δ(mrr-hsdRMS-mcrBC) proBA::pir116λ⁻. In some embodiments, the selection phage comprises an M13 genome, in which the pIII-encoding region, or a part thereof, has been replaced with a gene of interest, for example, a coding region that is driven by a wild-type phage promoter. In some embodiments, the host cells comprise an accessory plasmid in which a gene encoding a protein required for the generation of infectious phage particles, for example, M13 pIII, is expressed from a conditional promoter as described in more detail elsewhere herein. In some embodiments, the host cells further comprise a mutagenesis plasmid, for example, a mutagenesis plasmid expressing a mutagenesis-promoting protein from an inducible promoter, such as an arabinose-inducible promoter. In some embodiments the apparatus is set up to provide fresh media to the turbidostat for the generation of a flow of cells of about 2-4 lagoon volumes per hour for about 3-7 days.

Vectors and Reagents

The invention provides viral vectors for the inventive continuous evolution processes. In some embodiments, phage vectors for phage-assisted continuous evolution are provided. In some embodiments, a selection phage is provided that comprises a phage genome deficient in at least one gene required for the generation of infectious phage particles and a gene of interest to be evolved.

For example, in some embodiments, the selection phage comprises an M13 phage genome deficient in a gene required for the generation of infectious M13 phage particles, for example, a full-length gIII. In some embodiments, the selection phage comprises a phage genome providing all other phage functions required for the phage life cycle except the gene required for generation of infectious phage particles. In some such embodiments, an M13 selection phage is provided that comprises a gI, gII, gIV, gV, gVI, gVII, gVIII, gIX, and a gX gene, but not a full-length gIII. In some embodiments, the selection phage comprises a 3'-fragment of gIII, but no full-length gIII. The 3'-end of gIII comprises a promoter (see FIG. 16) and retaining this promoter activity is beneficial, in some embodiments, for an increased expression of gVI, which is immediately downstream of the gIII 3'-promoter, or a more balanced (wild-type phage-like) ratio of expression levels of the phage genes in the host cell, which, in turn, can lead to more efficient phage production. In some embodiments, the 3'-fragment of gIII gene comprises the 3'-gIII promoter sequence. In some embodiments, the 3'-fragment of gIII comprises the last 180 bp, the last 150 bp, the last 125 bp, the last 100 bp, the last 50 bp, or the last 25 bp of gIII. In some embodiments, the 3'-fragment of gIII comprises the last 180 bp of gIII.

M13 selection phage is provided that comprises a gene of interest in the phage genome, for example, inserted downstream of the gVIII 3'-terminator and upstream of the gIII-3'-promoter. In some embodiments, an M13 selection phage is provided that comprises a multiple cloning site for cloning a gene of interest into the phage genome, for example, a multiple cloning site (MCS) inserted downstream of the gVIII 3'-terminator and upstream of the gIII-3'-promoter.

Some aspects of this invention provide a vector system for continuous evolution procedures, comprising of a viral vector, for example, a selection phage, and a matching accessory plasmid. In some embodiments, a vector system for phage-based continuous directed evolution is provided that comprises (a) a selection phage comprising a gene of interest to be evolved, wherein the phage genome is deficient in a gene required to generate infectious phage; and (b) an accessory plasmid comprising the gene required to generate infectious phage particle under the control of a conditional promoter, wherein the conditional promoter is activated by a function of a gene product encoded by the gene of interest.

In some embodiments, the selection phage is an M13 phage as described herein. For example, in some embodiments, the selection phage comprises an M13 genome including all genes required for the generation of phage particles, for example, gI, gII, gIV, gV, gVI, gVII, gVIII, gIX, and gX gene, but not a full-length gIII gene. In some embodiments, the selection phage genome comprises an F1 or an M13 origin of replication. In some embodiments, the selection phage genome comprises a 3'-fragment of gIII gene. In some embodiments, the selection phage comprises a multiple cloning site upstream of the gIII 3'-promoter and downstream of the gVIII 3'-terminator.

In some embodiments, the selection phage does not comprise a full length gVI. GVI is similarly required for infection as gIII and, thus, can be used in a similar fashion for selection as described for gIII herein. However, it was found that continuous expression of pIII renders some host cells resistant to infection by M13. Accordingly, it is desirable that pIII is produced only after infection. This can be achieved by providing a gene encoding pIII under the control of an inducible promoter, for example, an arabinose-inducible promoter as described herein, and providing the inducer in the lagoon, where infection takes place, but not in the turbidostat, or otherwise before infection takes place. In some embodiments, multiple genes required for the generation of infectious phage are removed from the selection phage genome, for example, gIII and gVI, and provided by the host cell, for example, in an accessory plasmid as described herein.

The vector system may further comprise a helper phage, wherein the selection phage does not comprise all genes required for the generation of phage particles, and wherein the helper phage complements the genome of the selection phage, so that the helper phage genome and the selection phage genome together comprise at least one functional copy of all genes required for the generation of phage particles, but are deficient in at least one gene required for the generation of infectious phage particles.

In some embodiments, the accessory plasmid of the vector system comprises an expression cassette comprising the gene required for the generation of infectious phage under the control of a conditional promoter. In some embodiments, the accessory plasmid of the vector system comprises a gene encoding pIII under the control of a conditional promoter the activity of which is dependent on a function of a product of the gene of interest.

In some embodiments, the vector system further comprises a mutagenesis plasmid, for example, an arabinose-inducible mutagenesis plasmid as described herein.

In some embodiments, the vector system further comprises a helper plasmid providing expression constructs of any phage gene not comprised in the phage genome of the selection phage or in the accessory plasmid.

Evolved Products

Some aspects of this invention provide evolved products of continuous evolution processes described herein. For example, some embodiments provide a modified T7 RNA polymerase (T7RNAP) having an altered substrate specificity and/or an increased transcriptional activity as compared to wild type T7RNAP. In some embodiments, a modified T7RNAP is provided that initiates transcription from a T3 promoter. In some embodiments, the modified T7RNAP exhibits an at least 2-fold, at least 5-fold, at least 10-fold, at least 20-fold, at least 30-fold, at least 40-fold, or at least 50-fold greater transcription rate from its native T7 promoter than the wild-type enzyme. In some embodiments, the modified T7RNAP exhibits an at least 2-fold, at least 5-fold, at least 10-fold, at least 20-fold, at least 30-fold, at least 40-fold, or at least 50-fold greater transcription rate from a non-native T7RNAP promoter than the wild-type enzyme. In some embodiments, the non-native T7RNAP promoter is a T3 promoter.

Host Cells

Some aspects of this invention relate to host cells for continuous evolution processes as described herein. In some embodiments, a host cell is provided that comprises at least one viral gene encoding a protein required for the generation of infectious viral particles under the control of a conditional promoter. For example, some embodiments provide host cells for phage-assisted continuous evolution processes, wherein the host cell comprises an accessory plasmid comprising a gene required for the generation of infectious phage particles, for example, M13 gIII, under the control of a conditional promoter, as described herein. In some embodiments, the host cells comprise the gene required for the generation of infectious viral particles under the control of a conditional promoter inserted into their genome, or as a cosmid, phagemid, or an artificial chromosome. In some embodiments, the host cell is a bacterial cell, for example, a bacterial cell amenable to M13 infection, such as certain E. coli cells. For M13 PACE, the host E. coli cells need to express the F-factor, for example, from an F' plasmid. Suitable F' E. coli cell lines and strains are known to those of skill in the art, and include, for example, the F'proA$^+$B$^+$ Δ(lacIZY) zzf::Tn10(TetR)/endA1 recA1 galE15 galK16 nupG rpsL ΔlacIZYA araD139 Δ(ara,leu)7697 mcrA Δ(mrr-hsdRMS-mcrBC) proBA::pir116λ$^-$ cells described herein.

In some embodiments, the host cell provided further comprises an expression construct comprising a gene encoding a mutagenesis-inducing protein, for example, a mutagenesis plasmid comprising a pBAD promoter, as described elsewhere herein.

Kits

Some aspects of this invention provide kits for continuous evolution as described herein. In some embodiments, a kit provided herein comprises a selection phage and a suitable accessory plasmid, as described in more detail elsewhere herein. In some embodiments, the kit may also comprise a helper phage or phagemid, a mutagenesis plasmid, a mutagen, an inducer, and/or a suitable host cell.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLE

General Methods

All equipment, reagents, suppliers, and relevant catalog numbers are detailed in Table 2. All PCR reactions were performed with HotStart Phusion II polymerase. Water was purified using a MilliQ water purification system (Millipore, Billerica Mass.).

DNA Cloning.

All vectors were constructed by isothermal assembly cloning. [44] 5× isothermal assembly buffer contained 3 mL 1 M Tris-HCl pH 7.5, 300 µL 1 M MgCl$_2$, 600 µL 10 mM dNTPs, 300 µL 1 M dithiothreitol, 1.5 g PEG-8000, 20 mg NAD, and H$_2$O to 6 mL. Individual 320 µL aliquots were frozen at −20° C. Isothermal assembly master mix was prepared by mixing 320 µL 5× buffer with 1 µL T5 Exonuclease, 20 µL Phusion polymerase, 160 µL Taq DNA ligase, and H$_2$O to 700 µL. Individual 15 µL aliquots in PCR tubes were frozen at −20° C. DNA fragments to be assembled were PCR-amplified using oligonucleotide primers designed to ensure between 30 and 40 base pairs of overlap homology with each adjacent fragment. DpnI was added directly to the PCR reactions to remove template DNA, followed by PCR cleanup with MinElute columns according to the manufacturer's protocol. Fragments were assembled by mixing equimolar amounts in a total 5 µL with 15 µL isothermal assembly master mix and incubating at 50° C. for 1 hr. Assembly mixtures were directly transformed into NEBTurbo competent cells by heat shock or purified by MinElute columns as described prior to electroporation.

Plasmids.

Figure 9:
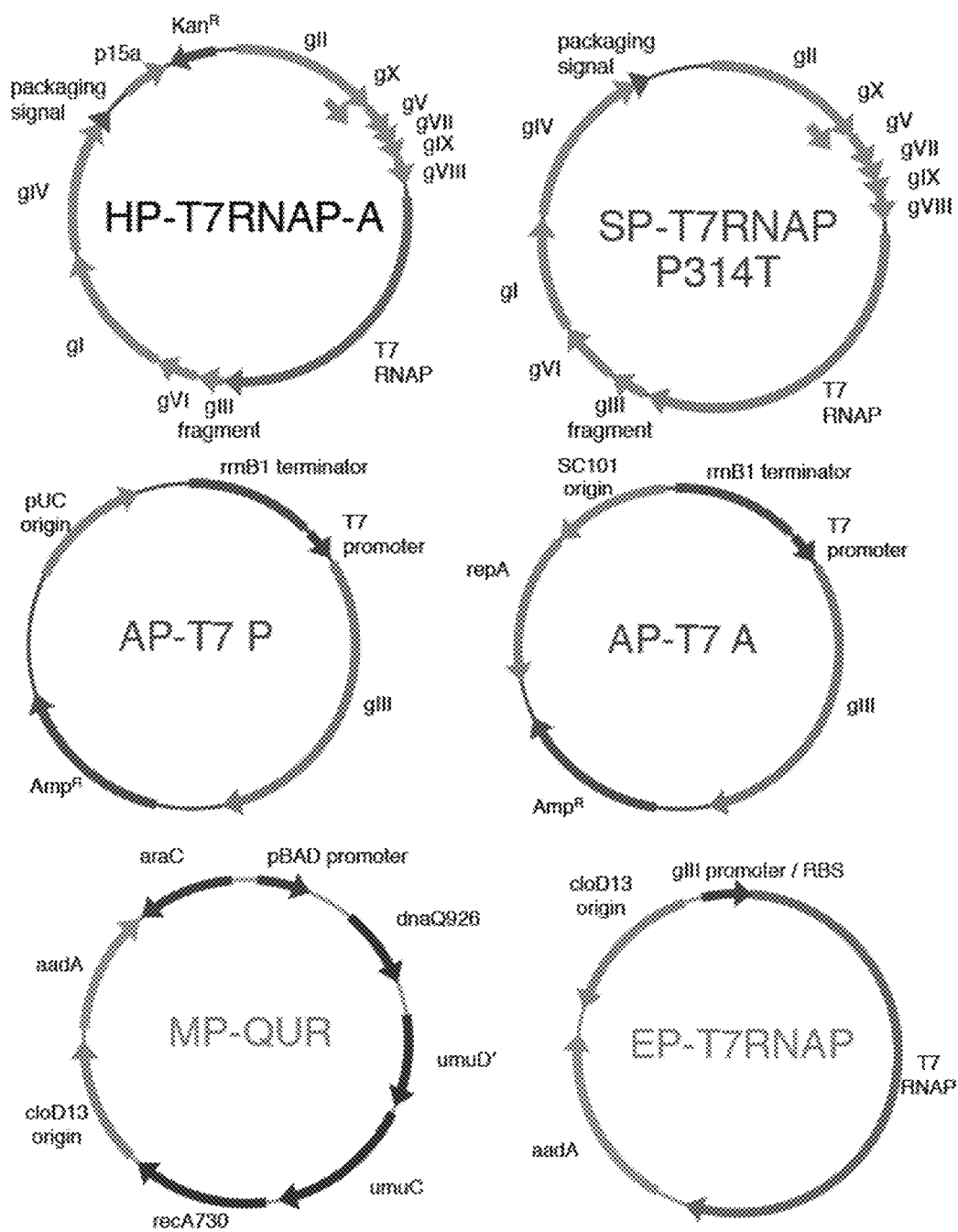
FIG. 9. Vector maps of plasmids used in PACE experiments. Helper phage HPT7RNAP was used for the discrete infection assays in FIGS. 3A-3B. Continuous propagation on host cells bearing accessory plasmid AP-T7 P for 48 hours yielded selection phage SP-T7RNAP P314T, the starting point for subsequent PACE experiments. Accessory plasmid AP-T7 A is the lower-copy version of AP-T7 P used to increase selection stringency. The arabinose-inducible mutagenesis plasmid MP-QUR was used for all mutagenesis and PACE experiments. Expression plasmid EP-T7RNAP was used to assay transcriptional activity in cells. See Table 1 for additional information.

T7 RNAP-dependent accessory plasmids (APs) contained, in order, a strong rrnB terminator, the promoter of interest, a desired ribosome binding site, gene III, the bla gene conferring carbenicillin resistance, and either the pUC or SC101 origin of replication. For selection stringency assays, RBS A=5'-AAGGAGGTAACTCATAGTG-3' (SEQ ID NO: 12), RBS B=5'-AAGGAAATAACTCATAGTG3' (SEQ ID NO: 13), and RBS C=5'-AAGAAAATAACTCATAGTG-3' (SEQ ID NO: 14), where underlined bases represent the start codon of gene III. Reporter plasmids were identical to SC101 accessory plasmids except for the replacement of gene III by full-length lacZ. T7 RNAP selection phage (SP) was constructed by replacing all but the last 180 bp of gene III with the gene encoding T7 RNAP in VCSM13 helper phage. The mutagenesis plasmid (MP) consisted of dnaQ926, umuD', umuC, and recA730 under control of the araC operon. Expression plasmids used for quantification assays consisted of the cloD13 origin of replication, aadA, and the wild-type gene III promoter and RBS driving expression of the evolved T7 RNAP variant. All plasmids used in this work are described in Table 1. Vector maps of representative plasmids are shown in FIG. 9.

TABLE 1

| | Class | Source | Notes |
|---|---|---|---|
| PACE plasmid | | | |
| HP-T7RNAP-A | Selection phage | This work | VCSM13-derived: T7RNAP replaces gIII |
| SP-T7RNAP P314T | Selection phage | This work | Evolved from HP-T7-A: no longer Kan$^R$ |
| AP-T7 P | Accessory | This work | High-copy T7RNAP accessory |
| AP-T7 A | Accessory | This work | Low-copy T7RNAP accessory |
| AP-T7T3 P | Accessory | This work | AP-T7 P: hybrid promoter |
| AP-T3 P | Accessory | This work | AP-T7 P: T3 promoter |
| AP-T3 A | Accessory | This work | AP-T7 A: T3 promoter |
| AP-T7-iN6 P | Accessory | This work | AP-T7 P: N6 transcript start |
| AP-T7-iC$_6$ P | Accessory | This work | AP-T7 P: C$_6$ transcript start |
| AP-T7-iC$_6$ A | Accessory | This work | AP-T7 A: C$_6$ transcript start |
| AP-T7-iA$_6$ P | Accessory | This work | AP-T7 P: A$_6$ transcript start |
| AP-T7-iA$_6$ A | Accessory | This work | AP-T7 A: A$_6$ transcript start |
| MP-QUR | Mutagenesis | This work | +ara -> dnaQ926, umuD'C |
| Other plasmids | | | |
| AP-T7 R | Accessory | This work | Weak RBS |
| AP-T7 S | Accessory | This work | Weaker RBS |
| EP-T7RNAP | Expression plasmid | This work | For in-cell activity quantification |
| HPdOd3 | Helper | This work | For phagemid infection assays |
| AP-RNAP α-LGF2 | Accessory | This work | 2-hybrid accessory |
| SP- Gal11p-ZF | Selection phagemid | This work | 2-hybrid phagemid |
| AP-RZH3 | Accessory | This work | Recombinase accessory |
| SP-HinHZ | Selection phagemid | This work | Recombinase phagemid |
| SP-Cre | Selection phagemid | This work | Control phagemid |
| VCSM13-lacI | Assay phage | This work | For loss-of-function mutagenesis assay |
| pJC137 | Assay plasmid | This work | Selects for loss of lacI repressor function |
| pT7-911Q | Expression plasmid | V. D'Souza | T7 RNAP expression/purification |

Bacterial Strains.

All DNA cloning was performed with Mach1 cells or NEB Turbo cells. Early discrete infection assays and PACE experiments were performed with PirPlus DH10βF'DOT cells.

Plaque assays and PACE experiments with T7 RNAP were performed using E. coli S109 cells derived from DH10B by replacement of the proBA locus with the pir116 allele, as previously described. [45] To our knowledge, this modification was not required for PACE experiments with T7 RNAP. Similarly, the lad cassette was deleted from the F plasmid and from the chromosome to enable mutagenesis assays. S109 cells were rendered F$^+$ by conjugation with ER2738. The complete genotype of the resulting strain is F'proA$^+$B$^+$ Δ(lacIZY) zzf::Tn10(TetR)/endA1 recA1 galE15 galK16 nupG rpsL ΔlacIZYA araD139 Δ(ara,leu)7697 mcrA Δ(mrr-hsdRMS-mcrBC) proBA::pir116λ$^-$.

Discrete Infection Assays.

Discrete (non-continuous) infectivity assays were performed by cotransforming phage bearing antibiotic resistance genes with the appropriate accessory plasmid into competent cells to generate phage donors. For two-hybrid and recombinase experiments, phage producing cells contained gIII-deleted helper phage, accessory plasmid, and selection phagemid.

Colonies were picked and grown overnight in 2×YT media with both antibiotics. 2 μL donor cells were mixed with 198 μL F$^+$ recipient cells in mid-exponential phase containing an antibiotic resistance gene not found in the donor. Mixtures were incubated at 37° C. for 1.5 hours and 20 μL was spread on plates containing the donor and the recipient antibiotics. Infection was quantified by the number of resulting colonies after incubation at 37° C. overnight. For plaque assays, phage DNA was transformed into electrocompetent cells containing the appropriate accessory plasmid and recovered for 1 hr at 37° C. Serial dilutions were mixed with 300 μL F+ recipient cells grown to exponential phase in 14 mL Falcon culture tubes and incubated at 37° C. for 15 minutes. 3 mL top agar (7 g/L from LB broth base) at 50° C. was added to each tube, briefly vortexed, and poured onto minimal agar plates incubated at 37° C. for 8 hours or overnight to generate plaques.

Turbidostat Assembly.

Figure 2A:
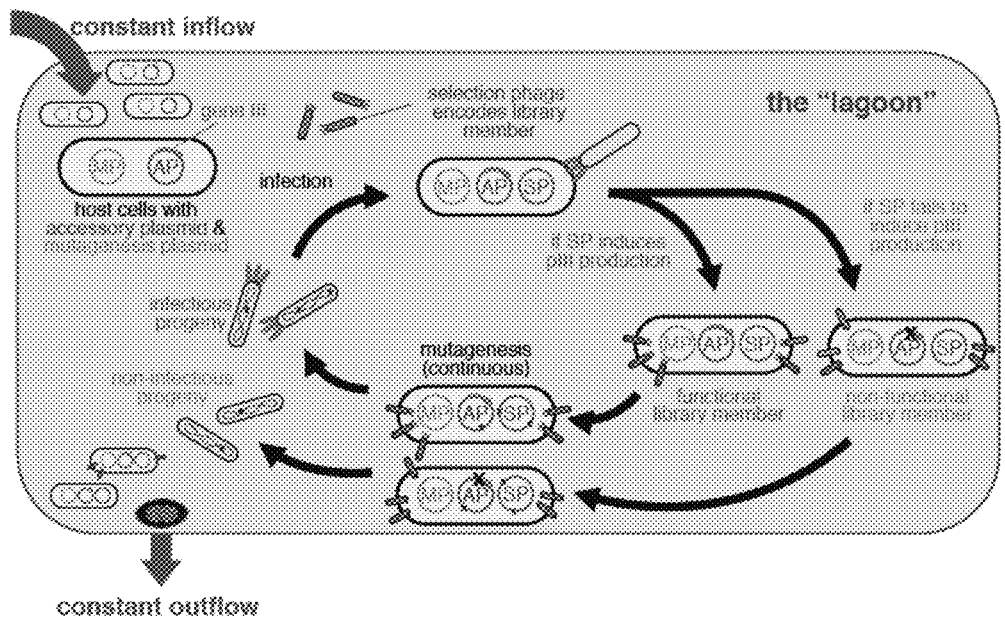
FIGS. 2A and 2B. Overview of the PACE system.
Figure 2B:
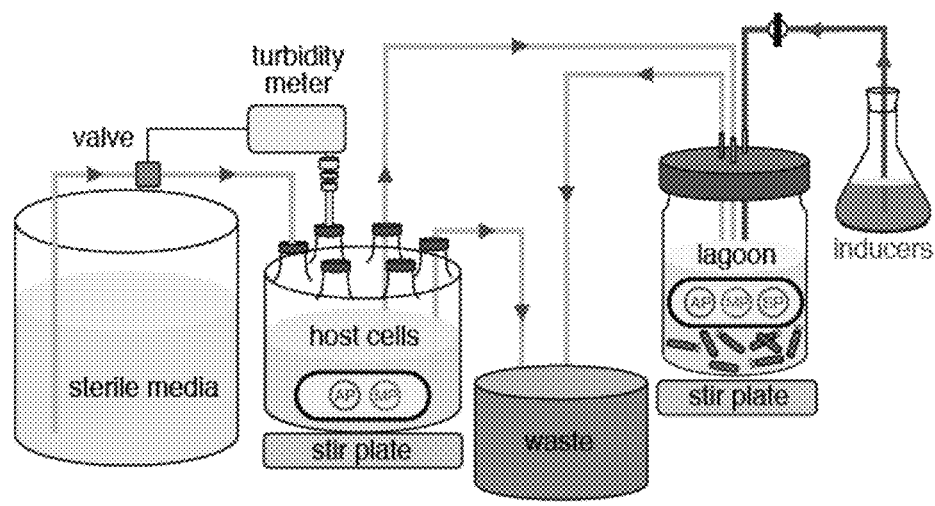

Assembly followed the schematic in FIG. 2B. Turbidostats were constructed from BioProbe flasks on magnetic stir plates. Each flask was equipped with a TruCell2 cell density meter held in a GL32 probe holder with compression fitting. GL45 and GL32 septa pierced with needles transferred media to and from the turbidostat via an 8-channel peristaltic pump with Tygon tubing. A needle set at the desired turbidostat volume level pumped excess cells to the waste container.

Figure 15:
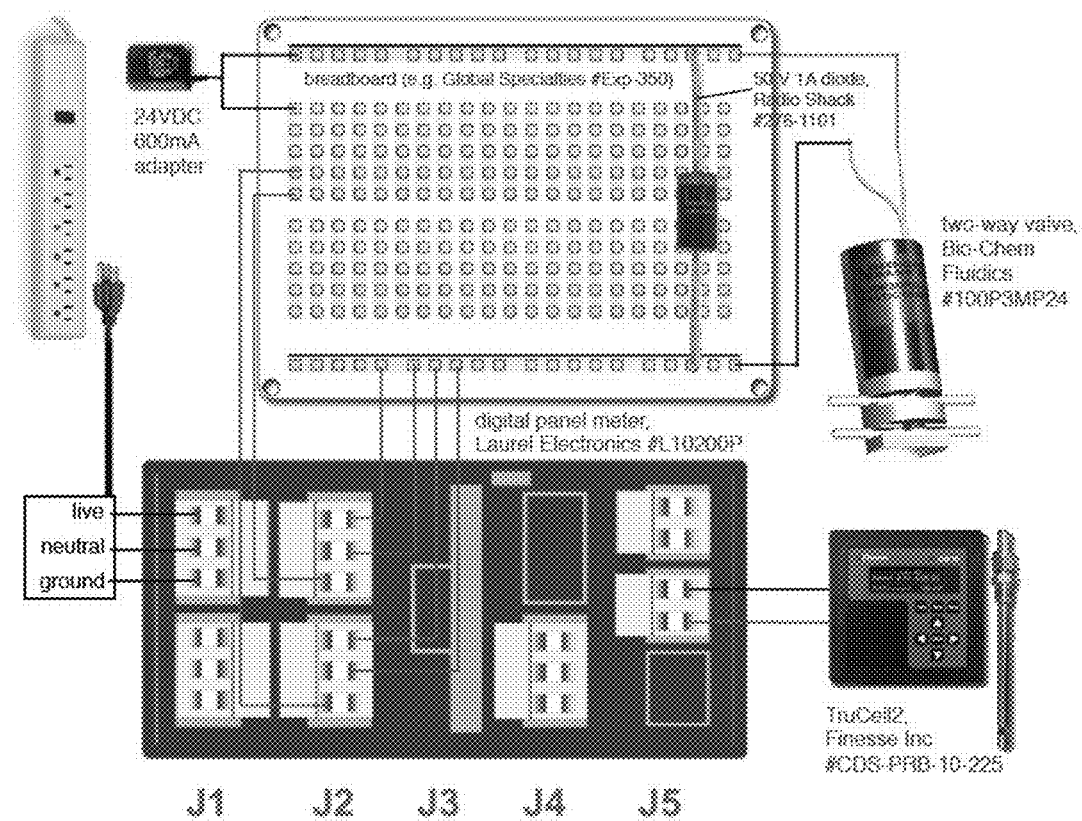
FIG. 15. As schematic illustrating the electrical system controlling the flow of fresh media in response to the cell density. The valve controlling turbidostat media inflow is opened and closed by a programmable digital panel meter processing cell density information from the TruCell2 probe.

A 0.2 μm filter attached to a 14-gauge needle piercing the septum vented the turbidostat vessel. A two-way valve controlled media flow to the turbidostat, connected such that a closed valve state returned the media to source. The valve opened and closed in response to TruCell2 4-20 mA output processed by a digital panel meter programmed with the desired set point. Panel meters were unlocked according to the instruction manual and programmed to the following settings: Input dc_A, Setup 30_ 10, Config 00000, Filtr 11009, dec.pt ddd.dd, lo in 00.400, lo rd 004.00, hi in 02.000, hi rd 020.00, Alset 00036, deu1h 000.01, deu2h 000.01. The digital panel meter, adapter, and valve were connected with a solderless breadboard according to the diagram shown in FIG. 15. Lagoons consisted of 100 mL Pyrex bottles with GL45 septa pierced with needles for fluid delivery, a 0.2 μm filter terminated vent line, and a magnetic stir bar. Excess lagoon volume was continually pumped to waste via a waste needle set at the desired lagoon volume.

Media Preparation.

Each 20 L media carboy received 140 g anhydrous potassium phosphate dibasic, 40 g potassium phosphate monobasic, 20 g ammonium sulfate, and 20 mL Tween 80 in 20 L H$_2$O.

Carboys were loosely capped with Polyvent filling/venting closures with an autoclavable 0.2 µm filter fastened to the venting port. Media was autoclaved until visibly boiling (typically 120 min at 30 psi, 121° C.) and allowed to cool overnight. Media supplement was prepared from 90 g glucose, 10 g sodium citrate, 0.25 g anhydrous magnesium sulfate, 10 g casamino acids, 0.15 g tetracycline-HCl, 0.6 g carbenicillin, 0.6 g spectinomycin, and 0.5 g (L)-leucine, dissolved in 500 mL $H_2O$, and filtered with a Nalgene 500 mL filtration unit. 500 mL media supplement was added to each carboy under conditions that minimize the risk of media contamination (in the case of the reported experiments, immediately following 1 hour of germicidal UV irradiation).

Sterilization and Cell Culture.

The autoclavable components of a turbidostat apparatus include the BioProbe flask, TruCell2 probe, needles, vent filter, and tubing. All such components were autoclaved fully assembled except for tubing, which was connected while hot. Upon equilibrating to ambient temperature, the peristaltic pump responsible for media addition and waste removal was started with the valve opened until the desired volume was reached. The TruCell2 probe was connected to its transmitter and zeroed. Turbidostats were seeded with 100 µL of an overnight culture of host cells. Turbidostats and lagoon cultures were grown at 37° C.

Cell Density Calibration.

Serial dilution plating was used to generate a calibration curve to determine TruCell2 output and panel meter setting corresponding to the desired cell density. For these experiments, both panel meter alarms were programmed to open the valve at 6.80 mA. Cells were pumped from the turbidostat to the lagoons via peristaltic pumps with silicone (platinum) two-stop tubing. Calibration curves relating pump speed in rpm to volumetric flow rate were determined experimentally with a timer and graduated cylinder for each tubing size.

PACE Experiments.

Turbidostats and lagoons were assembled as described above. Upon the turbidostat reaching the desired set point of 6.80 mA corresponding to $5 \times 10^8$ cells/mL, lagoons were connected to turbidostats, waste needles were set at the desired volume, and lagoon pumps were set to a flow rate corresponding to the desired dilution rate. Each lagoon was seeded with 100 µL of an overnight culture producing selection phage. To induced elevated mutagenesis, 10% filter-sterilized (L)-arabinose was delivered by a separate peristaltic pump to each lagoon requiring enhanced mutagenesis to a final concentration of 1%. Lagoon aliquots were taken by sampling lagoon waste lines at the luer lock just after the peristaltic pump. Individual clones were isolated by plaque assay or amplified by PCR, assembled into a T7 RNAP activity assay plasmid, and transformed into cells containing a lacZ reporter plasmid. Active clones were picked by blue/white screening.

Selection Phage Optimization.

Figure 3A:
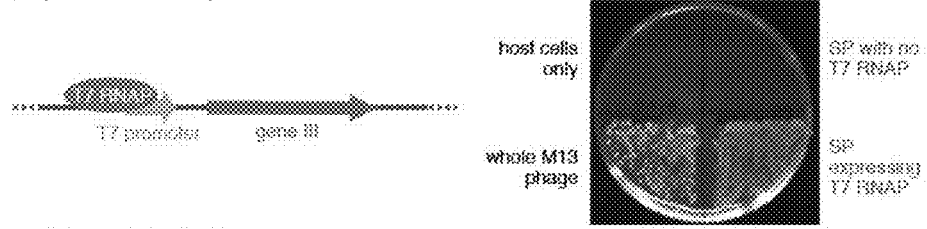
FIGS. 3A and 3B.
Figure 3A:
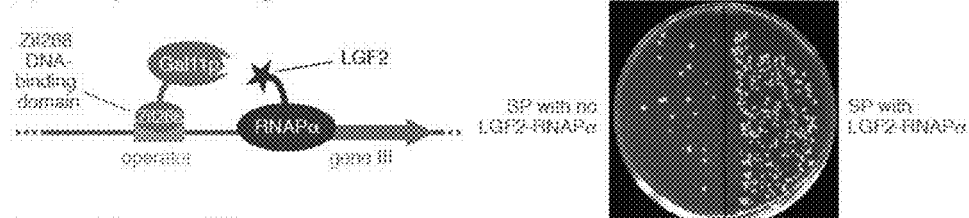
Figure 3A:
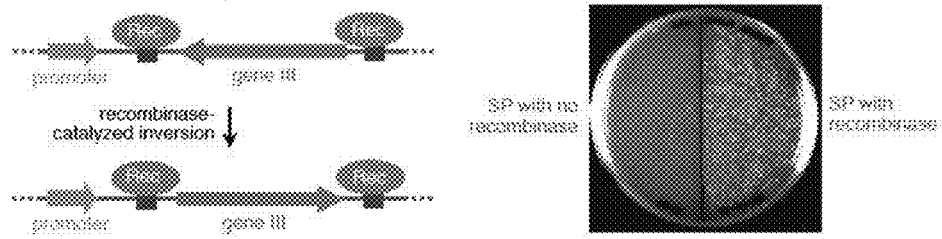

T7 RNAP was subcloned into VCSM13 helper phage encoding kanamycin resistance, generating HP-T7RNAP A, used in the discrete infection assay shown in FIG. 3A.

To ensure that improvements to the phage genome did not interfere with the evolution of T7 RNAP, HP-T7RNAP A was propagated in a lagoon fed by S109 host cells containing AP-T7 A and DP-QUR and supplemented with arabinose for 48 hours at 2.0 volumes/hour. Individual plaques were isolated and their T7 RNAP genes sequenced. One plaque contained only a single point mutation in T7 RNAP, P314T, and was chosen as the preoptimized selection phage for T7 RNAP evolution. Sequencing of the rest of the selection phage revealed numerous changes relative to the parental VCSM13. Notably, the entire p15a-$Kan^R$ cassette inserted into the intergenic (IG) region to create VCSM13 was perfectly deleted to reconstitute the wild-type M13 IG region. Other changes included N79S, F286S, and I360T mutations in gIV, a K249R mutation in gII, three silent mutations back to the corresponding M13 base, two other silent mutations, and the deletion of one thymine residue in the terminator before gIII, possibly increasing the expression of T7 RNAP. These regional patterns of variation parallel those observed by Husimi in more extensive filamentous phage evolution experiments. [46] This evolved phage, designated SP-T7RNAP P314T, was used as the starting selection phage for all subsequent PACE experiments.

Mutagenesis Assays.

The lacI gene was cloned into VCSM13 between the p15a origin and $kan^r$ to generate VCSM13-lacI. A turbidostat was grown to a set point equivalent to $5 \times 10^8$ cells/mL with S109 cells containing the mutagenesis plasmid (MP). Lagoons were seeded with 10 µL VCSM13-lacI and run at 2.5 volumes/hour for 3 hours. One lagoon was supplemented with 10% arabinose to a final concentration of 1%, while the other was not. Aliquots were removed after 3 hours and each was used to infect a 100-fold greater volume of recipient cell culture of S109 cells containing a reporter plasmid conferring carbenicillin and spectinomycin resistance with a lacI binding site (lacO) capable of repressing spectinomycin resistance. Mixtures were incubated for 1.5 hr at 37° C., spread on 2×YT plates containing spectinomycin, kanamycin, and carbenicillin, and incubated at 37° C. overnight.

Colonies were counted for induced and uninduced lagoons to estimate the fold increase in mutagenesis.

Figure 11:
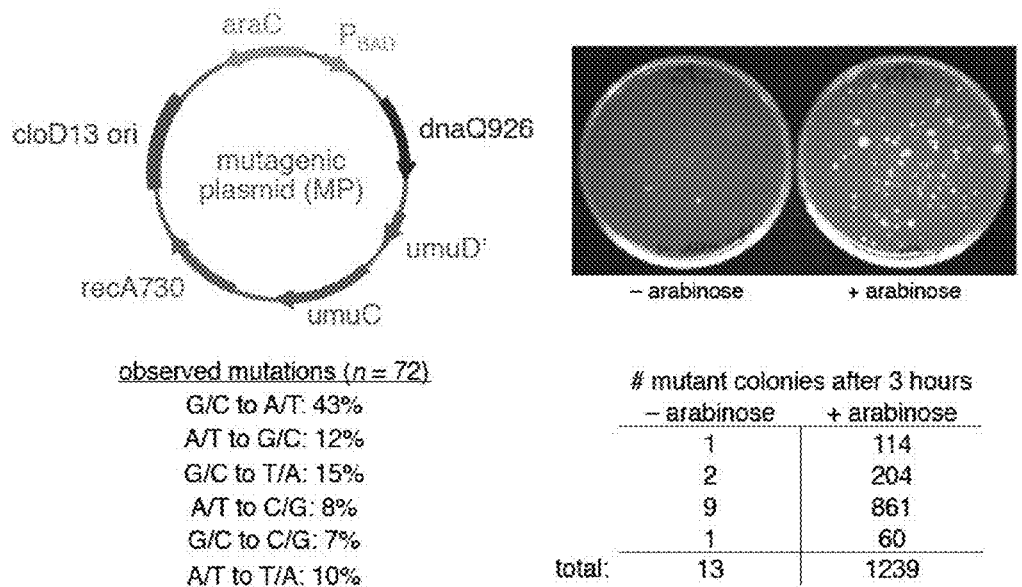
FIG. 11. Structure and function of the mutagenesis plasmid (MP). Induction with arabinose increases the frequency of inactivating mutations in a phage-encoded lacI gene by ~100-fold over four independent experiments. All types of transitions and transversions were observed with a bias towards G/C to A/T transitions.

Seventy-two (72) colonies were sequenced to determine the frequencies of all transitions and transversions within mutated lacI genes. The results are shown in FIG. 11. All sequenced colonies contained at least one mutation capable of inactivating repressor function.

In vivo T7 RNAP Activity Assays.

Overnight cultures of S109 cells grown in 2×YT containing reporter plasmid and expression vector were diluted 4-fold in fresh 2×YT media. 20 µL of the diluted culture was mixed with 80 µL Z buffer (60 mM $Na_2HPO_4$, 40 mM $NaH_2PO_4$, 10 mM KCl, 1 mM $MgSO_4$, 50 M BME, pH 7.0) in Falcon Microtest 96-well OptiLux assay plates and the absorbance at 595 nm was measured using a Spectra M5 plate reader. 25 µL of 1 mg/mL methylumbelliferyl-beta-(D)-galactopyranoside was added to each well and the time recorded. Plates were incubated at 30° C. and fluorescence was measured at 360/460 nm on a Spectra M5 plate reader. Plates were measured at multiple time points to avoid saturation of the spectrophotometer or consumption of the substrate, depending on the activity level of the T7 RNAP enzyme being assayed. MUG fluorescence units were calculated as previously described. [47]

T7 RNAP Protein Purification.

T7 RNAP variants were cloned into pT7-911Q, a His-tagged T7 RNAP expression vector. [48] Overnight cultures grown at 30° C. were diluted 1:500 in LB broth containing 50 µg/mL carbenicillin and 2% glucose. Upon reaching $OD_{600}$=~0.5, cultures were centrifuged at 4000 g for 5 minutes and resuspended in LB broth with 0.4 mM IPTG and 50 µg/mL carbenicillin. Cultures were grown for 4 hours at 30° C., spun at 8000 g for 6 minutes, and the pellet was frozen overnight. Binding buffer consisted of 50 mM Tris, 300 mM NaCl, 5% glycerol, 5 mM beta-mercaptoethanol, and 10 mM imidazole at pH 8.0. Wash buffer was composed of 50 mM Tris, 800 mM NaCl, 5% glycerol, 5 mM beta-mercaptoethanol, and 20 mM imidazole at pH 8.0. Elution buffer was equivalent to wash buffer with 500 mM imidazole. Pellets from 25 mL culture were resuspended in 1 mL wash buffer and cells were lysed by sonication while kept on ice using a Misonix CL4 sonicator at maximal microtip power for 45 seconds in 1-second bursts. Cell debris was spun down at 20,000 g for 15 minutes at 4° C. Ni-NTA spin columns were equilibrated with 500 µL binding buffer and spun at 800 g for 2 minutes. Lysate supernatant was loaded onto each column and spun at 300 g for 5 minutes. Columns were washed twice with 500 µL wash buffer, spinning at 800 g for each, then eluted twice with 250 µL elution buffer. Proteins were dialyzed into 20 mM Tris, 100 mM NaCl, 5% glycerol, 1 mM EDTA, 1 mM DTT, pH 8.0, and concentrated using Amicon Ultra-0.5 30K concentration columns.

In vitro T7 RNAP Activity Assays.

Purified T7 RNAP variant concentrations were determined by Bradford assay and then by Coomassie stain on a 4-12% NuPage gel. Templates were prepared by PCR amplification of 150 bp fragments of the reporter plasmids used for in vivo assays including the promoter and the start of the lacZ gene. Templates were purified by MinElute spin column.

Transcription reactions were performed in 1×RNA polymerase buffer consisting of 40 mM Tris-HCl, 6 mM $MgCl_2$, 10 mM dithiothreitol, 2 mM spermidine pH 7.9 with 1 mM rNTPs, 1 ng template DNA, purified polymerase variant, and 2 mCi [$\alpha$-$^{32}$P]ATP. Reactions were incubated at 37° C. for 20 minutes, mixed with an equivalent volume of loading dye consisting of 7 M urea, 178 mM Tris-Cl, 178 mM $H_3BO_3$, 4 mM EDTA and 0.002% bromophenol blue, then electrophoresed on Criterion 5% or 10% TBE-urea denaturing gels. To control for increased signal from [$\alpha$-$^{32}$P]ATP in the $iA_6$ promoter and ensure transcripts fully entered the gel, $iA_6$ and wt T7 RNAs were transcribed from double-stranded templates of sequence 5'-TAATACGACTCAC-TATAGGGAGAGCCACCACCACCACCACCACCA-3' (SEQ ID NO: 15) and 5'-TAATACGACTCAC-TATAAAAAAAGCCACCACCACCACCACCACCA-3' (SEQ ID NO: 16), digested with T1 ribonuclease to remove the first seven bases, and electrophoresed on Criterion 15% TBE-urea gels. Phosphor screens were exposed and imaged on a Typhoon Trio phosphorimager. Bands corresponding to transcription products were quantified with ImageJ software.

RACE Analysis.

In vitro transcription reactions with purified T7 RNAP variants were performed as described above but without the addition of any radioactive nucleotide using polymerase variant C6-80.9. DNA oligonucleotides of sequence 5'-TAATACGACTCACTATACCC-3 (SEQ ID NO: 17)' and 5'-CCCACCCAAAAAAAAAAAAAAAAGGGGGG-TATAGTGAGTCGTATTA-3' (SEQ ID NO: 18) formed the $iC_6$ template, and 5'-TAATACGACTCACTATAGGG-3' (SEQ ID NO: 19) and 5'-CCCAC-CCAAAAAAAAAAAAAAAATCTCCCTATAGT-GAGTCGTATTA-3' (SEQ ID NO: 20) formed the wild-type template. Each 200 µL transcription reaction was treated with 2 µL calf intestinal phosphatase (CIP) for 1 hour at 37° C., extracted with phenol-chloroform twice to remove enzymes, and precipitated with ethanol. Pellets were resuspended in 1×DNase Turbo buffer with 5 µL DNase in a total volume of 100 µL, incubated for 2 hours at 37° C., extracted with phenol-chloroform twice, and precipitated with ethanol. 5 µL of purified transcript was mixed with 1 µL T4 polynucleotide kinase (PNK) in 1×PNK buffer and incubated at 37° C. for 1 hour. 1 µL of treated RNA was ligated to 30 ng RNA adapter of sequence 5'-GCUGAUGGC-GAUGAAUGAACACUGCGUUUGCUGGC-UUUGAUGAAA-3' (SEQ ID NO: 21) with T4 RNA Ligase in 1×RNA Ligase Buffer at 37° C. for 1 hour. 1 µL of ligated RNA was reverse transcribed by mixing with 1 mM dNTPs and a complementary DNA primer of sequence 5'-CCCCCAAACCCCCAAAAAAAAAACCCAC-CCAAAAAAAAAAAAA-3' (SEQ ID NO: 22) at a final concentration of 5 µM at 65° C. for 15 minutes followed by 10 U/µL SuperScript III reverse transcriptase in 1×RT buffer, 5 mM $MgCl_2$, and 10 mM dithiothreitol at 50° C. for 1 hour. Enzymes were denatured at 85° C. for 5 minutes followed by amplification with nested PCR reactions using primers 5'-CGATCCGAACGCAGCATTTACGCTGATGGCGAT-GAATGAACACTG-3' (SEQ ID NO: 23) and 5'-CCCCCAAACCCCCAAAAAAAAAACCCAC-CCAAAAAAAAAAAAA-3' (SEQ ID NO: 24) followed by 5'-AACGCCAGCAACGCGAATAAGAGAATACATC-GATCCGAACGCAGC-3' (SEQ ID NO: 25) and 5'-GCTAGTTATTGCTCAGCGGAAAAAAAAAAAAAC-CCCCAAACCCCC-3' (SEQ ID NO: 26). PCR products were subcloned with TOPO TA kits. Individual colonies were picked and sequenced using the M13 reverse primer.

Calculation of Phage Generation Time During PACE.

The phage generation time was estimated using a steady-state replication model in which phage fitness is constant. One phage generation encompasses an infected cell exiting the lagoon, one of its progeny phage infecting an incoming cell, and that infected cell exiting the lagoon. To determine the average time required for one of the progeny phage to infect an incoming cell, it was assumed that no progeny phage have yet infected an incoming cell and that cells entering the lagoon are instantaneously infected due to the high phage ($5 \times 10^{10}$ $mL^{-1}$) and cell ($5 \times 10^8$ $mL^{-1}$) concentrations relative to the adsorption coefficient of filamentous phage ($3 \times 10^{-11}$ $mL^{-1}$ $min^{-1}$ $phage^{-1}$ $cell^{-1}$). [49] Because lagoons operate in a steady state during most of a PACE experiment, the total phage and cell concentration does not change over time. Therefore, the progeny of a single cell exiting the lagoon infects exactly one cell entering the lagoon, on average, to achieve population replacement. A number of incoming cells equal to the total cell population will enter before one of the progeny phage achieves infection. Consequently, the average time from instantaneous cell exit to infection of a new cell by a progeny phage is 1/(dilution rate).

According to the dilution equation, solutes wash out at a rate of dC/dt=−(dilution rate)*(concentration). This gives a washout equation of C(t)=c1*exp[−(dilution rate)*time]. This washout equation may be used as the probability density function prob [time] for the probability of a given cell washing out at a specific time after it enters the lagoon. To ensure that the probability of all currently resident cells washing out given infinite time is 1, the dilution rate was set to c1=1/(dilution rate). To calculate the probability <t> for a single cell, the integral [t*prob[t], {t,0,infinity}] was calculated. The integral of [time*(dilution rate)*exp[−(dilution rate)*time], {t, 0, infinity}]=1/(dilution rate). Therefore, the average time from infection to washout is also equal to 1/(dilution rate).

Summing the two halves of the phage replicative cycle, the average phage generation time in our model is equal to 2/(dilution rate). At a dilution rate of 2.0 volumes/hour, as in the evolution towards T3 promoter recognition, the average phage undergoes 24 generations per 24 hours. At 2.5 volumes/hour, as in the initiation site evolution experiments, the average phage undergoes 30 generations per 24 hours. For the maximum observed dilution rate of 3.2 volumes/hour, the average phage undergoes just over 38 generations per 24 hours. In all cases the fastest replicating 1% of phage have undergone a significantly greater number of generations per 24 hours.

Phage-Assisted Continuous Evolution (PACE)

Figure 1B:
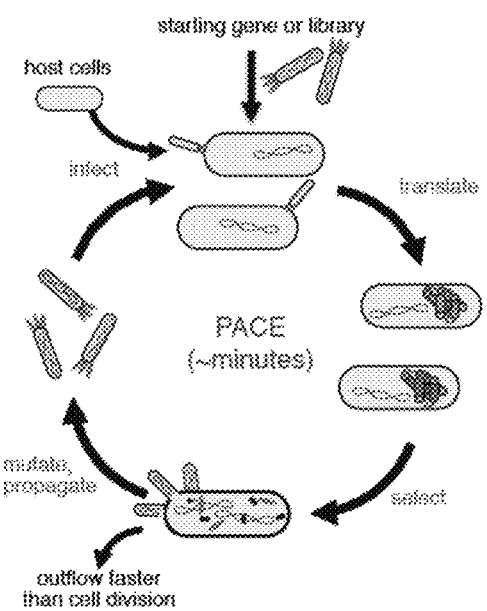

A scheme was devised that exploits the continuous culture and selection of the M13 filamentous bacteriophage [15,16] (commonly used in phage display [17]) to enable the continuous directed evolution of proteins or nucleic acids. In phage-assisted continuous evolution (PACE), E. coli host cells continuously flow through a fixed-volume "lagoon" containing an actively replicating population of phage DNA vectors encoding the gene(s) of interest (FIGS. 1A and 1B).

The average residence time of host cells in the lagoon is less than the time required for E. coli replication. As a result, mutations accumulate only in the evolving population of phage vectors since they are the only replicating DNA in the lagoon. The mutation of host cells in the lagoon should therefore have minimal impact on the outcome of the selection over many rounds of phage replication, and mutagenesis conditions are not limited to those that preserve E. coli viability.

PACE achieves continuous selection by linking the desired activity to the production of infectious progeny phage containing the evolving gene(s). Phage infection requires protein III (pIII; encoded by gene III), which mediates F pilus binding and TolA-dependent host cell entry. [18,19] Phage lacking pIII are ~$10^8$-fold less infectious than wild-type phage.[20] Crucially, the production of infectious phage scales with increasing levels of pIII over concentrations spanning two orders of magnitude. [21] To couple pIII production and thus phage infectivity to the activity of interest, gene III was deleted from the phage vector and inserted it into an "accessory plasmid" (AP) present in the E. coli host cells (see FIG. 9 for plasmid maps). The production of pIII from the AP is dependent upon the activity of the evolving gene(s) on the phage vector and in the absence of this activity is insufficient to support the production of infectious phage. Phage vectors able to induce sufficient production of pIII from the AP will therefore propagate and persist in the continuously diluted lagoon, while phage vectors unable to induce pIII will be washed out over time (FIGS. 2A and 2B). Because pIII expression level determines the rate of infectious phage production,[21] the progeny of a phage encoding a mutant gene that results in a higher level of pIII production will infect a larger share of host cells relative to the progeny of a phage encoding a less active gene. Mutants with higher activity will therefore experience a selective advantage until pIII levels are sufficient for maximal infectious phage release.

Figure 10:
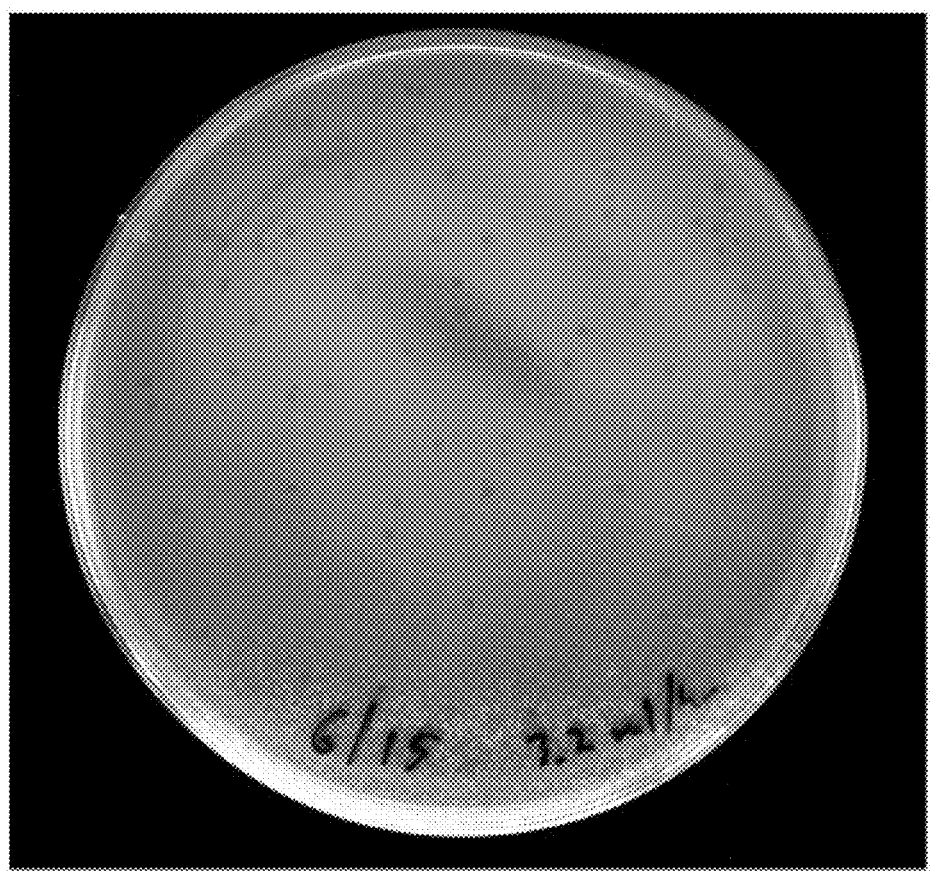
FIG. 10. Continuous phage propagation persists at a lagoon flow rate of 3.2 volumes per hour. A plaque assay was performed after continuous overnight dilution of SP encoding wild-type T7 RNA polymerase propagating on host cells containing an AP with a high-copy wild-type T7 promoter at a flow rate of 3.2 lagoon volumes per hour. The presence of plaques containing T7 phage indicates that the phage replication rate is sufficient to withstand this dilution rate.

Due to the brevity of the phage life cycle (phage production begins ~10 minutes postinfection), [22] PACE can mediate many generations of phage replication under selective conditions in a single day. Activity-dependent phage vectors were observed that tolerate lagoon flow rates up to 3.2 volumes per hour (FIG. 10), corresponding to ~115 population doublings and an average of ~38 phage generations per 24 hours. Because each lagoon is simply a vessel maintained at constant volume, multiple lagoons can evolve genes in parallel, with each 100 mL lagoon containing ~$5 \times 10^{10}$ host cells selectively replicating active phage variants.

Importantly, PACE requires little or no intervention during evolution and obviates the need to create DNA libraries, transform cells, extract genes, or perform DNA cloning steps during each round.

Linkage of Functions to pIII Production

Figure 3B:
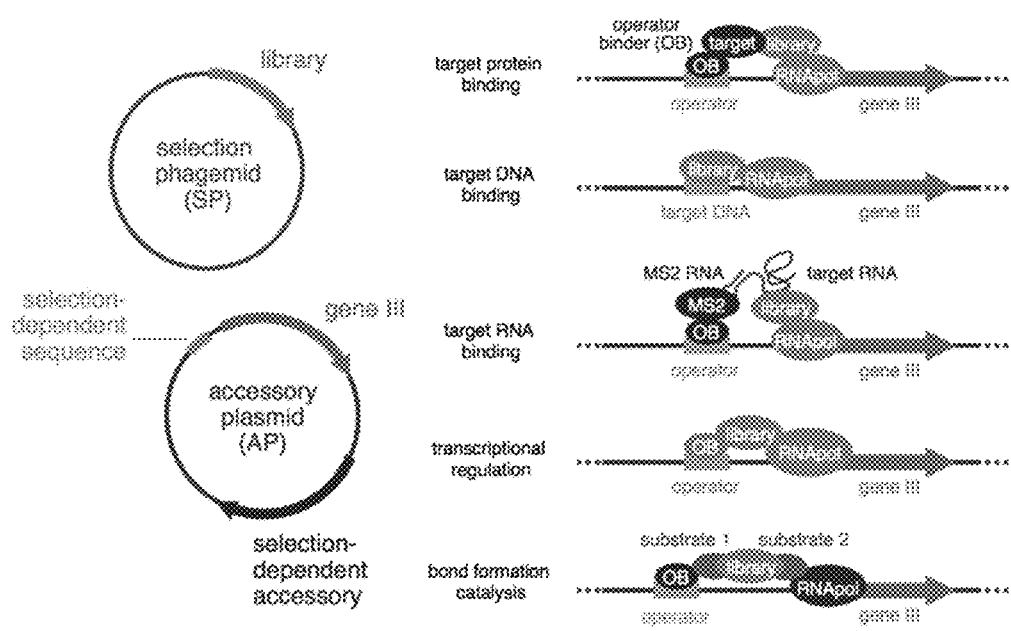
Figure 4:
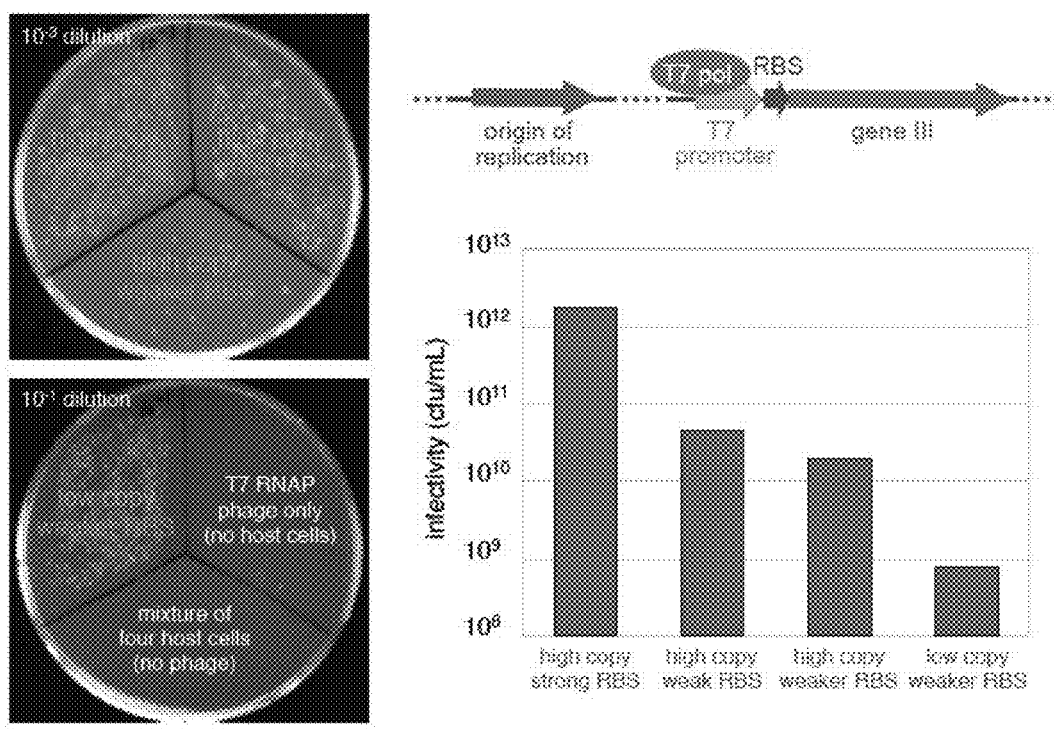
FIG. 4. Selection stringency can be controlled by varying the gene III ribosome binding site (RBS) and the accessory plasmid copy number. Selection phage encoding T7 RNAP were paired with accessory plasmids containing a strong, weak, or weaker ribosome binding site [26] with a high copy colE1 or a low-copy SC101 origin. Phage infectivity diminished with decreasing RBS strength and with decreasing copy number, reflected in lower phage titers.

In principle, PACE is capable of evolving any gene that can be linked to pIII production in E. coli, including activities that influence pIII function at the transcriptional, translational, or post-translational levels. Because a wide variety of functions including DNA binding, RNA binding, protein binding, bond-forming catalysis, and a variety of enzyme activities have been linked to the expression of a reporter protein through n-hybrid [23-25] and other conditional transcription strategies, PACE can be applied to the evolution of many different activities of interest. As examples, protein-protein binding, recombinase activity, and RNA polymerase activity were successfully linked to phage infectivity in discrete infection assays by creating variants of the AP that associate each of these activities with pIII production (FIGS. 3A and 3B). PACE applies optimal evolutionary pressure when pIII levels are above the minimal threshold required to prevent total phage loss, but below the amount needed to produce maximally infectious phage. This window can be shifted in at least two ways to accommodate the current activity level of the encoded genes. It was observed that selection stringency can be tuned by varying the copy number of the AP or by altering the ribosome binding site (RBS) [26] of gene III to modulate the efficiency with which gene III is transcribed or translated (FIG. 4).

Inducible Enhanced Mutagenesis

Although the basal mutation rate of replicating filamentous phage is only $5.3 \times 10^{-7}$ substitutions/bp, [27] the large number of phage vectors infecting cells in a 100 mL lagoon (~$5 \times 10^{10}$) ensures the presence of all possible single point mutants in any phage vector of viable size at any instance. To enhance the rate of gene diversification in PACE in a controllable manner, an inducible mutagenesis plasmid (MP) was constructed that elevates the error rate during DNA replication and facilitates the use of chemical mutagens. The addition of arabinose to the lagoon induces expression of the DNA polymerase dominant negative proofreading subunit dnaQ926 [28] and the production of the specialized repair DNA polymerase pol V. [29] The increase in mutagenesis was measured by continuously propagating phage encoding the lac repressor (lacI) in lagoons with or without arabinose and selecting for loss-of-function mutants after three hours of continuous propagation.

Full induction with 0.8% arabinose increased the apparent mutagenesis rate of the lacI gene by ~100-fold, inducing all possible transitions and transversions (FIG. 11).

This increase in mutagenesis rate has a significant impact on the nature of PACE gene libraries. For a 1 kb target gene, an enhanced mutation rate of ~$5 \times 10^{-5}$ substitutions/bp yields $2.5 \times 10^9$ mutations in $5 \times 10^{10}$ phage after one generation, sufficient to generate all possible single and double mutants and a significant number of triple mutants. Because the arabinose-induced mutagenesis rate enables a 100 mL lagoon to exhaustively sample all possible double mutants of any starting phage vector, single-mutation fitness valleys can be traversed during PACE.

Continuous Evolution of T7 RNA Polymerase: Promoter Recognition

The DNA-dependent RNA polymerase of bacteriophage T7 (T7 RNAP) is widely used to transcribe RNA in vitro and to drive protein expression in cells. T7 RNAP is highly specific for its promoter sequence (TAATACGACTCAC-TATA, SEQ ID NO: 27), and exhibits virtually no detectable activity on the consensus promoter of the related bacteriophage T3 (AATTAACCCTCACTAAA, SEQ ID NO: 28). The nucleotide at position −11 (G in the T7 promoter; C in the T3 promoter) is known to play an especially important role in T7 RNAP promoter recognition, but the known N748D mutation in T7 RNAP that confers recognition of a C base at position −11 still exhibits <5% activity on the T3 promoter.[30] Despite decades of study and several attempts to engineer the specificity of T7 RNAP towards other promoters including that of T3, a mutant T7 RNAP capable of recognizing the T3 promoter has not been previously reported. [31-34] PACE was challenged to evolve T7 RNAP recognition of the complete T3 promoter.

Figure 12:
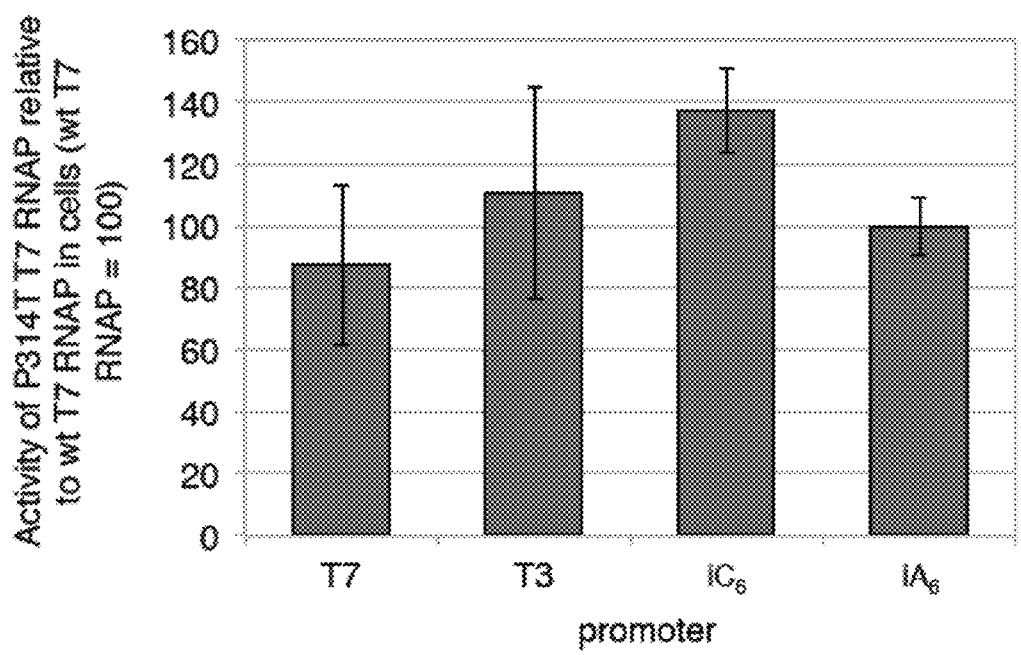
FIG. 12. Transcriptional activity of the starting T7 RNAP harboring a P314T mutation is similar to that of wild-type polymerase when assayed on T7, T3, $iC_6$, and $iA_6$ promoters in cells. Each bar shows the activity of the P314T mutant RNAP relative to wild-type T7 RNAP (defined as 100) on the same promoter. Note that absolute transcriptional activity levels differ dramatically between bars; only relative levels comparing P314T to wild-type T7 RNAP are shown. Error bars represent the standard deviation of at least three independent assays.

First PACE was used to optimize a phage vector containing wild-type T7 RNAP in place of gIII to remove potential interference from evolutionary improvements to the phage vector rather than to T7 RNAP. The vector was continuously propagated for three days at a lagoon flow rate of 2.0 volumes per hour on host cells containing an AP with the wild-type T7 promoter driving gIII expression. A single plaque presumed to represent vector-optimized T7 RNAP-expressing phage contained a single mutation (P314T) and was used as the starting point for T7 RNAP evolution. It was confirmed that the activity of the P314T mutant does not measurably differ from that of wild-type T7 RNAP (FIG. 12). It was examined whether this optimized T7 polymerase-expressing phage was able to propagate with an AP containing the T3 promoter under the weakest possible selection stringency. Phage vectors containing T7 RNAP survived continuous dilution with host cells containing the T7 promoter AP but failed to propagate and were washed out of the lagoon when diluted instead with host cells containing the T3 promoter AP. Consistent with the lack of reported T7 RNAP variants capable of recognizing the T3 promoter, these results suggest that no immediately accessible mutants possess sufficient T3 promoter activity to propagate continuously on the complete T3 promoter.

Figure 5A:
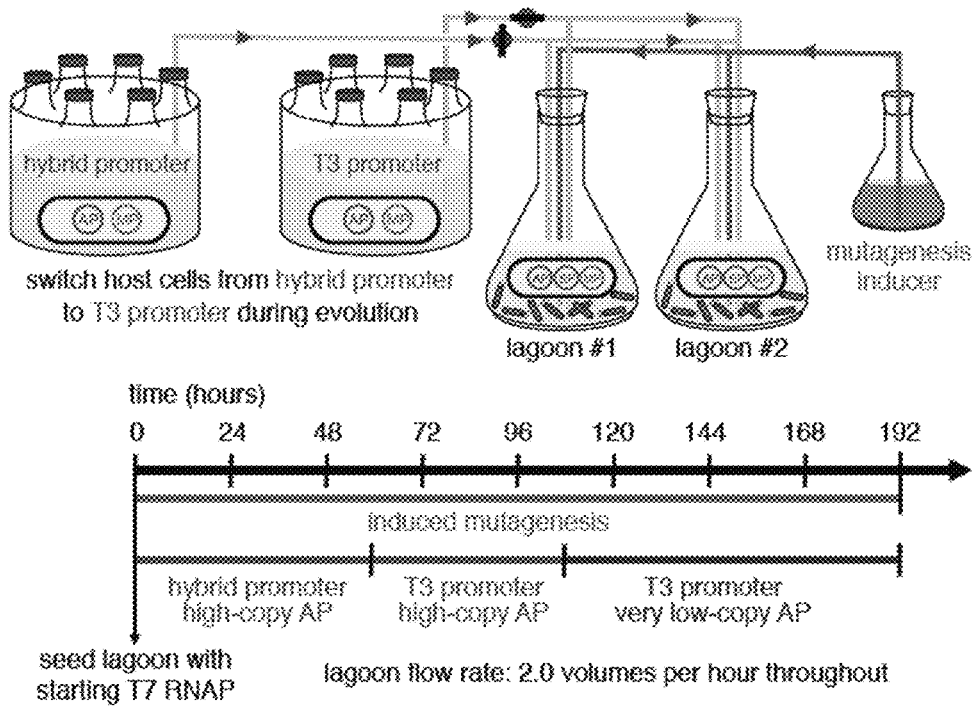
FIGS. 5A to 5D. Evolution of T7 RNAP variants that recognize the T3 promoter.

It was then tested whether T7 RNAP mutants with T3 promoter recognition activity could be evolved by using PACE to first evolve T7 RNAP mutants to recognize a hybrid promoter with the T7 promoter base at the important −11 position but all other positions changed to their T3 promoter counterparts, then simply switching to host cells harboring the complete T3 promoter AP. T7 RNAP phage vectors were propagated on the hybrid T7/T3 promoter AP in two initially identical lagoons in parallel at a constant flow rate of 2.0 volumes per hour for 60 hours, then on the T3 promoter AP for 48 hours, and finally on a high-stringency, single copy T3 promoter AP for 84 hours (FIG. 5A).

In both lagoons phage persisted after 7.5 days total of PACE, surviving a net dilution of $10^{170}$ fold, the equivalent of ~550 phage population doublings and ~200 rounds of evolution by the average phage. Phage vectors were isolated, sequenced, and characterized from each lagoon after 48, 108, and 192 hours. Up to eight non-silent mutations in a single T7 RNAP gene were observed at 48 hours, up to ten non-silent mutations per clone were observed at 108 hours, and up to 11 non-silent mutations per clone were observed at 192 hours. In addition, several mutations in promoters driving T7 RNAP expression were observed in multiple clones although none of these became predominant during the course of the evolution.

Figure 5B:
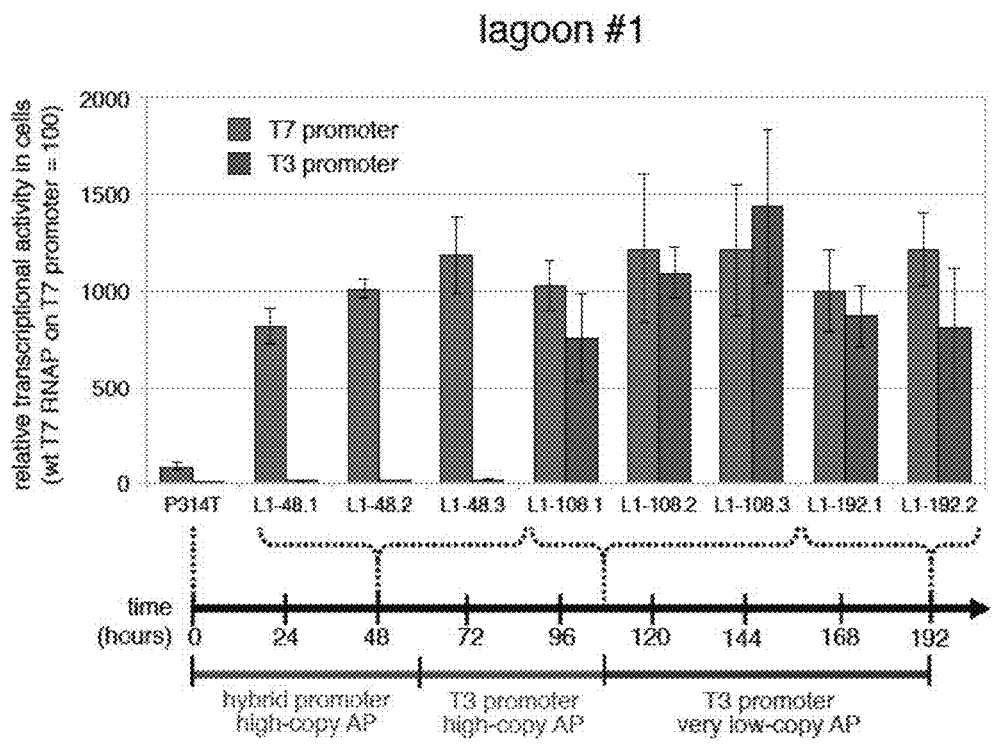
Figure 5C:
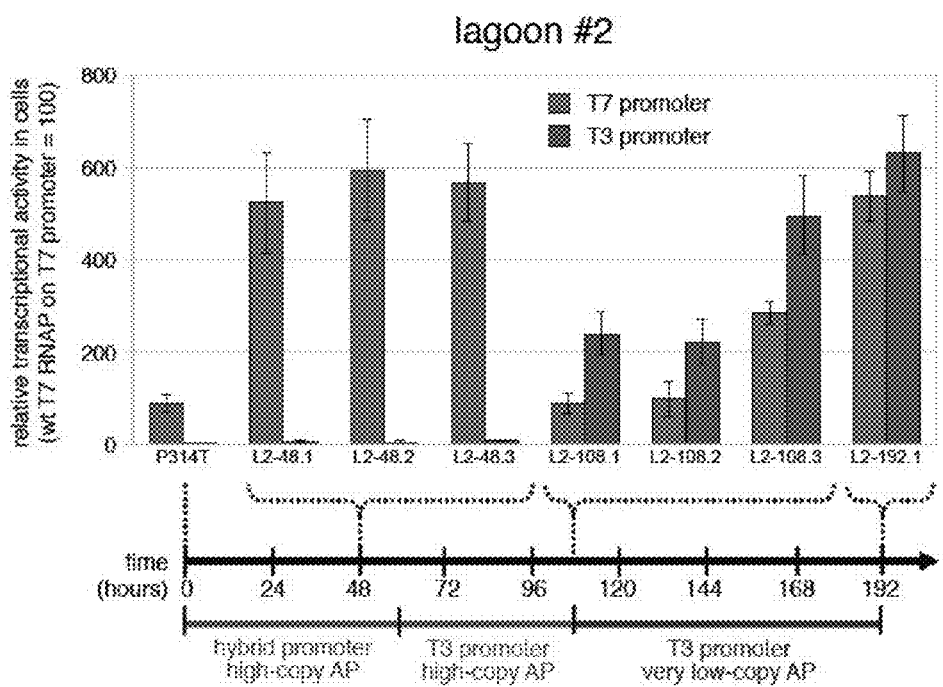

Protein-encoding regions (without upstream promoter sequences) of evolved mutant T7 RNAP genes were cloned into assay plasmids that quantitatively link transcriptional activity to beta-galactosidase expression in cells.[35] It was defined that 100% activity is that of the starting T7 RNAP on the T7 promoter. The starting T7 RNAP exhibited undetectable (≤3%) levels of activity on the T3 promoter in these cell-based assays. At 48 hours, before the switch to the full T3 promoter, PACE-evolved variants of T7 RNAP exhibited up to 20% activity on the T3 promoter (≥6-fold improvement; FIGS. 5B and 5C), with a similar increase of at least 6-fold over the starting enzyme on the T7 promoter. All clones isolated from plaques after 108 hours of PACE exhibited at least 200% activity on the T3 promoter, corresponding to a ≥65-fold increase over the starting activity (FIGS. 5B and 5C). Clones isolated after 192 hours of PACE exhibited at least 300% activity on the T3 promoter, ≥100-fold higher than the starting activity (FIGS. 5B and 5C). The T3 promoter recognition activity of the most active clone improved by ≥300-fold over the 7.5-day course of the experiment, representing a shift from undetectable activity in cells to nearly ten times the activity of wild type T7 RNAP on the wild type T7 promoter.

Despite the lack of an explicit negative selection against wild-type T7 promoter recognition, some clones isolated after 108 and 192 hours of PACE exhibited lower T7 promoter recognition activity than their ancestors, presumably through genetic drift in the absence of selection pressure to recognize the T7 promoter (FIGS. 5B and 5C). One clone, L2-108.2, exhibited 270% of the target activity on the T3 promoter and only 100% activity on the T7 promoter, representing a net ≥100-fold change in specificity compared with wild-type T7 RNAP. These results collectively establish the ability of PACE to very rapidly evolve large changes in enzyme activity and specificity with minimal intervention by the researcher.

Figure 5D:
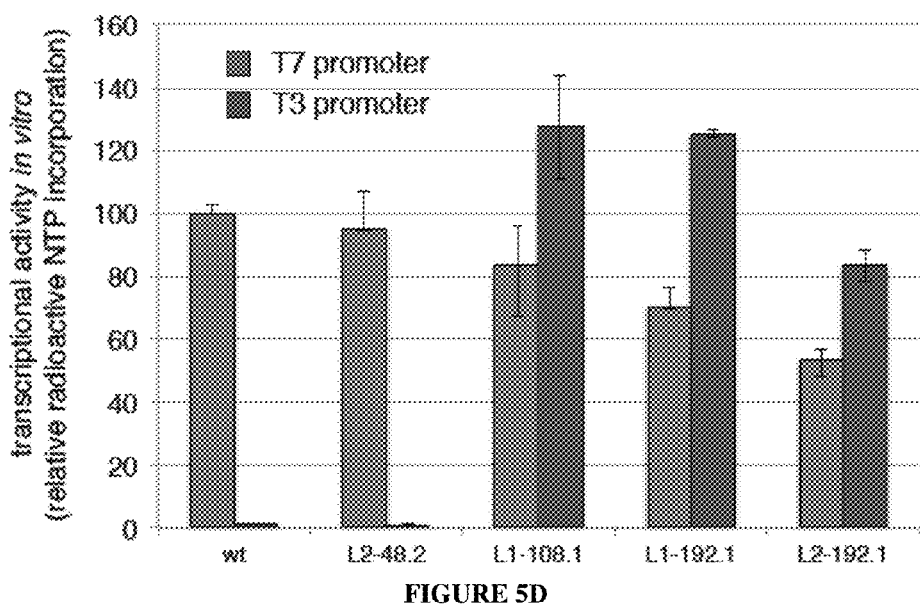
Figure 6:
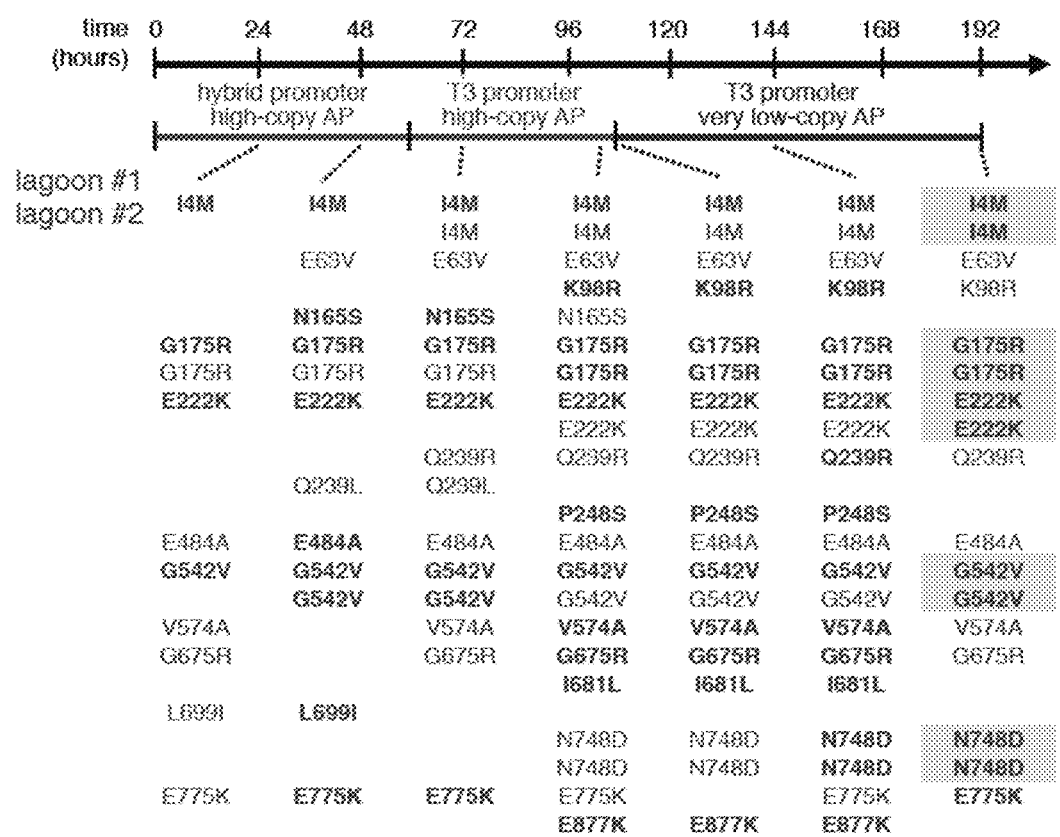
FIG. 6. Mutational analysis of PACE-evolved T7 RNAP variants that recognize the T3 promoter. Mutations identified in T7 RNAP clones at various time points from lagoons 1 and 2 are shown. Bolded mutations were predominant in the respective lagoon based on whole-pool sequencing. Mutations highlighted in the 192 hour column represent changes convergently evolved in lagoon 1 and lagoon 2.

Several evolved T7 RNAP mutants were also purified and assayed in vitro using standard radioactive nucleotide incorporation assays.[36] Purified T7 RNAP mutants exhibited activity levels consistent with the cell-based assays of up to 90-fold over the starting T3 promoter recognition activity (FIG. 5D). In vitro activities did not as dramatically exceed the activity of the wild-type T7 RNAP on the T7 promoter, suggesting that evolved improvements in T7 RNAP activity in cells include improvements in features such as expression level, polymerase folding, or stability in addition to improvements in substrate binding or catalytic rate. Mutational analysis of the PACE-evolved T7 RNAP genes revealed basic structure activity relationships among mutant clones (FIG. 6). The N748D mutation known to enable recognition of the T3 base at the −11 position appeared in isolates of both lagoons within 48 hours after shifting to the full T3 promoter (FIG. 6). Two other known mutations observed during PACE are E222K, a known specificity broadener, [33] and K98R, a change to the corresponding amino acid in T3 RNAP that directly contacts the −15 and −16 bases altered in the T3 promoter. These two mutations were never observed in the same clone, suggesting mutual exclusivity or similar effects on RNAP specificity.

Interestingly, the evolutionary dynamics of the two initially identical lagoons differed significantly (FIG. 6). Within 24 hours, lagoon 1 acquired a predominant suite of mutations consisting of I4M, G175R, E222K, and G542V and changed little thereafter until acquiring N748D following exposure to the full T3 promoter. In contrast, lagoon 2 accessed these mutations more slowly before an entirely different set of mutations, including K98R, became predominant at 96 hours, only to be displaced in turn by the same five mutations observed in lagoon 1. The presence of several mutations unique to lagoon 2 throughout the experiment suggests that lagoon cross-contamination did not occur. The distinct evolutionary trajectories of the two lagoons prior to their ultimate convergence upon a set of common mutations highlight the ability to PACE to rapidly discover multiple viable pathways to a target activity in parallel experiments.

Continuous Evolution of T7 RNA Polymerase: Transcript Initiation

T7 RNAP is highly specific for initiation with GTP,[37-39] significantly limiting its usefulness for the in vitro transcription of RNAs that begin with other nucleotides. As initiation has been described as a mechanistically challenging step in transcription, [40] it was attempted to use PACE to evolve T7 RNAP variants capable of initiating transcription with other nucleotides. T7 RNAP is known to initiate with GTP up to several bases downstream of the +1 position if the template is devoid of early guanines in the coding strand. [41] Therefore, accessory plasmids were constructed in which positions +1 through +6 of the gene III transcript were CCCCCC ($iC_6$) or AAAAAA ($iA_6$), as well as a library consisting of randomized bases at those positions ($iN_6$).

Figure 7A:
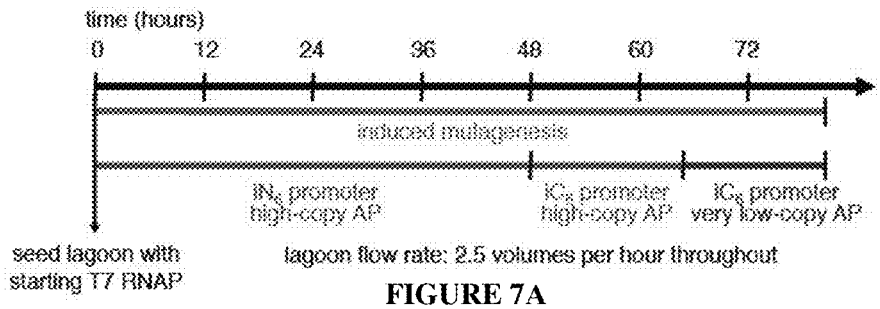
FIGS. 7A to 7C. Evolution of T7 RNAP variants that initiate transcription with CTP.
Figure 7B:
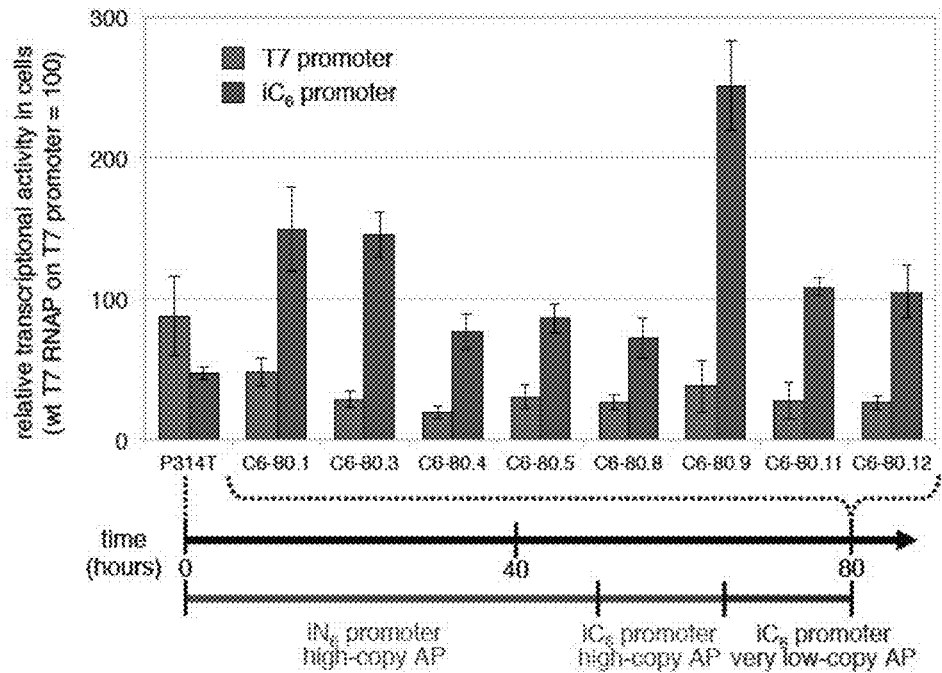
Figure 7C:
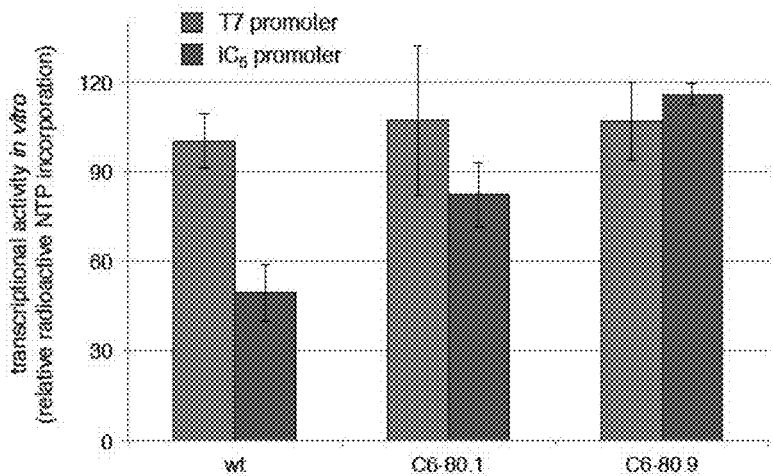

To apply selection pressure towards a pool of variants capable of more promiscuous initiation with non-G bases, vector-optimized T7 RNAP phage was propagated on host cells carrying the $iN_6$ AP library. After 48 hours of selecting for initiation at random bases, it was switched to host cells containing a high-copy $iC_6$ accessory for 16 hours, and finally to cells carrying a low-copy $iC_6$ accessory for 16 hours (FIG. 7A). At a dilution rate of 2.5 volumes/hour, phage survived a total dilution of $10^{-89}$, or ~100 phage generations. Ten sequenced clones from the end of the experiment contained up to 16 total mutations (up to 7 non-silent). It was observed that wild-type T7 RNAP retains a surprising amount of activity [41] on the $iC_6$ promoter (50% of that on the wild-type promoter). All PACE-evolved clones exhibited at least 80% activity on an $iC_6$ promoter in cell-based assays, with the most active clone exhibiting 280% activity, an improvement of 5.3-fold (FIG. 7B). In vitro transcription assays of purified mutant T7 RNAP proteins confirmed the 50% activity of wild-type T7 RNAP on the $iC_6$ promoter, with evolved variants exhibiting improvements of up to 2.3-fold (FIG. 7C). As in the case of the proteins evolved to recognize the T3 promoter, it can be inferred that the somewhat higher cellular activities of $iC_6$-evolved variants are due to improvements in protein folding and stability.

Mutational analysis revealed that the H524N and A827V mutations were conserved among all 12 sequenced clones, presumably arising very early during PACE. In addition, all clones contained either K577M or both C125R and S128R. Several clones contained all five mutations, including the most active clone assayed, suggesting that both observed sets of mutations increase activity and are mutually compatible. Of the five mutations, only C125R and S128R are predicted to be capable of contacting and stabilizing the newly initiated RNA, although A827V is in close proximity to the active site.

Figure 8A:
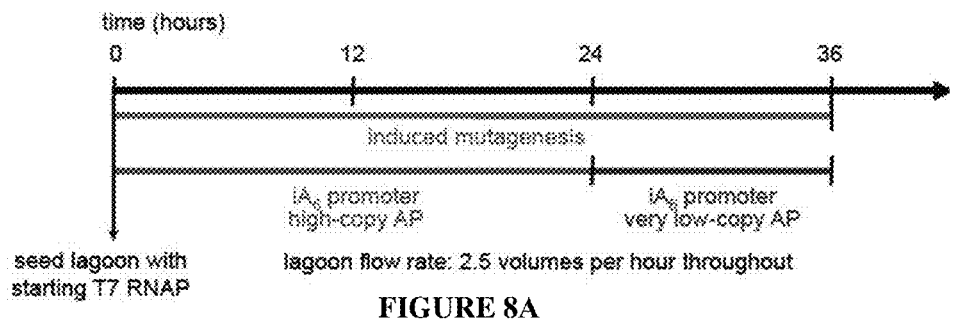
FIGS. 8A to 8C. Evolution of T7 RNAP variants that initiate transcription with ATP.
Figure 13:
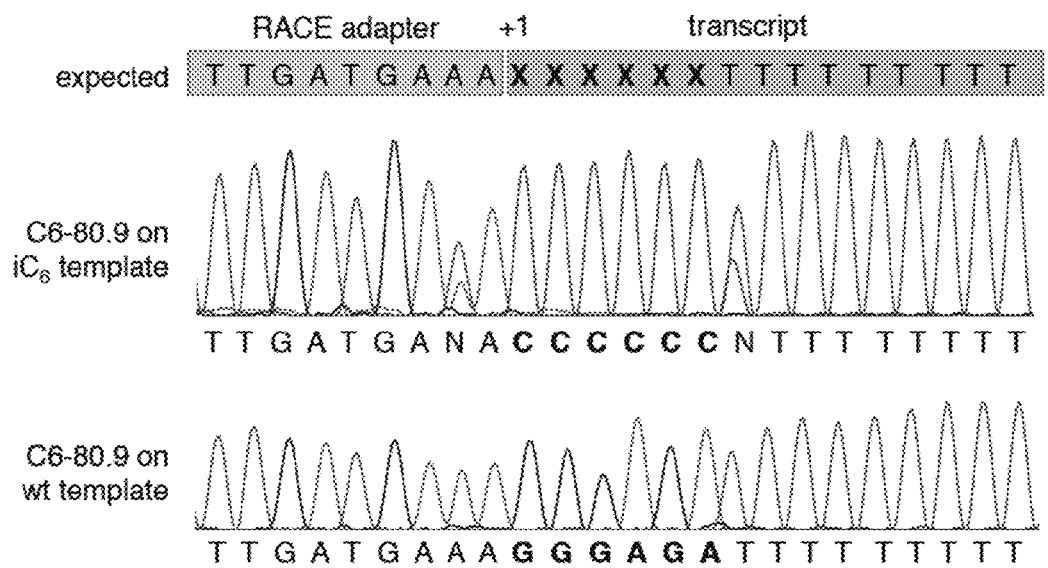
FIG. 13. RNA sequences of transcription products from the C6-80.9 evolved polymerase enzyme. The DNA sequence chromatograms are from RACE analysis of the C6-80.9 evolved polymerase transcribing either the $iC_6$ template (upper trace) or the wild-type template (lower trace). Initiation occurred with the template-encoded bases rather than non-templated nucleotides. Sequences correspond, from top to bottom, to SEQ ID NO: 33-35, respectively.

Although the requirements of functional pIII or LacZ protein in the above experiments ensure that evolved RNA polymerases retain overall sequence fidelity, it is in principle possible that transcription is initiated with non-templated nucleotides rather than the base programmed by the template. To test this possibility, RNA transcripts generated by evolved polymerase C6-80.9 on both the $iC_6$ template and the wild-type template (which initiates transcription with GGGAGA) were sequenced by the RACE method. For both wild-type and $iC_6$ templates, transcripts were initiated with the template-directed bases rather than nontemplated nucleotides. (FIG. 13) As a final evolutionary challenge, PACE was used to rapidly evolve polymerases that can initiate transcription using an $iA_6$ promoter. Starting phage was propagated in host cells with a high-copy $iA_6$ AP for 24 hours, followed by a 30:70 high-copy:single-copy mixture of host cells for 12 hours (FIG. 8A). At a dilution rate of 2.5 volumes per hour, phage survived a total dilution of $10^{40}$ and experienced an average of ~45 rounds of replication under selective conditions. Of six sequenced clones isolated after only 36 hours of evolution, all exhibited at least four non-silent mutations, with one clone possessing seven non-silent mutations.

Figure 8B:
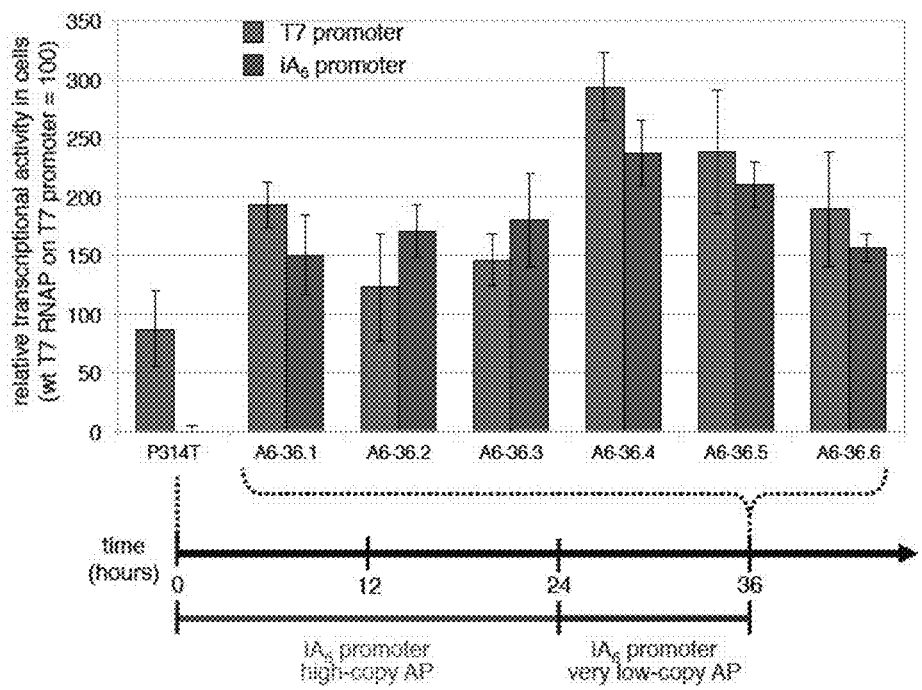
Figure 8C:
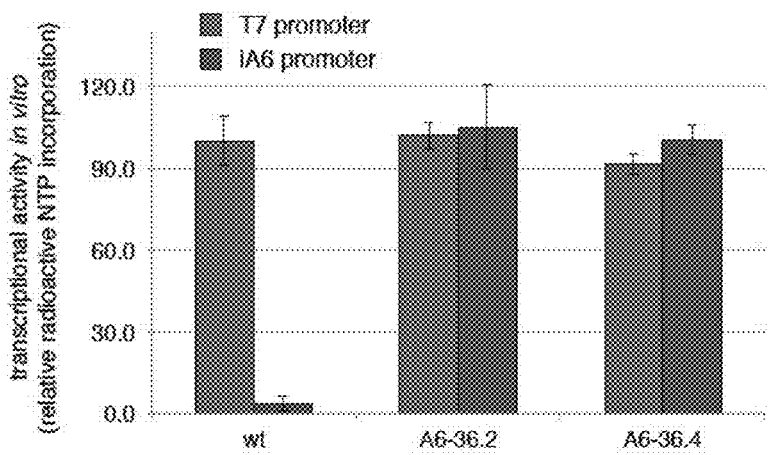

Starting from undetectable initial activity (<3%), all six evolved clones exhibited at least 270% activity on the $iA_6$ promoter in cell-based assays, representing an improvement of at least 33-fold over the starting activity, while retaining 120% activity on the wild-type promoter (FIG. 8B). The most active evolved clone exhibited 430% activity on the $iA_6$ promoter, corresponding to ≥51-fold improvement in activity. In vitro transcription with purified variants yielded activities on the $iA_6$ promoter that are comparable to that of wild type T7 RNAP on the wild-type promoter, an improvement of at least 28-fold in activity (FIG. 8C).

All six characterized $iA_6$-derived clones emerging from PACE contained K93T, S397R, and S684Y mutations, while three of the six also contained S228A. Three of the four mutated residues are predicted to be distant from the nascent RNA and the active site, suggesting that distal changes to the promoter-binding regions of T7 RNAP may result in conformational changes in the active site that better accommodate initiation with adenosine.

In contrast, residue 397 is thought to directly contact the nascent RNA strand, [42] suggesting a direct role for S397R in allowing efficient initiation of $iA_6$ transcripts.

Continuous Negative Selection

Selecting solely for activity on a new target substrate without counter-selection against activity on non-target substrates is likely to result in enzymes with broadened, rather than altered, specificity. Negative selection strategies that exert evolutionary pressure against undesired activities, including poor specificity, are useful to avoid or minimize undesired off-target activity, and allow the evolution of enzymes with high specificity, by linking undesired activities to the inhibition of phage propagation (FIG. 17).

A negative selection strategy was developed in which the selection stringency can be fine-tuned, and in which selection is dependent on the ratio of desired and undesired activities, rather than the absolute level of the undesired activity. A dominant negative variant of pIII was identified that satisfies both of these criteria. This variant ("pIII-neg") comprises the two N-terminal domains of pIII fused to a truncated, termination-incompetent C-terminal domain as described in Bennett, N. J.; Rakonjac, J., Unlocking of the filamentous bacteriophage virion during infection is mediated by the C domain of pIII. *Journal of Molecular Biology* 2006, 356 (2), 266-73; the entire contents of which are incorporated herein by reference. This C-terminal domain allows incorporation into a progeny phage but is unable to catalyze the unlocking of the particle for entry during infection, rendering the progeny phage noninfectious. Furthermore, when this variant is present in a phage containing wild-type pIII (five total pIII molecules are incorporated into each phage), pIII-neg exhibits a dominant negative effect by blocking the unlocking cascade normally catalyzed by wild-type pIII (FIG. 17).

Because this negative selection agent is a protein, pIII-neg, the stringency of counterselection can be tuned by varying the strength of the RBS upstream of the pIII-neg coding region, thereby allowing for a defined modulation of the level of penalty incurred for a given degree of undesired activity. Furthermore, wild-type pIII and pIII-neg compete for incorporation into a progeny phage particle, which makes the potency of inhibition sensitive to the ratio of the desired and undesired activities, rather than just the absolute level of undesired activity.

Figure 17:
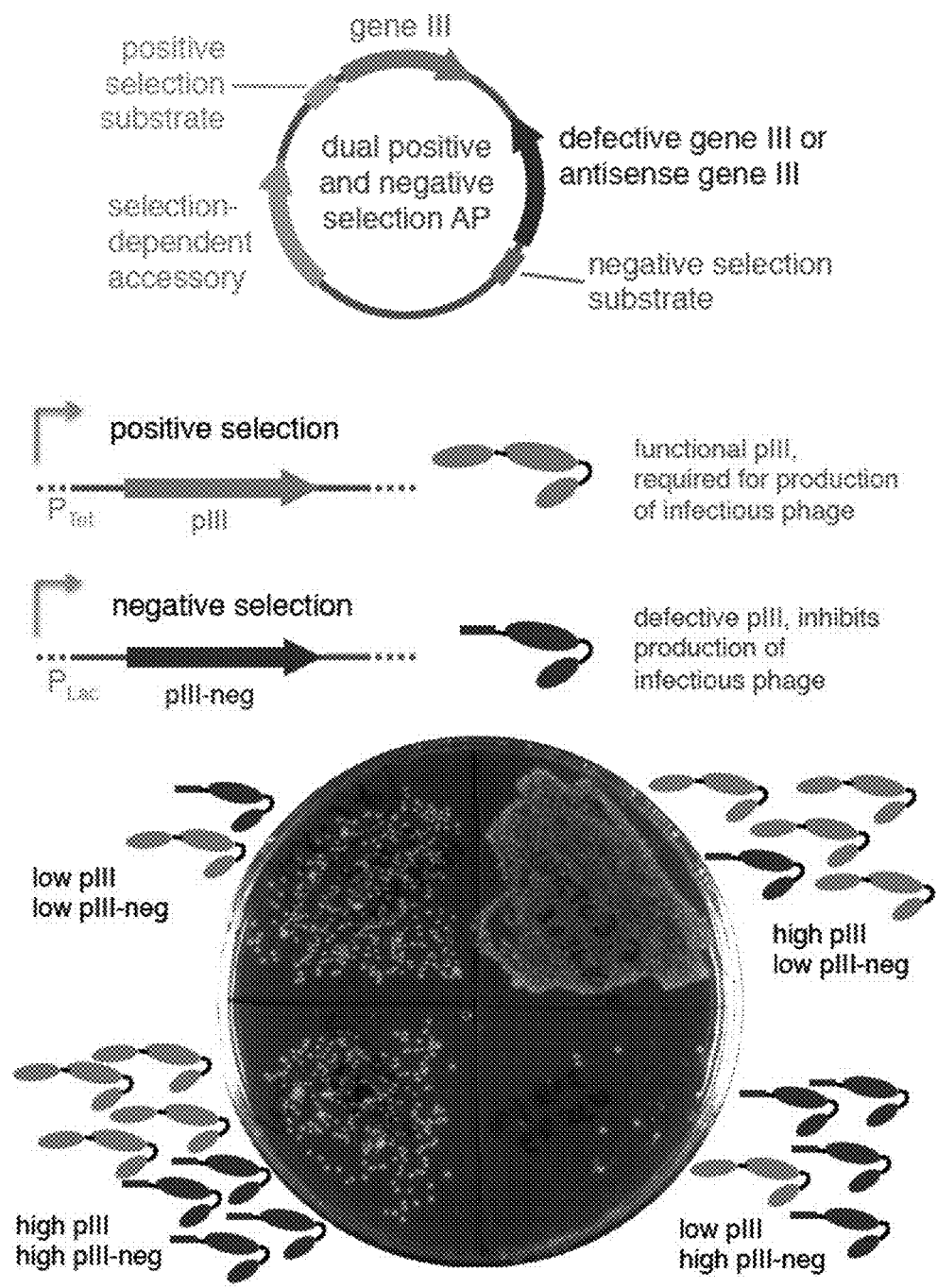
FIG. 17. Negative selection strategy for PACE.

A dual selection accessory plasmid was constructed (FIG. 17). The dual selection plasmid comprises a wild-type pIII coding sequence placed under the control of an inducible promoter ($P_{Tet}$), and a pIII-neg coding sequence placed under the control of a different inducible promoter ($P_{Lac}$). The two pIII transgenes were expressed at different levels in cells producing phage particles (low wt pIII/low pIII-neg; high wt pIII/low pIII-neg; high wt pIII/high pIII-neg; and low wt pIII/high pIII-neg, respectively), and infectivity of the resulting phage was evaluated (FIG. 17). The infectivity of the resulting progeny phage reflects the ratio of wildtype pIII expression to pIII-neg expression, rather than merely reflecting expression levels of either pIII variant alone.

In order to obtain a T7 RNA polymerase that specifically recognizes a T3 promoter but has minimal or no activity on a T7 promoter, an accessory plasmid is constructed in which a T3 promoter sequence drives expression of a wt pIII coding sequence (positive selection), and a T7 promoter drives expression of pIII-neg. A PACE procedure is then performed as described herein, starting with wild type T7 RNA polymerase, or an evolved T7 RNA polymerase exhibiting transcriptional activity on a T3 promoter. It is expected that the evolution products obtained from this dual selection PACE procedure exhibit strong transcriptional activity on a T3 promoter, and little or no activity on a T7 promoter.

Continuous Selection for Protease Activity

Figure 18:
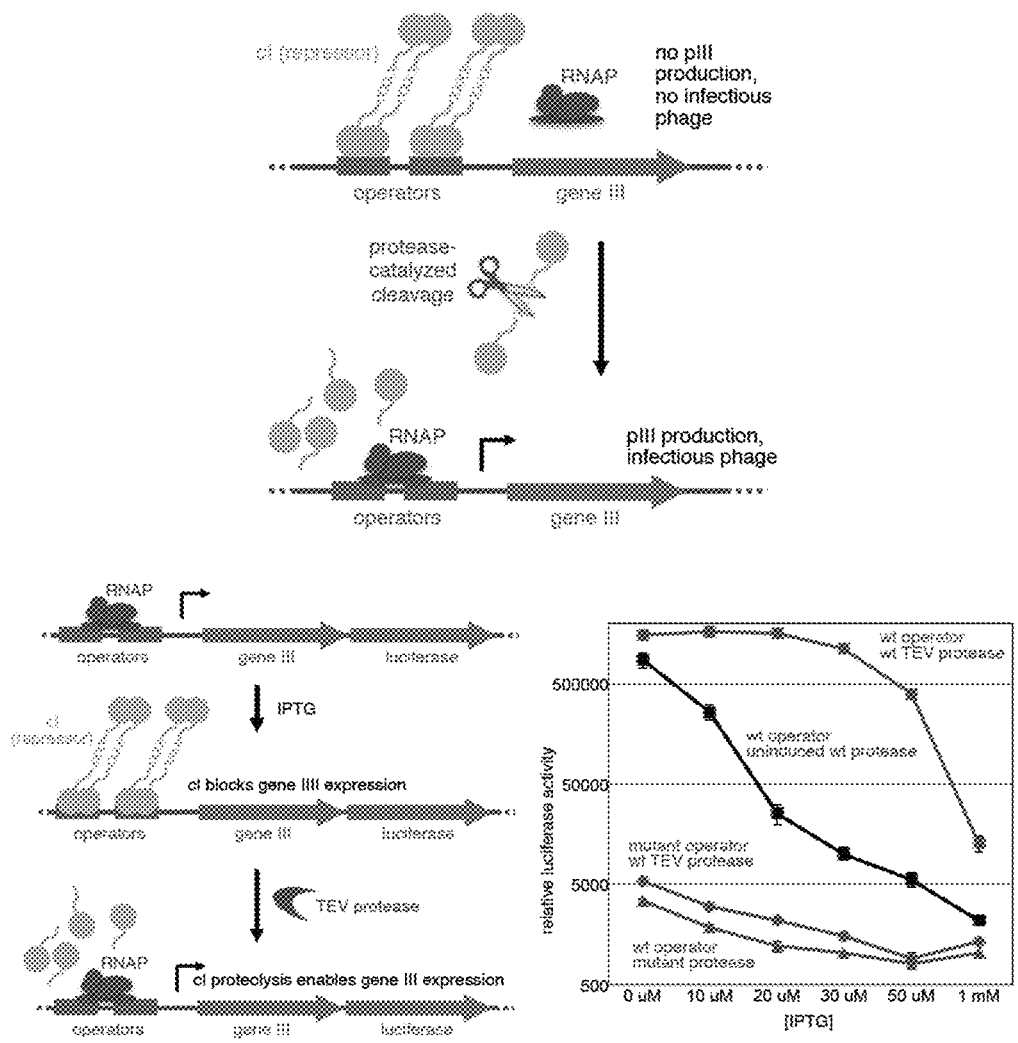
FIG. 18. PACE strategy for the evolution of proteases using cI repressors comprising a target protease recognition site.

For continuous evolution of proteases with tailor-made protein cleavage specificities, a selection strategy is devised that links target proteolysis to phage propagation. This linkage is achieved, in some embodiments, by using a previously reported lambda repressor-based strategy that links protease activity with gene expression by rendering the lambda repressor protein sensitive to site-specific proteolysis (see, e.g., Sices, H. J.; Kristie, T. M., A genetic screen for the isolation and characterization of site-specific proteases. *Proc Natl Acad Sci USA* 1998, 95 (6), 2828-33; and Sices, H. J.; Leusink, M. D.; Pacheco, A.; Kristie, T. M., Rapid genetic selection of inhibitor-resistant protease mutants: clinically relevant and novel mutants of the HIV protease. *AIDS Res Hum Retroviruses* 2001, 17 (13), 1249-55, the entire contents of each of which are incorporated herein by reference). Lambda repressor (cI) contains an N-terminal DNA binding domain and a C-terminal dimerization domain connected by a long flexible linker. Each cI dimer binds cooperatively to operator sites within the lambda pR promoter and represses transcription upon binding. This high-affinity DNA binding requires cI dimerization since free monomeric N-terminal domains bind only weakly to their operator half-sites. Therefore, the separation of the N- and C-terminal domains of cI by proteolysis results in decreased binding to the operator sites and derepresssion of the pR promoter, which in turn can drive pIII production (FIG. 18). The highly cooperative nature of cI binding ensures that promoter activation is very responsive to relatively modest decreases in the concentration of intact cI.

A pIII expression construct was generated in which a pR promoter (containing cI binding sites) drives expression of pIII and luciferase (FIG. 18). The expression construct was expressed in cells expressing cI comprising a TEV protease cleavage site (ENLYFQ(G/S), SEQ ID NO: 29) within the interdomain linker. The cI was expressed from an inducible IPTG promoter. The expression of cI was modulated by the addition of various concentrations of IPTG. Increased levels of IPTG resulted in increasing repression of the pR promoter, while simultaneous expression of TEV protease from an arabinose-inducible promoter resulted in a dramatic (>100-fold) stimulation of gene expression (FIG. 18). This transcriptional activation depended on both the catalytic activity of TEV (the active site mutant TEV C151A does not stimulate expression) and the proper recognition site within the cI linker (mutation of the P1 position glutamine to alanine abolishes activation by WT TEV protease).

These results establish a strong linkage between protease cleavage activity and an increase in pIII expression that is useful for PACE protease selection. The finding that high concentrations of cI keep pR substantially repressed even in the presence of TEV protease activity (FIG. 18), allows for tunable protease selection stringency.

Figure 19:
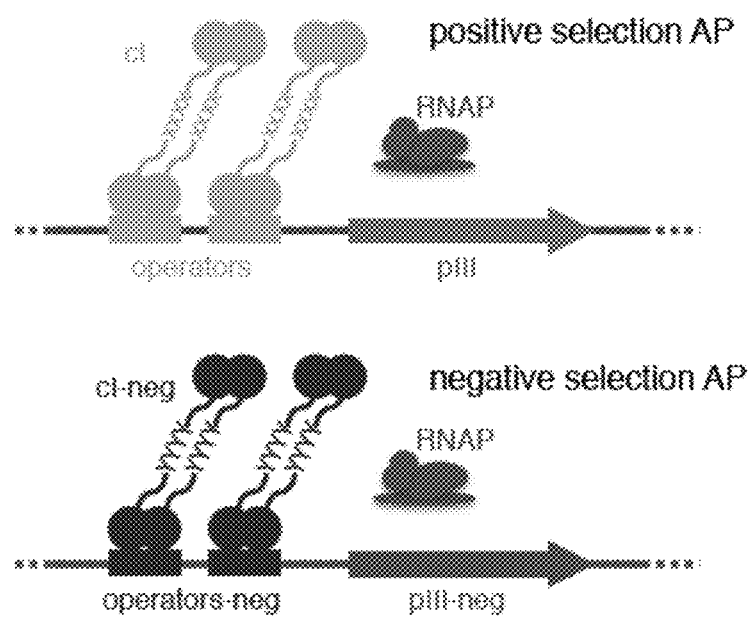
FIG. 19. Accessory plasmid for dual protease selection.

A negative selection for protease activity targeting similar, but off-target recognition sites, is desirable in some embodiments. Further, a negative selection can be used to ensure that the positive selection applies pressure for cleavage of the intended recognition site within the cI linker, and not elsewhere within cI. A negative selection is established by installing into the AP an analogous cI-repressed expression cassette that results in pIII-neg expression (FIG. 19). In this cassette, undesired protease recognition site(s) are incorporated into the linker of a cI variant ("cI-neg") that is orthogonal to wild-type cI in both dimerization specificity and DNA-binding specificity. Such orthogonal cI variants are known from related lambda-family phages (see, e.g., Wharton, R. P.; Ptashne, M., Changing the binding specificity of a repressor by redesigning an alphahelix. *Nature* 1985, 316 (6029), 601-5; and Wharton, R. P.; Ptashne, M., A new-specificity mutant of 434 repressor that defines an amino acid-base pair contact. *Nature* 1987, 326 (6116), 888-91, the entire contents of each of which are incorporated herein by reference). These cI-neg variants are highly similar to cI, apart from DNA sequence specificity differences required to impart orthogonality. When localized upstream of pIII-neg (through use of a pR promoter variant with cognate binding sites for cI-neg), the cleavage of cI-neg will result in expression of pIII-neg and inhibition of phage production (FIG. 19). Thus, a protease variant that cleaves at the undesired recognition site or within an unintended region of the repressor that is common to both cI and cI-neg (most of the repressor molecule) will produce fewer infectious progeny phage than variants with more specific activity against the desired recognition site.

Conclusion

Figure 14:
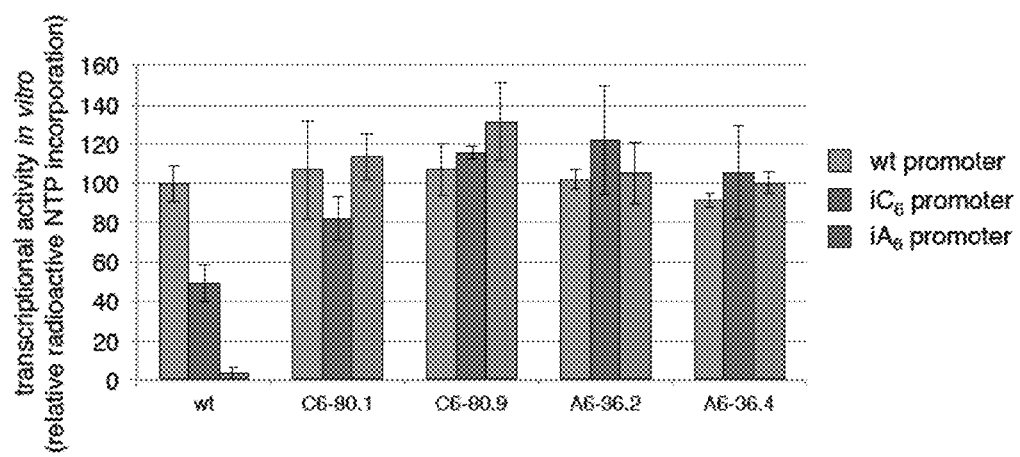
FIG. 14. In vitro transcription activity of T7 RNAP mutants evolved to initiate on the $iC_6$ and $iA_6$ promoters assayed on wild-type, $iC_6$, and $iA_6$ promoters. Transcriptional activity was measured in vitro using a standard radioactive nucleotide incorporation assay. All four variants assayed exhibit the ability to initiate transcription with wild-type-like efficiency on wild-type, $iC_6$, and $iA_6$ promoters. Error bars represent the standard deviation of at least three independent assays.

All four of the evolved T7 RNAP variants assayed in vitro exhibit the ability to initiate transcription using $iC_6$, $iA_6$, and wild-type templates with efficiencies comparable to that of wild-type T7 RNAP initiating with the wild-type template (FIG. 14), and therefore may represent improved, more general T7 RNAP variants for routine in vitro transcription.

Each of the three PACE experiments yielded T7 RNAP variants with significantly higher in vivo activities than that of wild-type T7 RNA polymerase transcribing the wild-type T7 promoter. PACE also revealed different combinations of mutations that achieve this effect on the T7, T3, $iC_6$, and $iA_6$ promoters, indicating the existence of multiple accessible evolutionary paths conferring increased activity in cells. That none of these paths were taken by wild-type T7 phage suggests that there was no selection pressure for more efficient polymerization during the evolution of T7 bacteriophage, that retaining specificity requires lower overall activity, or a combination of both possibilities.

By rendering bacteriophage infection dependent upon a molecular activity of interest, the efficiency of the phage life cycle was harnessed to enable the continuous directed evolution of proteins or, in principle, other gene-encoded molecules without the need for in vitro library creation, gene harvesting, or gene manipulation steps. The PACE system can be assembled entirely from a modest collection of commercially available equipment (listed in Table 2) and does not require the manufacture of any specialized components.

TABLE 2

| | Source | Catalog # | Purpose |
|---|---|---|---|
| Turbidostat | | | |
| BioProbe flask, 0.5 L | Bellco Glass | 1965-97005 | Turbidostat, small |
| BioProbe flask, 1 L | Bellco Glass | 1965-97001 | Turbidostat, medium |
| BioProbe flask, 3 L | Bellco Glass | 1965-97003 | Turbidostat, large |
| Corning Scholar 171 magnetic stirrer | Thermo Fisher Scientific | 11-497-22 | Stirs turbidostats |
| Corning PC-240 magnetic stirrer | Thermo Fisher Scientific | 114973C | Stirs large turbidostats |
| GL32 probe holder | Bellco Glass | 1965-97010 | Holds cell density probe |
| GL45 septa | Bellco Glass | C139-545SS | Port access |
| GL32 septa | Bellco Glass | C139-532SS | Port access |
| GL45 open caps | Bellco Glass | C139-545HTSC | Port access |
| GL32 open caps | Bellco Glass | C139-532HTSC | Port access |
| Large autoclavable venting filter 6-10 mm | VWR | 28137-652 | Turbidostat venting |
| 24 VDC 3-way valve | Bio-Chem Fluidics | 100P3MP24-05S | Controlling media flow |
| Masterflex L/S economy variable drive | Cole Parmer, Inc | 07554-80 | Fluid transfer |
| L/S 8-channel, 3-roller pump head | Cole Parmer, Inc | 07519-05 | Fluid transfer |
| Masterflex L/S small cartridges | Cole Parmer, Inc | 07519-80 | Fluid transfer |
| Tygon two-stop pump tubing, L/S 14 | Cole Parmer, Inc | 06416-14 | Fluid transfer |
| Tubing, pharmed, 2.79 mm ID, 100' | Cole Parmer, Inc | 95809-48 | Fluid transfer |
| Male luer with lock ring × 1/8" hose barb, PP, 25/pk | Cole Parmer, Inc | 45503-04 | Fluid transfer |
| Female luer × 1/8" hose barb adapter, PP, 25/pk | Cole Parmer, Inc | 45500-04 | Fluid transfer |
| Nalgene jerrican waste container | Thermo Fisher Scientific | 2240 | Waste container |
| Needle, blunt disposable | VWR | BD305180 | Fluid addition |
| 20 L carboys w/handle | VWR | 16101-109 | Media vessel |
| Polyvent filling/venting closure | VWR | 16225-229 | Media cap |
| Needle, blunt end 18 G × 6" | VWR | 20068-682 | Waste withdrawal |
| Electrical equipment | | | |
| TruCell2 cell density meter | Finesse, Inc. | CDS-PRB-10-225 | Density monitoring |
| L10200P digital panel meter | Laurel Electronics | L10200P | Valve control |
| Experimentor 350 solderless breadboard | Global Specialties | EXP-350 | Valve control |
| 1N4001 Micromini Silicon Diode, 50 V 1 A | Radio Shack | 276-1101 | Valve control |
| UL-recognized hookup wire | Radio Shack | 278-1224 | Wiring |
| Germicidal UV lamp | American Air & Water | SM-36-2GR | Sterilization |
| Lagoons | | | |
| Pyrex 100 mL bottles | VWR | 16157-103 | Lagoon vessel |
| Pyrex 1 L bottle | VWR | 16157-191 | Arabinose supplement |
| GL45 septa | Bellco Glass | C139-545SS | Port access |
| GL45 open caps | Bellco Glass | C139-545HTSC | Port access |
| Thermo Variomag Poly 15 magnetic stirrer | VWR | 89030-746 | Stirring |
| Needle, blunt disposable | VWR | BD305180 | Fluid addition |
| Needle, blunt end 18 G × 6" | VWR | 20068-682 | Waste withdrawal |
| Autoclavable 0.2 um filters | VWR | 28137-650 | Venting |
| L/S brushless programmable drive | Cole Parmer, Inc | 07550-50 | Fluid transfer |
| L/S 8-channel pump head for microbore tubing | Cole Parmer, Inc | 07534-08 | Fluid transfer |
| Microbore two-stop tube sets, silicone; 2.06 mm ID. | Cole Parmer, Inc | 06421-42 | Lagoon to waste |
| Microbore two-stop tube sets, silicone; 1.42 mm ID. | Cole Parmer, Inc | 06421-34 | Turbidostat to lagoon |
| Microbore two-stop tube sets, silicone; 0.82 mm ID. | Cole Parmer, Inc | 06421-26 | Supplement to lagoon |
| Male luer with lock ring × 1/16" hose barb, PP, 25/pk | Cole Parmer, Inc | 45503-00 | Fluid transfer |
| Male luer with lock ring × 3/32" hose barb, PP, 25/pk | Cole Parmer, Inc | 45503-02 | Fluid transfer |

TABLE 2-continued

| | | | |
|---|---|---|---|
| Male luer with lock ring × ⅛" hose barb, PP, 25/pk | Cole Parmer, Inc | 45503-04 | Fluid transfer |
| Female luer × 1/16" hose barb adapter, PP, 25/pk | Cole Parmer, Inc | 45500-00 | Fluid transfer |
| Female luer × 3/32" hose barb adapter, PP, 25/pk | Cole Parmer, Inc | 45500-02 | Fluid transfer |
| Female luer × ⅛" hose barb adapter, PP, 25/pk | Cole Parmer, Inc | 45500-04 | Fluid transfer |
| Tubing, pharmed, 0.89 mm ID, 100 ft | Cole Parmer, Inc | 95809-26 | Fluid transfer |
| Tubing, pharmed, 1.42 mm ID, 100 ft | Cole Parmer, Inc | 95809-34 | Fluid transfer |
| Tubing, pharmed, 2.06 mm ID, 100 ft | Cole Parmer, Inc | 95809-42 | Fluid transfer |
| Turbidostat Media | | | |
| Potassium phosphate dibasic, 50 kg | VWR | EM-PX1570-20 | Turbidostat media |
| Potassium phosphate monobasic, 10 kg | United States Biological | P5110 | Turbidostat media |
| Ammonium sulfate, 5 kg | United States Biological | A1450 | Turbidostat media |
| Tween 80 | VWR | 100511-562 | Turbidostat media |
| Glucose, 10 kg | United States Biological | G3050 | Turbidostat media |
| Sodium citrate dihydrate, 5 kg | United States Biological | S5001 | Turbidostat media |
| Casamino acids, 10 kg | United States Biological | C2080 | Turbidostat media |
| L-leucine | United States Biological | L2020-05 | Turbidostat media |
| Magnesium sulfate, anhydrous | Sigma Aldrich | 246972 | Turbidostat media |
| Carbenicillin | Gold Biotechnology | C-103-100 | Turbidostat media |
| Spectinomycin | Gold Biotechnology | S-140-25 | Turbidostat media |
| Tetracycline HCl | Gold Biotechnology | T-101-25 | Turbidostat media |
| Nalgene 500 mL filter unit, 0.2 um pore size | VWR | 450-0020 | Turbidostat media |
| L-arabinose | Gold Biotechnology | A-300-1 | Inducing mutagenesis |
| Standard Media | | | |
| 2xYT, 10 kg | United States Biological | T9200 | Standard culture |
| LB broth Miller, 10 kg | United States Biological | L1520 | Standard culture |
| Kanamycin | Gold Biotechnology | K-120-25 | Standard culture |
| Chloramphenicol | Gold Biotechnology | C-119-5 | Standard culture |
| X-Gal | Gold Biotechnology | X4281C | Standard culture |
| PCR | | | |
| Oligonucleotides | Integrated DNA Technologies | N/A | Cloning |
| HotStart Phusion II DNA polymerase | New England Biolabs | F-549L | PCR |
| dNTPs | Bio-Rad | 170-8874 | PCR |
| DpnI | New England Biolabs | R0176L | Template removal |
| MinElute PCR purification kit | Qiagen | 28006 | PCR cleanup |
| Isothermal assembly and cloning | | | |
| Phusion DNA polymerase | New England Biolabs | F-530-L | Isothermal assembly |
| Taq DNA ligase | New England Biolabs | M0208L | Isothermal assembly |
| T5 DNA exonuclease | Epicentre Biotechnologies | T5E4111K | Isothermal assembly |
| TempliPhi, 500 rxns | GE Healthcare | 25-6400-50 | Isothermal assembly |
| Nicotinamide adenine dinucleotide (NAD) | Sigma Aldrich | N8410 | Isothermal assembly |
| PEG-8000 | Sigma Aldrich | 9510 | Isothermal assembly |

| | Source | Catalog# | Purpose |
|---|---|---|---|
| Activity assays | | | |
| Falcon Microtest 96-well OptiLux plates | BD Biosciences | 353948 | Fluorescence assays |
| M5 plate reader | Molecular Devices | | Fluorescence assays |
| 4-methylumbelliferyl-beta-D-galactopyranoside (MUG) | Gold Biotechnology | MUG1 | Fluorescence assays |
| Misonix CL4 ultrasonic convertor | Misonix | | Protein purification |

TABLE 2-continued

| | | | |
|---|---|---|---|
| Ni-NTA spin columns | Qiagen | 31014 | Protein purification |
| Amicon Ultra-0.5 30K concentration columns | Millipore | UFC503096 | Protein purification |
| NuPage 4-12% gel | Invitrogen | NP0323BOX | Protein quantification |
| rNTPs | Jena Biosciences | NU-1014L | T7 transcription |
| [α-$^{32}$P]ATP | Perkin-Elmer | BLU003X250UC | Phosphorimaging |
| Ribonuclease T1 | Ambion | AM2283 | Leader cleavage |
| Criterion 5% TBE-urea gel | Bio-Rad | 345-0086 | Phosphorimaging |
| Criterion 10% TBE-urea gel | Bio-Rad | 345-0088 | Phosphorimaging |
| Criterion 15% TBE-urea gel | Bio-Rad | 345-0089 | Phosphorimaging |
| Typhoon Trio | GE Healthcare | 63-0055-87 | Phosphorimaging |
| Phosphor screen | GE Healthcare | 63-0035-44 | Phosphorimaging |
| RACE experiments | | | |
| Turbo DNase | Ambion | AM2239 | Template removal |
| Calf intestinal phosphatase | New England Biolabs | M0290L | Triphosphate removal |
| T4 polynucleotide kinase | New England Biolabs | M0201L | Phosphate addition |
| T4 RNA Ligase I (ssRNA Ligase) | New England Biolabs | M0204L | Ligation |
| Superscript III reverse transcriptase | Invitrogen | 18080093 | Reverse transcription |
| Zero Blunt TOPO cloning kit | Invitrogen | 45-0031 | Subcloning PCRs |
| Bacterial strains | | | |
| Mach1 chemically competent cells | Invitrogen | C862003 | Cloning |
| NEB Turbo chemically competent cells | New England Biolabs | C2984H | Cloning |
| PirPlus DH10βF'DOT cells | Thermo Fisher | MBC1249 | Infection assays |

| Source | Headquarters |
|---|---|
| Bellco Glass | Vineland, NJ |
| Thermo Fisher Scientific | Waltham, MA |
| VWR | Pittsburgh, PA |
| Bio-Chem Fluidics | Boonton, NJ |
| Cole Parmer, Inc | St Louis, MO |
| Finesse, Inc. | San Jose, CA |
| Laurel Electronics | Santa Clara, CA |
| Global Specialties | Wallingford, CT |
| American Air & Water | Hilton Head Island, SC |
| United States Biological | Marblehead, MA |
| Sigma Aldrich | St Louis, MO |
| Gold Biotechnology | St Louis, MO |
| Integrated DNA Technologies | Coralville, IA |
| Bio-Rad | Hercules, CA |
| Qiagen | Valencia, CA |
| Epicentre Biotechnologies | Madison, WI |
| GE Healthcare | Piscataway, NJ |
| BD Biosciences | Franklin Lakes, NJ |
| Perkin-Elmer | Waltham, MA |
| Misonix | Farmingdale, NY |
| Millipore | Billerica, MA |
| Ambion | Austin, TX |

PACE proceeds at a rate of several dozen rounds of mutation, selection, and gene replication per day, representing roughly a 100-fold increase over most current protein evolution methods. These capabilities may be particularly well-suited to address problems or questions in molecular evolution that require hundreds to thousands of generations, or the execution of multiple evolution experiments in parallel. More generally, PACE represents the integration and manipulation of many protein and nucleic acid components in a living system to enable the rapid generation of biomolecules with new activities, a significant goal of synthetic biology.

REFERENCES

1 Yuan, L., Kurek, I., English, J. & Keenan, R. Laboratory-directed protein evolution. Microbiology and Molecular Biology Reviews: MMBR 69, 373-392 (2005).

2 Bloom, J. D. et al. Evolving strategies for enzyme engineering. Curr. Opin. Struct. Biol. 15, 447-452 (2005).

3 Voigt, C. A., Kauffman, S. & Wang, Z. G. Rational evolutionary design: the theory of in vitro protein evolution. Adv. Protein Chem. 55, 79-160 (2000).

4 Mills, D. R., Peterson, R. L. & Spiegelman, S. An extracellular Darwinian experiment with a self-duplicating nucleic acid molecule. Proc. Natl. Acad. Sci. U.S.A. 58, 217-224 (1967).

5 Breaker, R. R. & Joyce, G. F. Emergence of a replicating species from an in vitro RNA evolution reaction. Proc. Natl. Acad. Sci. U.S.A. 91, 6093-6097 (1994).

6 Wright, M. C. & Joyce, G. F. Continuous in vitro evolution of catalytic function. Science (New York, N.Y.) 276, 614-617 (1997).

7 Lincoln, T. A. & Joyce, G. F. Self-sustained replication of an RNA enzyme. Science (New York, N.Y.) 323, 1229-1232 (2009).

8 Wang, L., Jackson, W. C., Steinbach, P. A. & Tsien, R. Y. Evolution of new nonantibody proteins via iterative somatic hypermutation. *Proc. Natl. Acad. Sci. U.S.A.* 101, 16745-16749 (2004).

9 Camps, M., Naukkarinen, J., Johnson, B. P. & Loeb, L. A. Targeted gene evolution in *Escherichia coli* using a highly error-prone DNA polymerase I. *Proc. Natl. Acad. Sci. U.S.A.* 100, 9727-9732 (2003).

10 Makeyev, E. V. & Bamford, D. H. Evolutionary potential of an RNA virus. *J. Virol.* 78, 2114-2120 (2004).

11 Zhou, X., Vink, M., Klaver, B., Berkhout, B. & Das, A. T. Optimization of the Tet-On system for regulated gene expression through viral evolution. *Gene Ther.* 13, 1382-1390 (2006).

12 Davis, J. N. & van den Pol, A. N. Viral Mutagenesis as a Means for Generating Novel Proteins. *J. Virol.* 84, 1625-1630 (2009).

13 Das, A. T. et al. Viral evolution as a tool to improve the tetracycline-regulated gene expression system. *The Journal of Biological Chemistry* 279, 18776-18782 (2004).

14 Wang, H. H. et al. Programming cells by multiplex genome engineering and accelerated evolution. *Nature* 460, 894-898 (2009).

15 Husimi, Y., Nishigaki, K., Kinoshita, Y. & Tanaka, T. Cellstat-a continuous culture system of a bacteriophage for the study of the mutation rate and the selection process of the DNA level. *The Review of Scientific Instruments* 53, 517-522 (1982).

16 Husimi, Y. Selection and evolution of bacteriophages in cellstat. *Advances in Biophysics* 25, 1-43 (1989).

17 Smith, G. P. Filamentous fusion phage: novel expression vectors that display cloned antigens on the virion surface. *Science* 228, 1315-1317 (1985).

18 Riechmann, L. & Holliger, P. The C-terminal domain of TolA is the coreceptor for filamentous phage infection of *E. coli*. *Cell* 90, 351-360 (1997).

19 Click, E. M. & Webster, R. E. Filamentous phage infection: required interactions with the TolA protein. *J. Bacteriol.* 179, 6464-6471 (1997).

20 Nelson, F. K., Friedman, S. M. & Smith, G. P. Filamentous phage DNA cloning vectors: a noninfective mutant with a nonpolar deletion in gene III. *Virology* 108, 338-350 (1981).

21 Rakonjac, J. & Model, P. Roles of pIII in filamentous phage assembly. *J. Mol. Biol.* 282, 25-41 (1998).

22 Calendar, R. *The bacteriophages.* (Oxford University Press US %@ 9780195148503, 2006).

23 Vidal, M. & Legrain, P. Yeast forward and reverse 'n'-hybrid systems. *Nucleic Acids Res.* 27, 919-929 (1999).

24 Joung, J. K., Ramm, E. I. & Pabo, C. O. A bacterial two-hybrid selection system for studying protein-DNA and protein-protein interactions. *Proc. Natl. Acad. Sci. U.S.A.* 97, 7382-7387 (2000).

25 Baker, K. et al. Chemical complementation: a reaction-independent genetic assay for enzyme catalysis. *Proc. Natl. Acad. Sci. U.S.A.* 99, 16537-16542 (2002).

26 Ringquist, S. et al. Translation initiation in *Escherichia coli*: sequences within the ribosome-binding site. *Molecular Microbiology* 6, 1219-1229 (1992).

27 Drake, J. W. A constant rate of spontaneous mutation in DNA-based microbes. *Proc. Natl. Acad. Sci. U.S.A.* 88, 7160-7164 (1991).

28 Fijalkowska, I. J. & Schaaper, R. M. Mutants in the Exo I motif of *Escherichia coli* dnaQ: defective proofreading and inviability due to error catastrophe. *Proc. Natl. Acad. Sci. U.S.A.* 93, 2856-2861 (1996).

29 Opperman, T., Murli, S., Smith, B. T. & Walker, G. C. A model for a umuDCdependent prokaryotic DNA damage checkpoint. *Proc. Natl. Acad. Sci. U.S.A.* 96, 9218-9223 (1999).

30 Raskin, C. A., Diaz, G., Joho, K. & McAllister, W. T. Substitution of a single bacteriophage T3 residue in bacteriophage T7 RNA polymerase at position 748 results in a switch in promoter specificity. *J. Mol. Biol.* 228, 506-515 (1992).

31 Joho, K. E., Gross, L. B., McGraw, N. J., Raskin, C. & McAllister, W. T. Identification of a region of the bacteriophage T3 and T7 RNA polymerases that determines promoter specificity. *J. Mol. Biol.* 215, 31-39 (1990).

32 Klement, J. F. et al. Discrimination between bacteriophage T3 and T7 promoters by the T3 and T7 RNA polymerases depends primarily upon a three base-pair region located 10 to 12 base-pairs upstream from the start site. *J. Mol. Biol.* 215, 21-29 (1990).

33 Ikeda, R. A., Chang, L. L. & Warshamana, G. S. Selection and characterization of a mutant T7 RNA polymerase that recognizes an expanded range of T7 promoter-like sequences. *Biochemistry* 32, 9115-9124 (1993).

34 Raskin, C. A., Diaz, G. A. & McAllister, W. T. T7 RNA polymerase mutants with altered promoter specificities. *Proc. Natl. Acad. Sci. U.S.A.* 90, 3147-3151 (1993).

35 Vidal-Aroca, F. et al. One-step high-throughput assay for quantitative detection of beta-galactosidase activity in intact gram-negative bacteria, yeast, and mammalian cells. *BioTechniques* 40, 433-434, 436, 438 (2006).

36 Martin, C. T. & Coleman, J. E. Kinetic analysis of T7 RNA polymerase promoter interactions with small synthetic promoters. *Biochemistry* 26, 2690-2696 (1987).

37 Ikeda, R. A., Warshamana, G. S. & Chang, L. L. In vivo and in vitro activities of point mutants of the bacteriophage T7 RNA polymerase promoter. *Biochemistry* 31, 9073-9080 (1992).

38 Imburgio, D., Rong, M., Ma, K. & McAllister, W. T. Studies of promoter recognition and start site selection by T7 RNA polymerase using a comprehensive collection of promoter variants. *Biochemistry* 39, 10419-10430 (2000).

39 Milligan, J. F., Groebe, D. R., Witherell, G. W. & Uhlenbeck, O. C. Oligoribonucleotide synthesis using T7 RNA polymerase and synthetic DNA templates. *Nucleic Acids Res.* 15, 8783-8798 (1987).

40 Kuzmine, I., Gottlieb, P. A. & Martin, C. T. Binding of the priming nucleotide in the initiation of transcription by T7 RNA polymerase. *The Journal of Biological Chemistry* 278, 2819-2823 (2003).

41 Brieba, L. G., Padilla, R. & Sousa, R. Role of T7 RNA polymerase His784 in start site selection and initial transcription. *Biochemistry* 41, 5144-5149 (2002).

42 Cheetham, G. M., Jeruzalmi, D. & Steitz, T. A. Structural basis for initiation of transcription from an RNA polymerase-promoter complex. *Nature* 399, 80-83 (1999).

43 Akopian, A., He, J., Boocock, M. R. & Stark, W. M. Chimeric recombinases with designed DNA sequence recognition. *Proc Natl Acad Sci USA* 100, 8688-8691 (2003).

44 Gibson, D. G. et al. Enzymatic assembly of DNA molecules up to several hundred kilobases. *Nat. Methods* 6, 343-345 (2009).

45 Datsenko, K. A. & Wanner, B. L. One-step inactivation of chromosomal genes in *Escherichia coli* K-12 using PCR products. *Proc. Natl. Acad. Sci. U.S.A.* 97, 6640-6645 (2000).

46 Husimi, Y. Selection and evolution of bacteriophages in cellstat. *Advances in Biophysics* 25, 1-43 (1989).

47 Vidal-Aroca, F. et al. One-step high-throughput assay for quantitative detection of beta galactosidase activity in intact gram-negative bacteria, yeast, and mammalian cells. *BioTechniques* 40, 433-434, 436, 438 (2006).

48 Ichetovkin, I. E., Abramochkin, G. & Shrader, T. E. Substrate recognition by the leucyl/phenylalanyl-tRNA-protein transferase. Conservation within the enzyme family and localization to the trypsin-resistant domain. *J. Biol. Chem.* 272, 33009-33014 (1997).

49 Tzagoloff, H. & Pratt, D. The initial steps in infection with coliphage M13. *Virology* 24, 372-380 (1964).

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. An apparatus for continuous evolution of a gene of interest, the apparatus comprising
   (a) a lagoon comprising
      a cell culture vessel comprising a population of M13 phages comprising a gene of interest to be evolved and lacking a functional pIII gene required for the generation of infectious phage particles, and a population of bacterial host cells, wherein
      (1) the M13 phages allow for expression of the gene of interest in the host cells,
      (2) the host cells are suitable host cells for M13 phage infection, replication, and packaging, wherein the M13 phage comprises all phage genes required for the generation of phage particles, except a functional pIII gene;
      (3) the host cells comprise an expression construct encoding the pIII protein, wherein expression of the pIII gene is dependent on a function of a gene product of the gene of interest;
      (4) the host cells comprise an expression construct encoding a dominant-negative pIII protein (pIII-neg), wherein the pIII-neg protein is driven by a promoter the activity of which depends on an undesired function of a gene product encoded by the gene of interest;
      an inflow connected to a turbidostat;
      an outflow;
      a controller controlling inflow and outflow rates; and,
   (b) a turbidostat comprising
      a cell culture vessel comprising a population of fresh host cells;
      an outflow connected to the inflow of the lagoon;
      an inflow connected to a vessel comprising liquid media
      a turbidity meter measuring the turbidity of the culture of fresh host cells in the turbidostat; and,
      a controller controlling the inflow of sterile liquid media and the outflow into the waste vessel based on the turbidity of the culture liquid.

2. The apparatus of claim 1, wherein the bacterial host cells are *E. coli* cells.

3. The apparatus of claim 1, wherein the bacterial host cells express pIII under the control of a conditional promoter, the activity of which depends on an activity of a product encoded by the gene of interest.

4. The apparatus of claim 1, wherein the fresh host cells are not infected by the M13 phage.

5. The apparatus of claim 1, wherein the rate of inflow of fresh host cells and the rate of outflow are substantially the same.

6. The apparatus of claim 1, wherein the inflow and outflow rates are controlled to maintain a substantially constant number of host cells in the lagoon.

7. The apparatus of claim 1, wherein the inflow and outflow rates are controlled to maintain a substantially constant frequency of fresh host cells in the lagoon.

8. The apparatus of claim 1, wherein the lagoon comprises an inflow connected to a vessel comprising a mutagen, and wherein the inflow of mutagen is controlled to maintain a concentration of the mutagen in the lagoon that is sufficient to induce mutations in the bacterial host cells.

9. The apparatus of claim 1, wherein the lagoon comprises an inflow connected to a vessel comprising an inducer.

10. The apparatus of claim 1, wherein the inducer induces expression of mutagenesis-promoting genes in the bacterial host cells.

11. The apparatus of claim 1, wherein the bacterial host cells comprise a mutagenesis plasmid comprising an expression cassette encoding a mutagenesis-promoting gene product.

12. The apparatus of claim 11, wherein the expression cassette encoding a mutagenesis-promoting gene product comprises a nucleic acid encoding a gene involved in the SOS stress response.

13. The apparatus of claim 12, wherein the gene involved in the SOS stress response is UmuC, UmuD', or RecA.

14. The apparatus of claim 11, wherein the expression cassette encoding a mutagenesis-promoting gene product comprises a conditional promoter, the activity of which depends on the presence of an inducer.

15. The apparatus of claim 1, wherein the turbidostat comprises a vessel comprising a mutagen, a vessel comprising an inducer, or a vessel comprising a mutagen and a vessel comprising an inducer.

16. The apparatus of claim 1, wherein the expression construct encoding the pIII protein and the expression construct encoding the pIII-neg protein are situated on the same plasmid.

17. The apparatus of claim 1, wherein the bacterial host cells comprise an accessory plasmid.

18. The apparatus of claim 17, wherein the accessory plasmid comprises an expression construct encoding the pIII protein.

19. The apparatus of claim 17, wherein the bacterial host cells comprise the accessory plasmid and together the phage genome and the accessory plasmid comprise all genes required for the generation of infectious phage.

20. The apparatus of claim 1, wherein the pIII-neg expression construct comprises a conditional promoter regulating the expression of the pIII-neg gene, wherein the activity of the conditional promoter depends on an undesired function of a gene product encoded by the gene of interest.

* * * * *